(12) United States Patent
Wender et al.

(10) Patent No.: US 6,624,189 B2
(45) Date of Patent: Sep. 23, 2003

(54) BYROSTATIN ANALOGUES, SYNTHETIC METHODS AND USES

(75) Inventors: Paul A. Wender, Menlo Park, CA (US); Blaise Lippa, Stonington, CT (US); Cheol-Min Park, Gurnee, IL (US); Kevin W. Hinkle, Chapel Hill, NC (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 09/728,929

(22) Filed: Nov. 30, 2000

(65) Prior Publication Data

US 2002/0137789 A1 Sep. 26, 2002

Related U.S. Application Data

(60) Provisional application No. 60/168,181, filed on Nov. 30, 1999.

(51) Int. Cl.[7] ................. A61K 31/335; A61K 31/35; C07D 267/22; C07D 323/00; A61P 37/00
(52) U.S. Cl. ................. 514/450; 514/452; 514/453; 514/455; 514/456; 540/456; 549/267
(58) Field of Search .................. 514/450, 452, 514/453, 455, 456; 549/267; 540/456

(56) References Cited

U.S. PATENT DOCUMENTS

| | | | |
|---|---|---|---|
| 4,560,774 A | 12/1985 | Petit et al. | 549/267 |
| 4,833,257 A | 5/1989 | Petit et al. | 549/267 |
| 5,891,870 A | 4/1999 | Dreidger et al. | 514/183 |
| 6,060,505 A | 5/2000 | Blumberg et al. | 514/449 |

OTHER PUBLICATIONS

Wender et al., Synthesis and Biological Evaluation of a New Class of Bryostatin Analogues: the Role of the C20 Substituent in Protein Kinase C Binding, Tetrahedron Letters, vol. 41, No. 35, pp. 6725–6729, Aug. 2000.*
Registry printout of Bryostatin 4, 5, 10 and 15, 2003.*
Evans, D.A.; et al., Angew. Chem. Int. Ed. 37:2354–2359 (1998).
Evans, D.A.; et al., Angew. J. Am. Chem. Soc. 121:7540–7552 (1999).
Harada et al., J. Am. Chem. Soc. 115:7665–7674 (1993).
Kageyama, M., et al., J. Am. Chem. Soc. 112:7407–7408 (1990).
Masamune, S., Pure Appl. Chem 60:1587–1596 (1988).
Masamune, S., Chimica 42:210–211 (1988).
Ohmori, K., et al., Angew. Chem., Int. Ed. 39(13):2290–2294 (2000).
Pettit, G.R., et al., J. Am. Chem. Soc. 104:6846–6848 (1982).
Pettit, G.R., J. Nat. Prod. 59:812–821 (1996).
Theisen, P.D., et al., J. Org. Chem. 53:2374–2378 (1998).
Wender, P.A., et al., Proc. Natl. Acad. Sci. U.S.A. 85:7197–7201 (1988).
Wender, P.A., et al., Proc. Natl. Acad. Sci. U.S.A. 92:239 (1995).
Wender, P.A., et al., J. Am. Chem. Soc. 120:4534–4535 (1998).
Wender, P.A., et al., Proc. Natl. Acad. Sci. U.S.A. 95:6624–6629 (1998).
Wender, P.A., et al., Tetrahedron Letters 39:8625–8628 (1998).
Wender, P.A., et al., Tetrahedron Letters 41:1007–1011 (2000).

* cited by examiner

*Primary Examiner*—Brenda Coleman
(74) *Attorney, Agent, or Firm*—David A. Lowin

(57) ABSTRACT

Biologically active compounds related to the bryostatin family of compounds, having simplified spacer domains and/or imroved recognition domains are disclosed, including methods of preparing and utilizing the same.

30 Claims, No Drawings

BYROSTATIN ANALOGUES, SYNTHETIC METHODS AND USES

CROSS-REFERENCE TO RELATED APPLICATIONS

This application claims the benefit of provisional U.S. Application Serial No. 60/168,181, filed Nov. 30, 1999, incorporated herein by reference.

GOVERNMENT INTEREST

This invention was made with the support of NIH grant number CA31845. Accordingly, the U.S. Government may have certain rights in this invention.

BACKGROUND OF THE INVENTION

1. Field of the Invention

The present invention concerns biologically active compounds related to the bryostatin family of compounds, and to methods of preparing and utilizing the same.

2. Introduction

Cancer is a major cause of death in the developed countries, with more than 500,000 human fatalities occurring annually in the United States. Cancers are generally the result of the transformation of normal cells into modified cells that proliferate excessively, leading to the formation of abnormal tissues or cell populations. In many cancers, cell proliferation is accompanied by dissemination (metastasis) of malignant cells to other parts of the body which spawn new cancerous growths. Cancers can significantly impair normal physiological processes, ultimately leading to patient mortality. Cancers have been observed for many different tissue and cell types, with cancers of the lung, breast, and colorectal system accounting for about half of all cases.

Currently, about one-third of cancer patients can be cured by surgical or radiation techniques. However, these approaches are most effective with cancerous lesions that have not yet metastasized to other regions of the body. Chemotherapeutic techniques currently cure another 17% of cancer patients. Combined chemotherapeutic and non-chemotherapeutic protocols can further enhance prospects for full recovery. Even for incurable cancer conditions, therapeutic treatments can be useful to achieve remission or at least extend patient longevity.

Numerous anticancer compounds have been developed over the past several decades (e.g., Katzung, 1998; Wilson et al., 1991; Hardman et al., 1996). While these compounds comprise many different classes that act by a variety of mechanisms, one general approach has been to block the proliferation of cancerous cells by interfering with cell division. For example, anthracyclines, such as doxorubicin and daunorubicin, have been found to intercalate DNA, blocking DNA and RNA synthesis and causing strand scission by interacting with topoisomerase II. The taxanes, such as Taxol™ and Taxotere™, disrupt mitosis by promoting tubulin polymerization in microtubule assembly. Cis-platin forms interstrand crosslinks in DNA and is effective to kill cells in all stages of the cell cycle. As another example, cyclophosphamide and related alkylating agents contain di-(2-chloroethyl)-amino groups that bind covalently to cellular components such as DNA.

The bryostatins (Formula A) are a family of naturally occurring macrocyclic compounds originally isolated from marine bryozoa. Currently, there are about 20 known natural bryostatins which share three six-membered rings desig nated A, B and C, and which differ mainly in the nature of their substituents at C7 ($OR^A$) and C20 ($R^B$) (Pettit, 1996).

Formula A

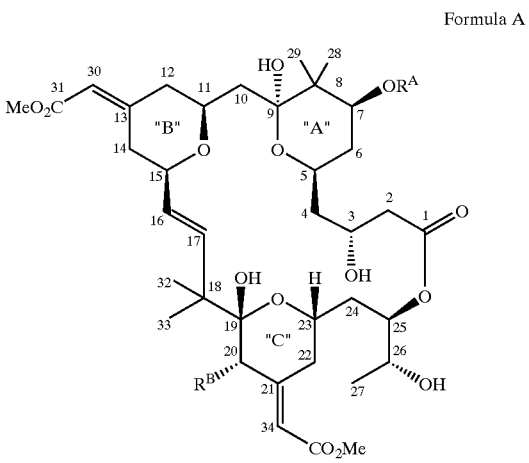

The bryostatins exhibit potent activity against a broad range of human cancer cell lines and provide significant in vivo life extensions in murine xenograft tumor models (Pettit et al., 1982; Hornung et al., 1992; Schuchter et al., 1991; Mohammad et al., 1998). Doses that are effective in vivo are extremely low, with activities demonstrated for concentrations as low as 1 μg/kg (Schuchter et al., 1991). Among additional therapeutic responses, the bryostatins have been found to promote the normal growth of bone marrow progenitor cells (Scheid, 1994; Kraft, 1996), provide cellular protection against normally lethal doses of ionizing radiation (Szallasi, 1996), and stimulate immune system responses that result in the production of T cells, tumor necrosis factors, interleukins and interferons (Kraft, 1996; Lind, 1993). Bryostatins are also effective in inducing transformation of chronic lymphocytic leukemia cells to a hairy cell type (Alkatib, 1993), increasing the expression of p53 while decreasing the expression of bcl-2 in inducing apoptosis in cancer cells (Maki, 1995; Mohammad, 1995) or at least pre-disposing a cell towards apoptosis, and reversing multidrug resistance (MDR) (Spitaler, 1998).

At the molecular level, bryostatins have been shown to competitively inhibit the binding of plant-derived phorbol esters and endogenous diacyl glycerols to protein kinase C (PKC) at nanomolar to picomolar drug concentrations (DeVries, 1998), and to stimulate comparable kinase activity (Kraft, 1986; Berkow, 1985; Ramsdell, 1986). Unlike the phorbol esters, however, the bryostatins do not act as tumor promoters. Thus, the bryostatins appear to operate through a mode of action different from, and complementary to, the modes of action of established anticancer agents; human clinical trials are presently evaluating bryostatin combination therapy with cisplatin or taxol.

Various studies have demonstrated good affinity for bryostatins in which $R^A$ is hydroxyl, acetyl, pivaloyl, or n-butanoate, and $R^B$ is H, acetyl, n-butanoate, or 2,4-unsaturated octanoate, as measured by PKC binding assay (Wender et al., 1988). The double bond between C13 and C30 can be hydrogenated or epoxidized without significant loss of binding affinity. Hydrogenation of the C21–C34 alkene or acetylation of the C26 hydroxyl, on the other hand, can significantly reduce binding affinity. Inversion of the stereoconfiguration at C26 leads to modest loss of activity (approx. 30-fold) and the suggestion that the methyl group may limit rotation of bonds proximate to the methyl group and contribute to the apparent high binding affinity observed for the bryostatins. Elimination of the hydroxyl at C19 (with concomitant omission of the C20 $R^B$ group) causes an approximately 100-fold to 200-fold decrease in binding. Likewise, impairing the accessibility of the C26 hydroxymethyl moiety by replacement of the C26 hydroxyl, or by replacing the methyl or hydrogen substituents of C26 with a tert-butyl or similar bulky substituent, has been proposed for diminishing toxicity (Blumberg et al., 1997).

Although the bryostatins have been known for some time, their low natural abundance, difficulties in isolation and severely limited availability through total synthesis have impeded efforts to elucidate their mode of action and to advance their clinical development. Recently, synthetic analogues of bryostatin were reported wherein the C4–C14 spacer domain was replaced with simplified spacer segments using a highly efficient esterification-macrotransacetalization (Wender et al., 1998a, 1998b). The reported analogues retained orientation of the C1-, C19-, C26-oxygen recognition domain as determined by NMR spectroscopic comparison with bryostatin and varying degrees of PKC-binding affinity. The one analogue tested for in vitro inhibition in human tumor cell lines was reported to posess significant activity. It has remained, however, desired to provide new, simplified, and more readily accessible synthetic agents based on the bryostatin structure to further elucidate the molecular basis of bryostatin's activity and develop improved and more readily available clinical candidates, especially for anticancer applications.

SUMMARY OF THE INVENTION

One aspect of the present invention concerns simplified bryostatin analogues, i.e., the compounds represented by Formula I:

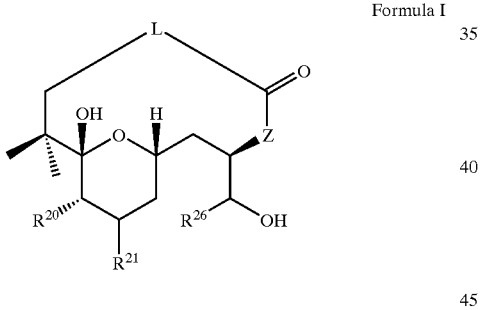

Formula I wherein:
$R^{20}$ is H, OH, or $O_2CR'$;
$R^{21}$ is $=CR^aR^b$ or $R^{21}$ represents independent moieties $R^c$ and $R^d$ where:
  $R^a$ and $R^b$ are independently H, $CO_2R'$, $CONR^cR^d$ or R';
  $R^c$ and $R^d$ are independently H, alkyl, alkenyl or alkynyl, or $(CH_2)_nCO_2R'$ where n is 1, 2 or 3;
$R^{26}$ is H, OH or R';
  each R' being independently selected from the group: alkyl, alkenyl or alkynyl, or aryl, heteroaryl, aralkyl or heteroaralkyl;
L is a straight or branched linear, cyclic or polycyclic moiety, containing a continuous chain of preferably from 6 to 14 chain atoms, which substantially maintains the relative distance between the C1 and C17 atoms and the directionality of the C1C2 and C16C17 bonds of naturally-occurring bryostatin; and
Z is —O— or —N(H)—;
and the pharmaceutically acceptable salt thereof.

In a preferred aspect of the recognition domain in this embodiment $R^{26}$ is H or methyl, particularly when $R^{21}$ is $=C(H)CO_2R'$. Especially preferred are the compounds where $R^{26}$ is H. A preferred upper limit on carbon atoms in any of $R^d$, $R^e$ and R' is about 20, more preferably about 10 (except as otherwise specifically noted, for example, with reference to the embodiment of the invention where a preferred $R^{20}$ substituent has about 9 to 20 carbon atoms). In a preferred aspect of the spacer domain of this embodiment, L contains a terminal carbon atom that, together with the carbon atom corresponding to C17 in the native bryostatin structure, forms a trans olefin.

Another aspect of the invention concerns the simplified bryostatin analogues represented by Formulae II–V:

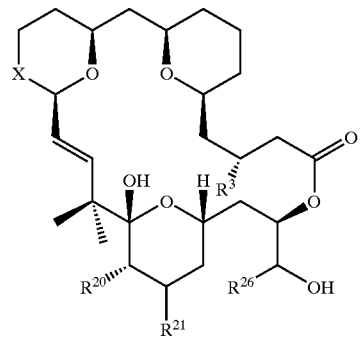

Formula II

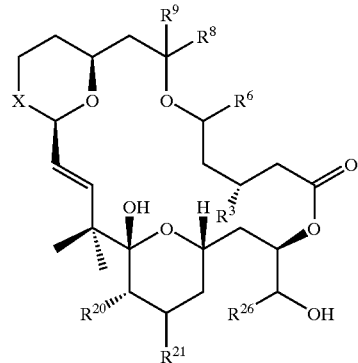

Formula III

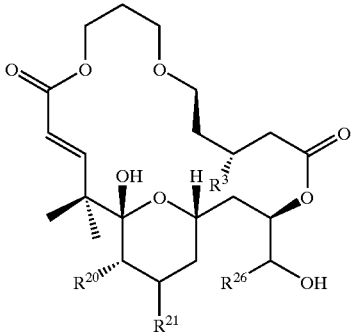

Formula IV

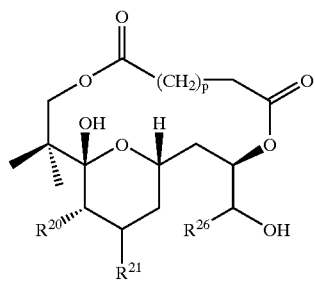

Formula V wherein:

R³ is H, OH or a protecting group;

R⁶ is H, H or =O;

R⁸ is selected from the group: H, OH, R', —(CH$_2$)$_n$O(O)CR' or (CH$_2$)$_n$CO$_2$-haloalkyl where n is 0, 1, 2, 3, 4 or 5;

R⁹ is H or OH;

R²⁰, R²¹, R²⁶ and R' are as defined above with respect to Formula I;

p is 1, 2, 3 or 4; and

X is C, O, S or N—R$^e$ where R$^e$ is COH, CO$_2$R' or SO$_2$R', and the pharmaceutically acceptable salts thereof.

In a preferred aspect, the invention relates to the C26 des-methyl analogue of Formula IIa:

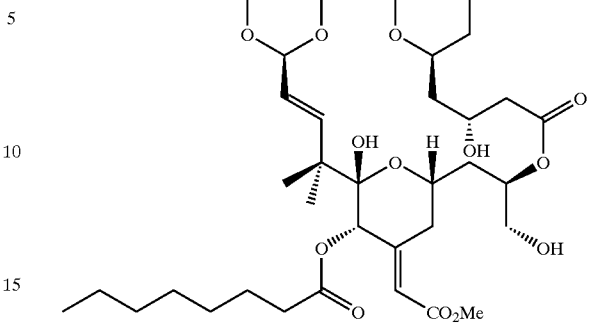

Formula IIa and to pharmaceutical compositions and methods of treatment therewith.

Still another aspect of the invention relates to the C26 des-methyl homologues of the native bryostatins, as illustrated in Formula VI:

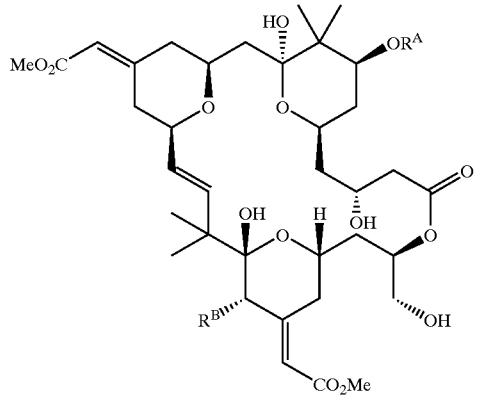

Formula VI where OR$^A$ and R$^B$ correspond to the naturally occurring bryostatin substituents, including:

| Byrostatin | OR$^A$ | R$^B$ |
|---|---|---|
| 1 | —O$_2$C—CH$_3$ | —O$_2$C—CH=CH—CH=CH—CH$_2$—CH$_2$—CH$_3$ |
| 2 | —OH | —O$_2$C—CH=CH—CH=CH—CH$_2$—CH$_2$—CH$_3$ |
| 4 | —O$_2$C—C(CH$_3$C)$_3$ | —O$_2$C—CH$_2$—CH$_3$ |
| 5 | —O$_2$C—C(CH$_3$C)$_3$ | —O$_2$C—CH$_3$ |
| 6 | —O$_2$C—CH$_2$—CH$_3$ | —O$_2$C—CH$_3$ |
| 7 | —O$_2$C—CH$_3$ | —O$_2$C—CH$_3$ |
| 8 | —O$_2$C—CH$_2$—CH$_3$ | —O$_2$C—CH$_2$—CH$_3$ |
| 9 | —O$_2$C—CH$_3$ | —O$_2$C—CH$_2$—CH$_3$ |
| 10 | —O$_2$C—C(CH$_3$C)$_3$ | —H |
| 11 | —O$_2$C—CH$_3$ | —H |
| 12 | —O$_2$C—CH$_2$—CH$_3$ | —O$_2$C—CH=CH—CH=CH—CH$_2$—CH$_2$—CH$_3$ |
| 13 | —O$_2$C—CH$_2$—CH$_3$ | —H |
| 14 | —O$_2$C—C(CH$_3$C)$_3$ | —OH |
| 15 | —O$_2$C—CH$_3$ | —O$_2$C—CH=CH—CH=CH—CH$_2$—CH$_2$—CH$_3$ |
| 18 | —O$_2$C—C(CH$_3$C)$_3$ | —H | such as C26 des-methyl Bryostatin 1, the compound of Formula VIa:

Formula VIa

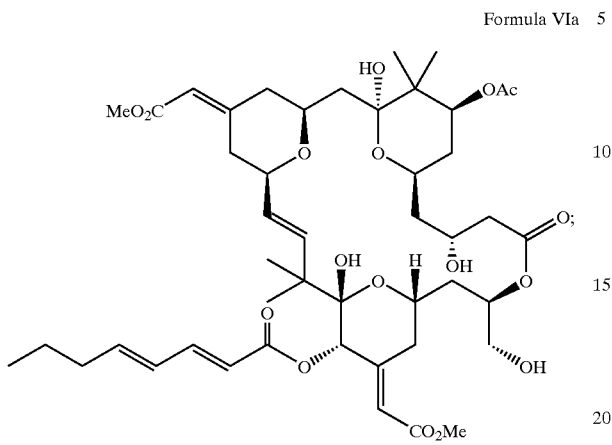

the C26 des-methyl homologues of the native bryostatins, as illustrated in Formula VII:

Formula VII

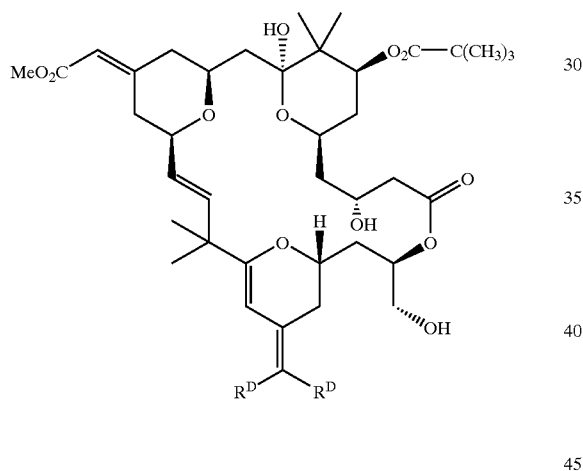

where $R^C$ and $R^D$ correspond to the naturally occurring bryostatin substituents, including:

| Byrostatin | $R^C$ | $R^D$ |
|---|---|---|
| 16 | —H | —CO$_2$Me |
| 17 | —CO$_2$Me | —H | and to the C26 des-methyl homologues of the native Bryostatin 3, as illustrated in the following formula:

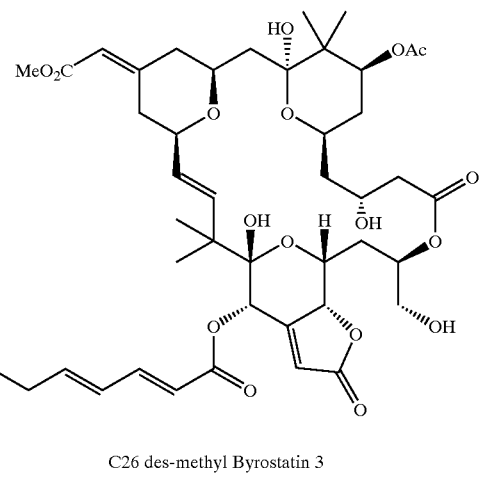

C26 des-methyl Byrostatin 3 and to pharmaceutical compositions and methods of treatment therewith.

Excluded from the scope of the invention are the analogues of Formula 1998a (where $R^3$ is H or OH) and the analogue of Formula 1998b:

1998a

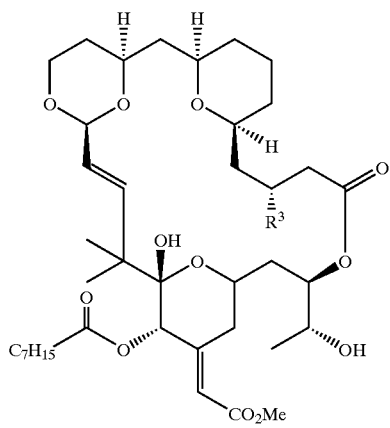

1998b

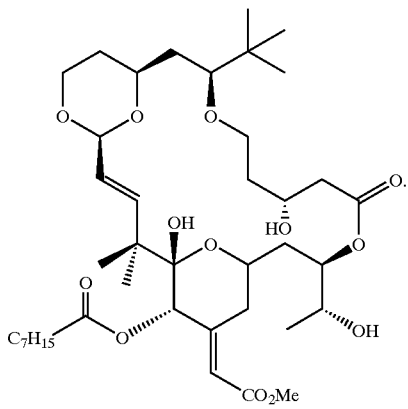

In another aspect, the invention relates to a pharmaceutical composition containing a therapeutically effective amount of a compound of Formula I or a pharmaceutically acceptable salt thereof admixed with at least one pharmaceutically acceptable excipient.

In still another aspect, the invention relates to a method of treating hyperproliferative cellular disorders, particularly cancer in a mammal by administering to a mammal in need of such treatment a therapeutically effective amount of a compound of Formula I or a pharmaceutically acceptable salt thereof, either alone or in combination with a second agent, preferably a second anti-cancer agent that acts by a distinct mechanism vis-a-vis the mechanism of the compound of Formula I.

In yet another aspect, the invention relates to methods of treatment for a mammal having an immune-related disease or receiving immunosuppressive therapy, by administering of a therapeutically effective amount of a compound of Formula I or a pharmaceutically acceptable salt thereof.

In another aspect of the invention, there is provided a method for the synthesis of bryostatin analogues, including the steps of esterification and macrotrasacetylization of a protected recognition domain with a protected linker synthon, followed by deprotection. Particularly preferred is reduction of a C26 OBn protected predursor to give the corresponding C26 des-methyl bryostatin analogue. A related aspect of the invention entails the novel products made by the foregoing process.

The invention also includes pharmaceutical compositions containing one or more compounds in accordance with the invention.

In another aspect, the invention includes a method of inhibiting growth, or proliferation, of a cancer cell. In the method, a cancer cell is contacted with a bryostatin analogue compound in accordance with the invention in an amount effective to inhibit growth or proliferation of the cell. In a broader aspect, the invention includes a method of treating cancer in a mammalian subject, especially humans. In the method, a bryostatin analogue compound in accordance with the present invention is administered to the subject in an amount effective to inhibit growth of the cancer in the patient.

These and other objects and features of the invention will be better understood in light of the following detailed description.

DETAILED DESCRIPTION

Definitions

As used in the present specification, the following words and phrases are generally intended to have the meanings as set forth below, except to the extent that the context in which they are used indicates otherwise.

As used herein, the terms "alkyl", "alkenyl" and "alkynyl," refer to saturated and unsaturated monovalent moieties in accordance with their standard meanings, including straight-chain, branched-chain and cyclic moieties, optionally containing one or more intervening heteroatoms, such as oxygen, sulfur, and nitrogen in the chain or ring, respectively. Exemplary alkyl groups include methyl, ethyl, isopropyl, cyclopropyl, 2-butyl, cyclopentyl, and the like. Exemplary alkenyl groups include 2-pentenyl, 2,4-pentadienyl, 2-octenyl, 2,4,6-octatrienyl, $CH_3$—$CH_2$—$CH_2$—CH=CH—CH=CH—, cyclopentadienyl, and the like. Exemplary alkynyl groups include $CH_3C\equiv CCH_2$—, 4-pentyn-1-yl, and the like. Exemplary cyclic moieties include cyclopentyl, cyclohexyl, furanyl, pyranyl, tetrahydrofuranyl, 1,3-dioxanyl, 1,4-dioxanyl, pyrrolidyl, piperidyl, morpholino, and reduced forms of furanyl, imidazyl, pyranyl, pyridyl, and the like.

"Lower alkyl", "lower alkenyl", and "lower alkynyl" refer to alkyl, alkenyl, and alkynyl groups containing 1 to 4 carbon atoms.

The term "aryl" denotes an aromatic ring or fused ring structure of carbon atoms with no heteroatoms in the ring(s). Examples are phenyl, naphthyl, anthracyl, and phenanthryl. Preferred examples are phenyl and napthyl.

The term "heteroaryl" is used herein to denote an aromatic ring or fused ring structure of carbon atoms with one or more non-carbon atoms, such as oxygen, nitrogen, and sulfur, in the ring or in one or more of the rings in fused ring structures. Examples are furanyl, pyranyl, thienyl, imidazyl, pyrrolyl, pyridyl, pyrazolyl, pyrazinyl, pyrimidinyl, indolyl, quinolyl, isoquinolyl, quinoxalyl, and quinazolinyl. Preferred examples are furanyl, imidazyl, pyranyl, pyrrolyl, and pyridyl.

"Aralkyl" and "heteroaralkyl" refer to aryl and heteroaryl moieties, respectively, that are linked to a main structure by an intervening alkyl group, e.g., containing one or more methylene groups.

"Alkoxy", "alkenoxy", and "alkynoxy" refer to an alkyl, alkenyl, or alkynyl moiety, respectively, that is linked to a main structure by an intervening oxygen atom.

It will be appreciated that the alkyl, alkenyl, alkynyl, aryl, heteroaryl, aralkyl, and heteroaralkyl moieties utilized herein can be unsubstituted or substituted with one or more of the same or different substituents, which are typically selected from —X, —R', =O, —OR', —SR', =S, —NR'R', —NR'R'$^+$, =NR', —$CX_3$, —CN, —OCN, —SCN, —NCO, —NCS, —NO, —$NO_2$, =$N_2$, —$N_3$, —S(O)$_2$O$^-$, —S(O)$_2$OH, —S(O)$_2$R', —C(O)R', —C(O)X, —C(S)R', —C(S)X, —C(O)OR', —C(O)O$^-$, —C(S)OR', —C(O)SR', —C(S)SR', —C(O)NR'R', —C(S)NR'R' and —C(NR) NR'R', where each X is independently a halogen (F, Cl, Br, or I, preferably F or Cl) and each R' is independently hydrogen, alkyl, alkenyl, or alkynyl. In one embodiment, R' is lower alkyl, lower alkenyl, or lower alkynyl. NR'R' also includes moieties wherein the two R' groups form a ring with the nitrogen atom.

While practical size limits for the various substituent groups will be apparent to those skilled in the art, generally preferred are the alkyl, alkenyl, alkynyl, aryl, heteroaryl, aralkyl, and heteroaralkyl moieties containing up to about 40 carbon atoms, more preferably up to about 20 carbon atoms and most preferably up to about 10 carbon atoms (except as otherwise specifically noted, for example, with reference to the embodiment of the invention where a preferred $R^{20}$ substituent has about 7 to 20 carbon atoms).

As to any of the above groups that contain one or more substituents, it is understood, of course, that such groups do not contain any substitution or substitution patterns which are sterically impractical and/or synthetically non-feasible. In addition, the compounds of this invention include all stereochemical isomers and mixtures thereof arising from the substitution of these compounds.

Except as otherwise specifically provided or clear from the context, the term "compounds" of the invention should be construed as including the "pharmaceutically acceptable salts" thereof (which expression has been eliminated in certain instances for the sake of brevity).

The term "pharmaceutically acceptable salt" refers to salts which retain the biological effectiveness and properties of the compounds of this invention and which are not biologically or otherwise undesirable. In some cases, the compounds of this invention are capable of forming acid and/or base salts, derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

"Mammal" is intended to have its conventional meaning. Examples include humans, mice, rats, guinea pigs, horses, dogs, cats, sheep, cows, etc.

The term "treatment" or "treating" means any treatment of a disease in a mammal, including:

preventing the disease, that is, causing the clinical symptoms of the disease not to develop;

inhibiting the disease, that is, arresting the development of clinical symptoms; and/or relieving the disease, that is, causing the regression of clinical symptoms.

The term "effective amount" means a dosage sufficient to provide treatment for the disease state being treated. This will vary depending on the patient, the disease and the treatment being effected.

Compounds

The present invention provides new analogues of bryostatin that can be synthesized conveniently in high yields and which have useful biological activities. The compounds of the invention can be broadly described as having two main regions that are referred to herein as a "recognition domain" (or pharmacophoric region) and a relatively lipophilic "spacer domain" (or linker region). The recognition domain contains structural features that are analogous to those spanning C17 through C26 to C1, including the C ring formed in part by atoms C19 through C23, and the lactone linkage between C1 and C25 of the native bryostatin macrocycle. The spacer domain, on the other hand, joins the atoms corresponding to C1 through C17 of the native bryostatin macrocycle to substantially maintain the relative distance between the C1 and C17 atoms and the directionality of the C1C2 and C16C17 bonds, as illustrated by the arrows and distance "d" in Formula Ia (in which the substituent groups are as defined with reference to Formula I).

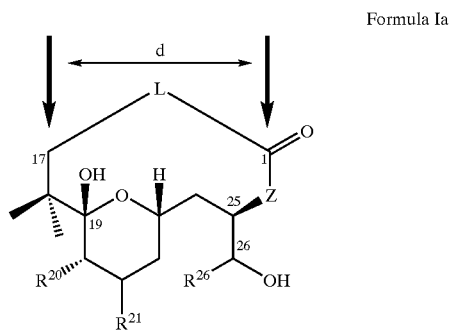

Formula Ia

In addition to its function of maintaining the recognition domain in an active conformation, the spacer domain (shown as "L" in Formula Ia and sometimes also referred to as a linker region) provides a moiety that can be readily derivatized according to known synthetic techniques to generate analogues having improved in vivo stability and pharmacological properties (e.g., by modulating side effect profiles) while retaining biological activity.

It has been found in the present invention that the linker region of of the bryostatin family can be varied significantly without eliminating activity. Thus, a wide variety of linkers can be used while retaining significant anticancer and PKC-binding activities. Preferably, the compounds of the present invention include a linker moiety L, which is a linear, cyclic, or polycyclic linker moiety containing a continuous chain of from 6 to 14 chain atoms, one embodiment of which defines the shortest path from C25 via C1 to C17. Thus, L may consist solely of a linear chain of atoms that links C17 via C1 to C25, or alteratively, may contain one or more ring structures which help link C17 via C1 to C25. Preferably, the linker region includes a lactone group (—C(=O)O—), or a lactam group (—C(=O)NH—), which is linked to C25 of the recognition region, by analogy to the C1 lactone moiety that is present in the naturally occurring bryostatins. In addition, it is preferred that the linker include a hydroxyl group analogous to the C3 hydroxyl found in naturally occurring bryostatins, to permit formation of an intramolecular hydrogen bond between the C3 hydroxyl of the linker and the C19 hydroxyl group of the recognition region (and optionally with the oxygen of the native B ring). In one preferred embodiment, the linker terminates with —CH(OH)CH$_2$C(=O)O—, for joining to C25 of the recognition region via an ester (or when cyclized a lactone) linkage.

In one embodiment of the invention where $R^{26}$ is H, the compounds of the invention differ from known bryostatins and bryostatin analogues in that the present compounds contain a primary alcohol moiety at C26, i.e., the present analogues lack a methyl group corresponding to the C27 methyl that is ordinarily present in naturally occurring bryostatins. Surprisingly, while the C27 methyl moiety was previously believed to limit rotation of the C26 alcohol and contribute to PKC binding affinity, it has been found that this structural modification can significantly increase PKC binding and also increases efficacy against cancer cells. Other modifications of $R^{26}$ are provided to further modulate these characteristics, as are the C26 des-methyl homologues of the native bryostatins.

In another aspect, the present invention provides bryostatins and bryostatin analogues in which $R^{20}$ is longer (e.g., having 9 to 20 or more carbon atoms) than the corresponding substituents at C20 in the native bryostatins (e.g., Bryostatin 3 having an 8-carbon atom moiety).

Certain preferred spacer domains employed in the compounds of the invention are illustrated in Formulae II through V:

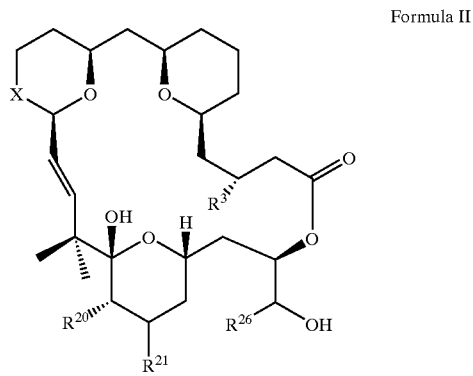

Formula II

-continued

Formula III

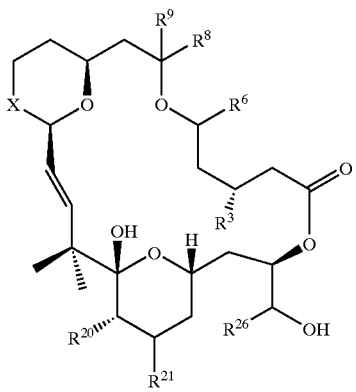

Formula IV

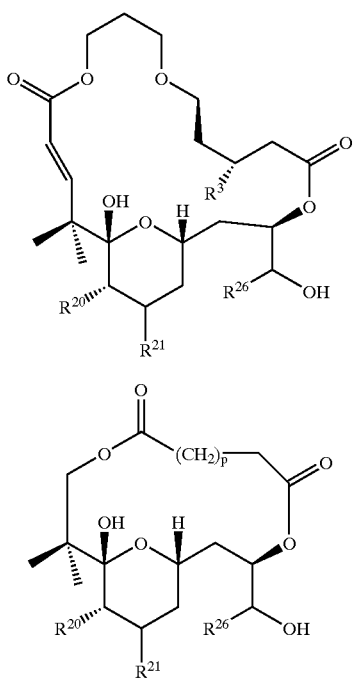

wherein:

$R^3$ is H, OH or a protecting group;

$R^6$ is H, H or =O;

$R^8$ is selected from the group: H, OH, R', —(CH$_2$)$_n$O(O)CR' or (CH$_2$)$_n$CO$_2$-haloalkyl, where n is 0, 1, 2, 3, 4 or 5;

$R^9$ is H or OH;

$R^{20}$, $R^{21}$, $R^{26}$ and R' are as defined above with respect to Formula I;

p is 1, 2, 3 or 4; and

X is C, O, S or N—$R^e$ where $R^e$ is a group that stabilizes the nitrogen's lone pair of electrons, such as COH, CO$_2$R' or SO$_2$R', the pharmaceutically acceptable salts thereof, and the corresponding lactams.

Excluded from the scope of the present invention are the compounds of formula 1998a where $R^3$ is H or OH and where $R^{20}$ is —O—C(O)—CH$_3$ or —O—C(O)—(CH$_2$)$_6$—CH$_3$, and the compounds of formula 1998b where R is H or t-Bu:

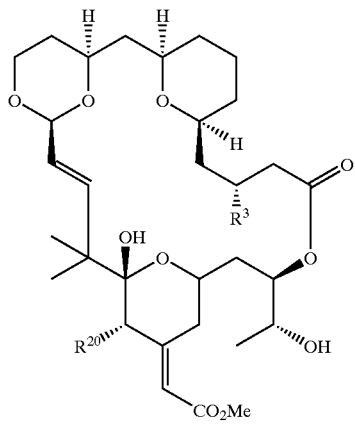
1998a

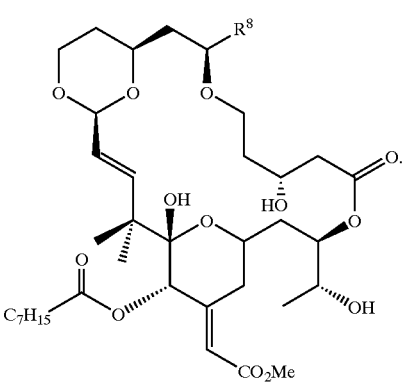
1998b

Nomenclature

For simplicity of reference, the compounds of Formulae I–V are named and numbered herein as corresponding to the naturally occurring bryostatin macrocycle, described above with reference to Formula A. For example, the C26 desmethyl homologue of native bryostatin 1 (a compound of the present invention) has the structure illustrated in Formula VIa:

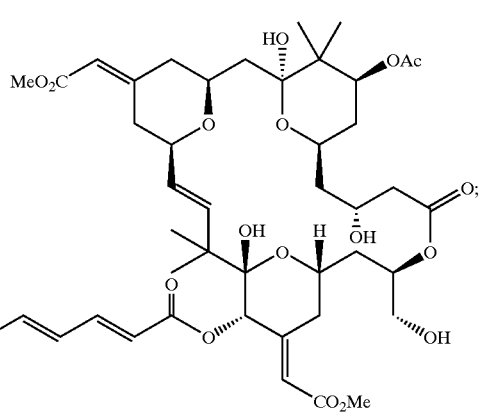
Formula VIa

By way of comparison, the analogues of the invention in which $R^{26}$ is hydrogen, such as those of Formula IIa and Formula IVa:

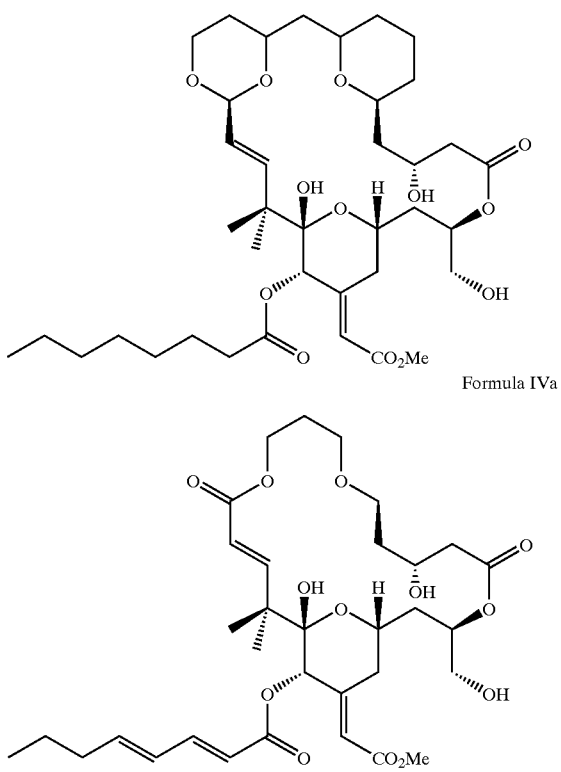

Formula IIa

Formula IVa are also referred to as "C26 des-methyl", notwithstanding that the structures corresponding to L (in Formula I) or the corresponding spacer domain (in Formulae II–V), or even the recognition domain, contain fewer carbon atoms than native bryostatin such that the "C26" position would be assigned a lower number were these analogues to be named without reference to the native structure.

Synthetic Reaction Parameters

The terms "solvent", "inert organic solvent" or "inert solvent" mean a solvent inert under the conditions of the reaction being described in conjunction therewith [including, for example, benzene, toluene, acetonitrile, tetrahydrofuran ("THF"), dimethylformamide ("DMF"), chloroform, methylene chloride (or dichloromethane), diethyl ether, methanol, pyridine and the like]. Unless specified to the contrary, the solvents used in the reactions of the present invention are inert organic solvents.

The terms "protecting group" or "blocking group" refer to any group which when bound to a functional group such as one or more hydroxyl, thiol, amino or carboxyl groups of the compounds (including intermediates thereof) prevents reactions from occurring at these groups and which protecting group can be removed by conventional chemical or enzymatic steps to reestablish the hydroxyl, thiol, amino or carboxyl group. The particular removable blocking group employed is not critical and preferred removable hydroxyl blocking groups include conventional substituents such as allyl, benzyl, acetyl, chloroacetyl, thiobenzyl, benzylidine, phenacyl, t-butyl-diphenylsilyl and any other group that can be introduced chemically onto a hydroxyl functionality and later selectively removed either by chemical or enzymatic methods in mild conditions compatible with the nature of the product.

The term "q.s." means adding a quantity sufficient to achieve a stated function, e.g., to bring a solution to the desired volume (i.e., 100%).

Unless specified to the contrary, the reactions described herein take place at atmospheric pressure within a temperature range from about 5° C. to 100° C. (preferably from 10° C. to 50° C.; most preferably at "room" or "ambient" temperature, e.g., 25° C.). Further, unless otherwise specified, the reaction times and conditions are intended to be approximate, e.g., taking place at about atmospheric pressure within a temperature range of about 5° C. to about 100° C. (preferably from about 10° C. to about 50° C.; most preferably about 25° C.) over a period of about 0.5 to about 10 hours (preferably about 1 hour). Parameters given in the Examples are intended to be specific, not approximate.

Isolation and purification of the compounds and intermediates described herein can be effected, if desired, by any suitable separation or purification procedure such as, for example, distillation, filtration, extraction, crystallization, column chromatography, thin-layer chromatography or thick-layer chromatography, or a combination of these procedures. Specific illustrations of suitable separation and isolation procedures can be had by reference to the general description and examples. However, other equivalent separation or isolation procedures can, of course, also be used.

Synthesis of the Compounds of Formula I

The compounds of the invention may be produced by any methods available in the art, inducing chemical and biological (e.g., recombinant and in vitro enzyme-catalyzed) methods. In one embodiment, the present invention provides a convergent synthesis in which subunits primarily corresponding to the recognition and spacer domains are separately prepared and then joined by esterification-macrotransacetalization (Wender et al., 1998a, 1998b, 1998c). Additional syntheses of the compounds of Formulae I–VI are described below with reference to the Reaction Schemes.

Reaction Scheme 1 illustrates synthesis of precursors for the recognition domain in compounds of the invention.

Reaction Scheme 1

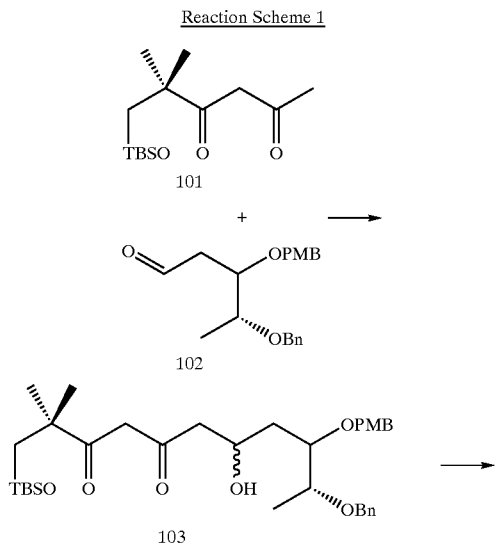

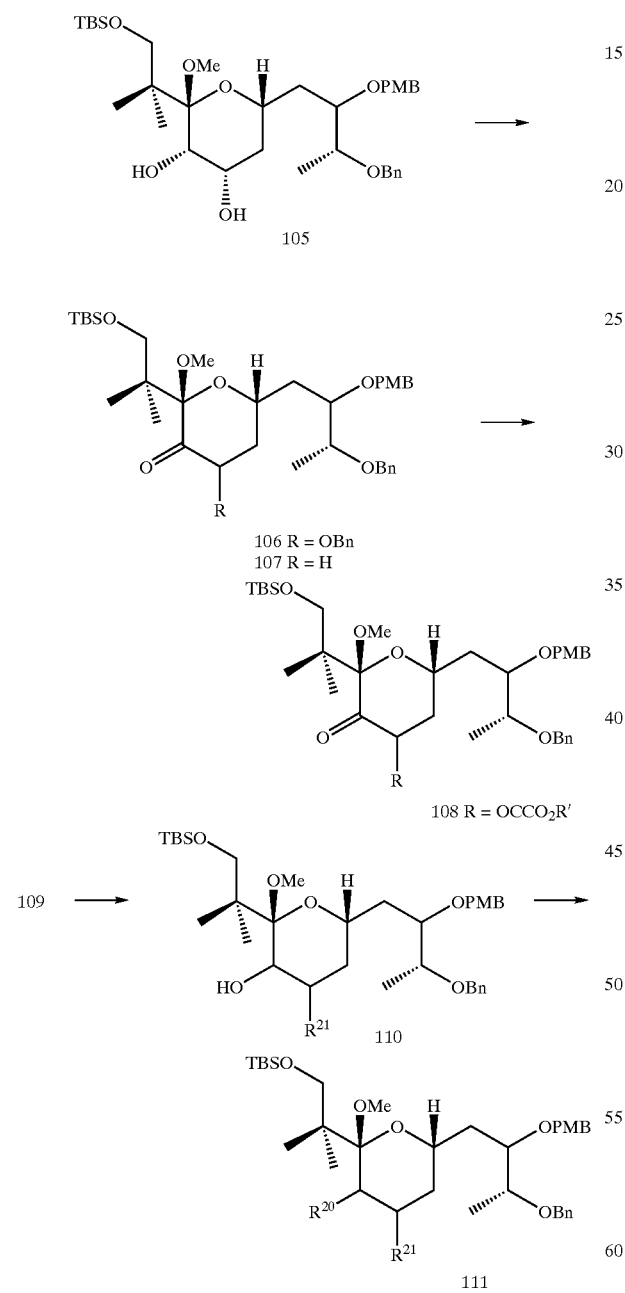
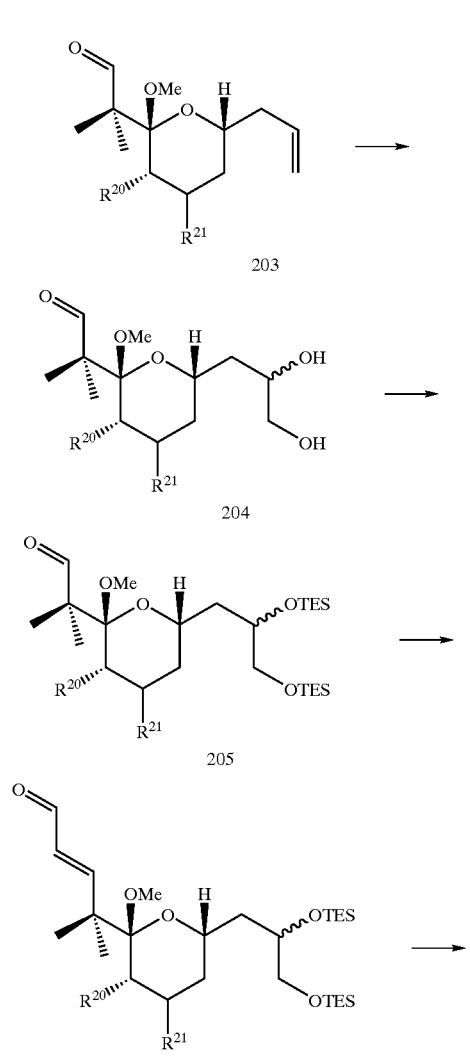
Reaction Scheme 2 illustrates the further synthesis of recognition domains for C26 des-methyl compounds of the invention.

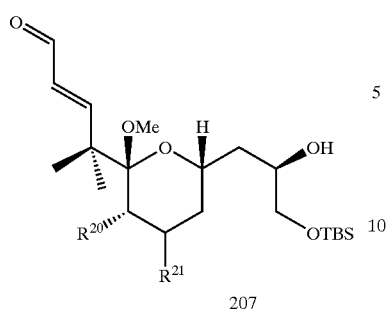
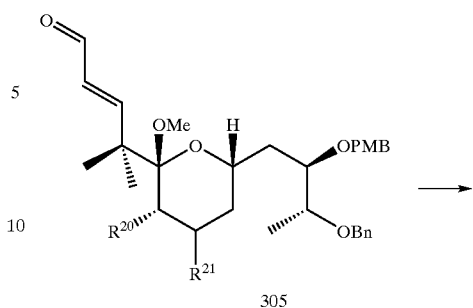
Reaction Scheme 3 illustrates synthesis of the protected alcohol precursor to many of the C26 methyl analogues of the invention.
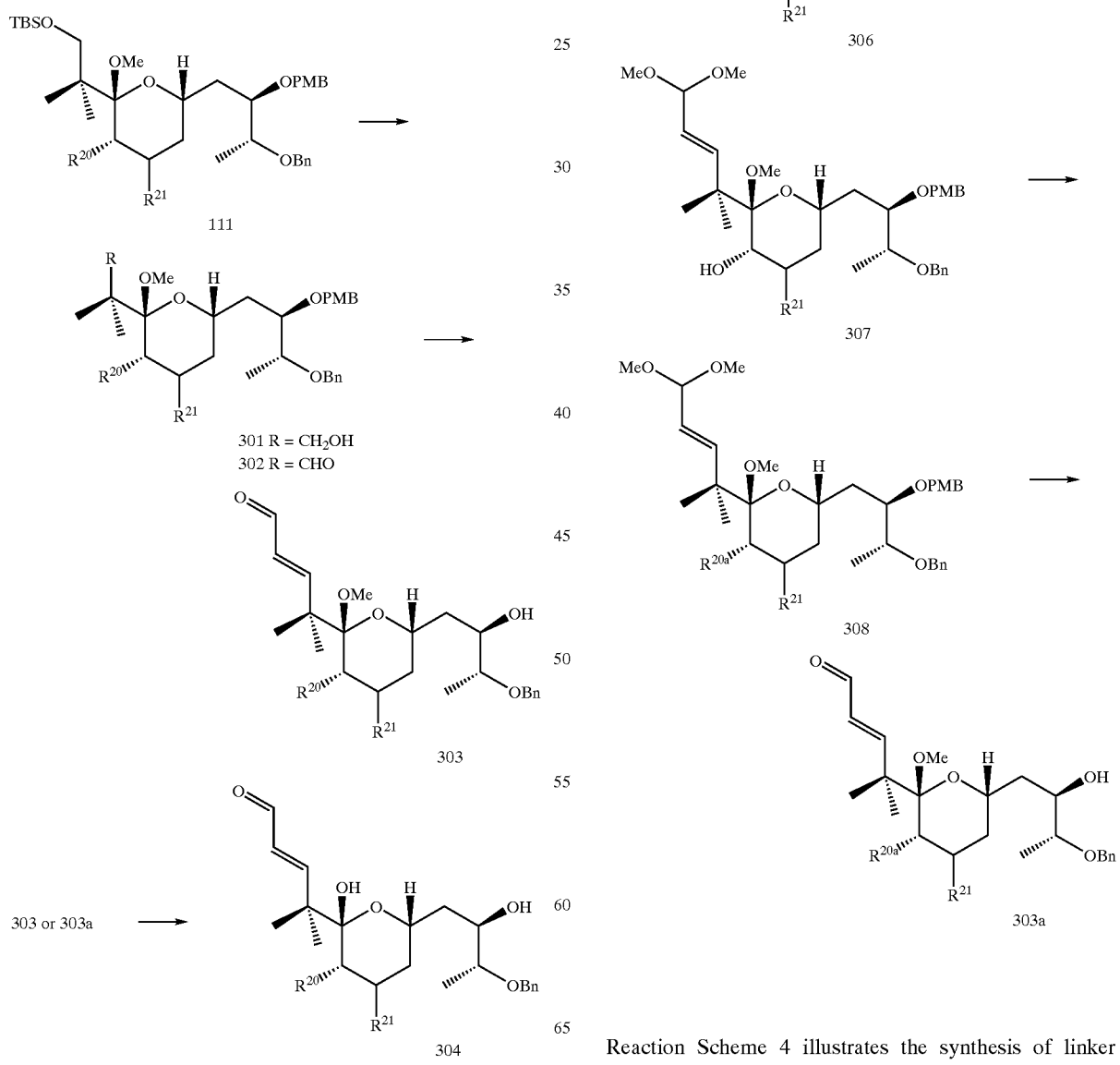
Reaction Scheme 4 illustrates the synthesis of linker synthons for preparing the compounds of Formula II.

Reaction Scheme 4
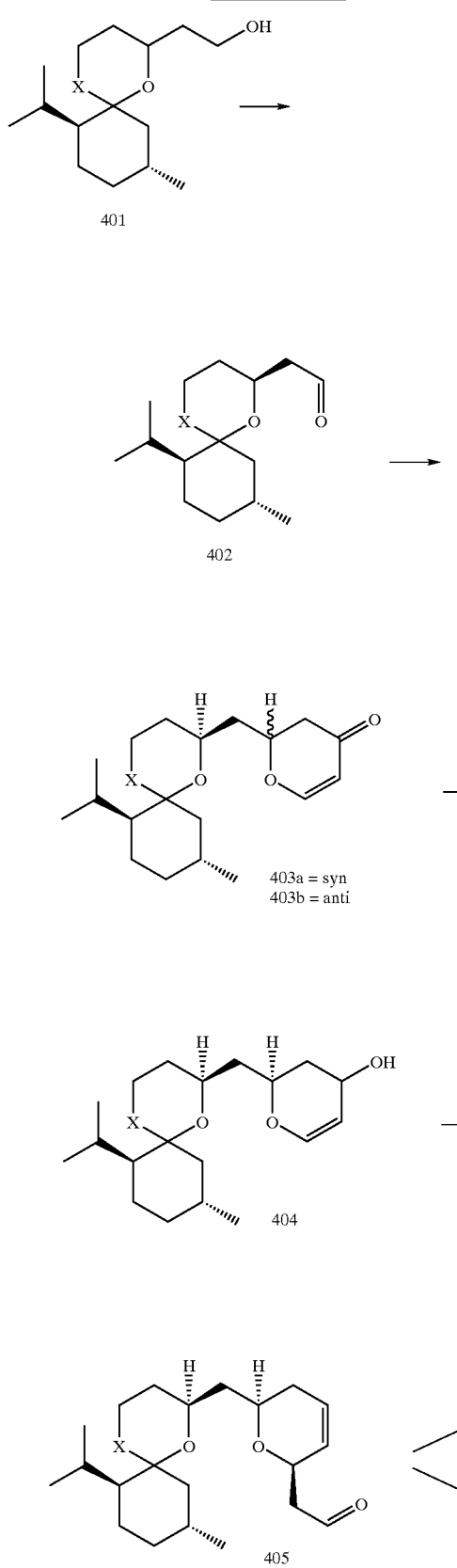
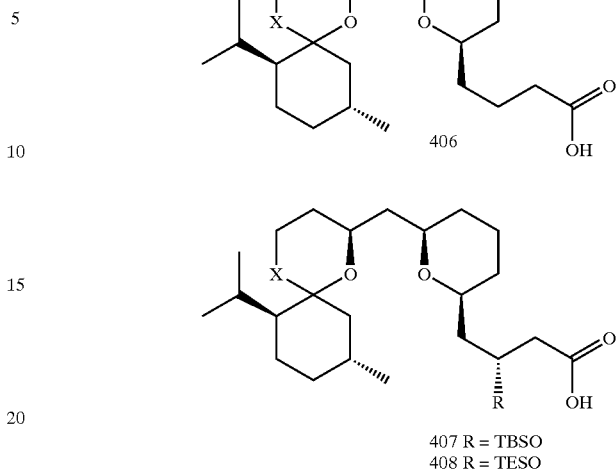
Reaction Scheme 5A illustrates the synthesis of linker synthons for preparing the compounds of Formula III where $R^9$ is OH.
Reaction Scheme 5A
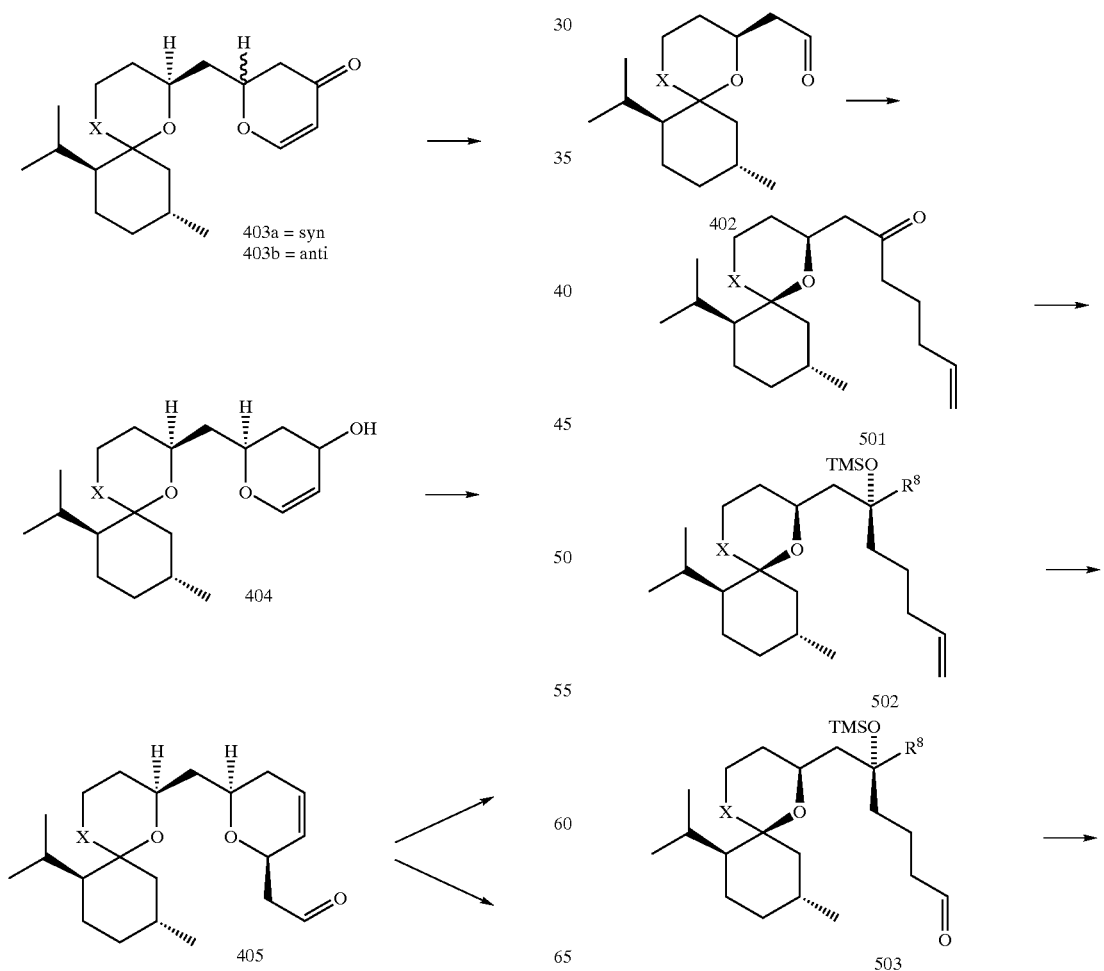

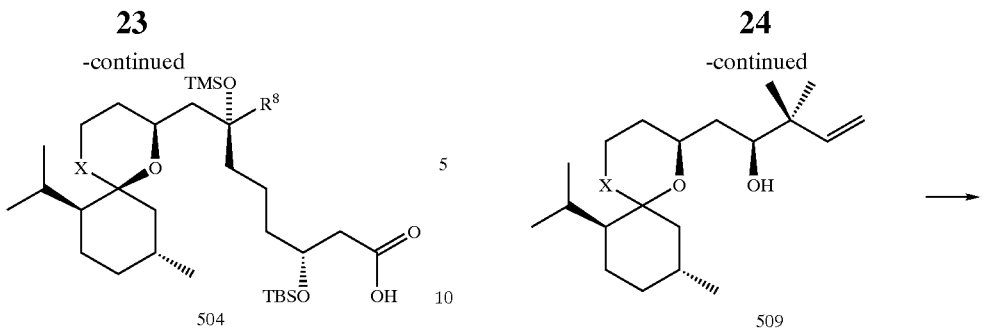

Reaction Scheme 5B illustrates the synthesis of linker synthons for preparing the compounds of Formula III where $R^8$ and/or $R^9$ are H.

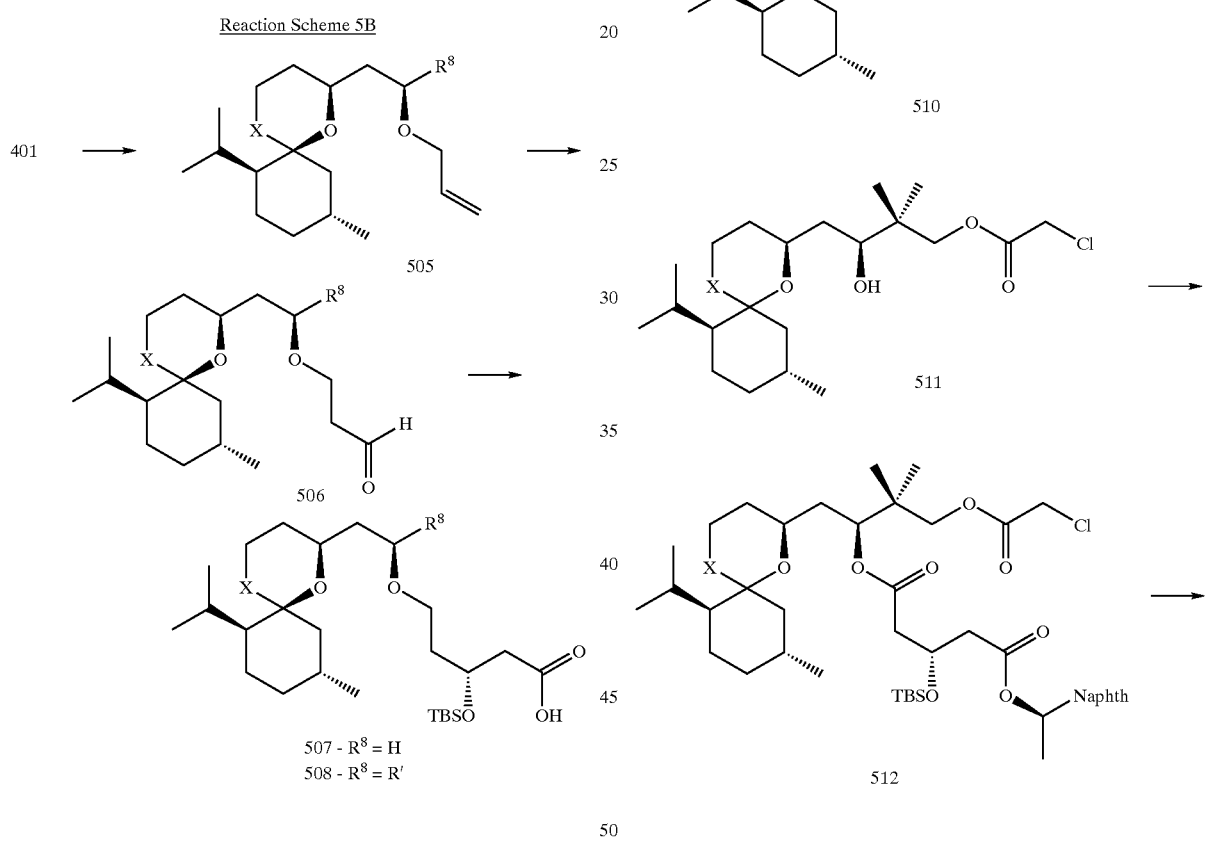

Reaction Scheme 5C illustrates the synthesis of linker synthons for preparing the compounds of Formula III where $R^6$ is =O with a variety of possible substituents at $R^8$.

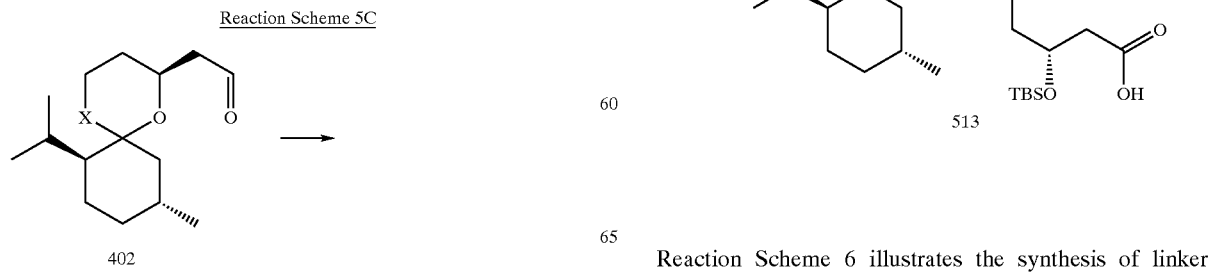

Reaction Scheme 6 illustrates the synthesis of linker synthons for preparing the compounds of Formula IV.

Reaction Scheme 6
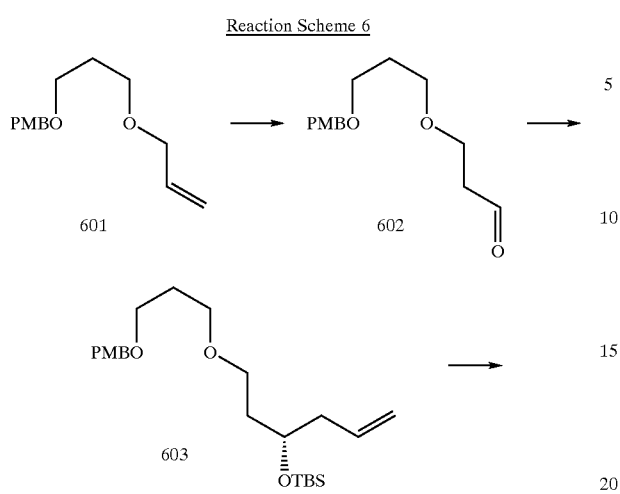
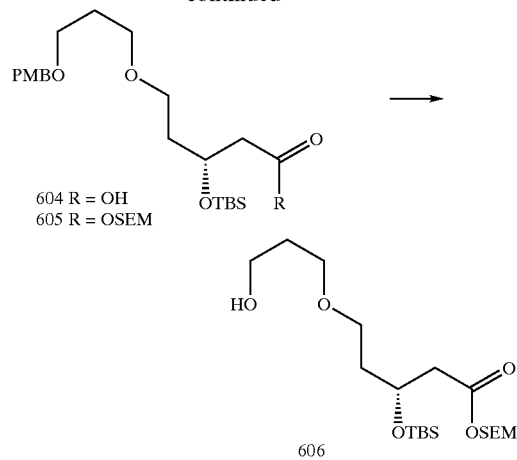
Reaction Scheme 7A illustrates the synthesis of the compounds of Formula II.
Reaction Scheme 7A
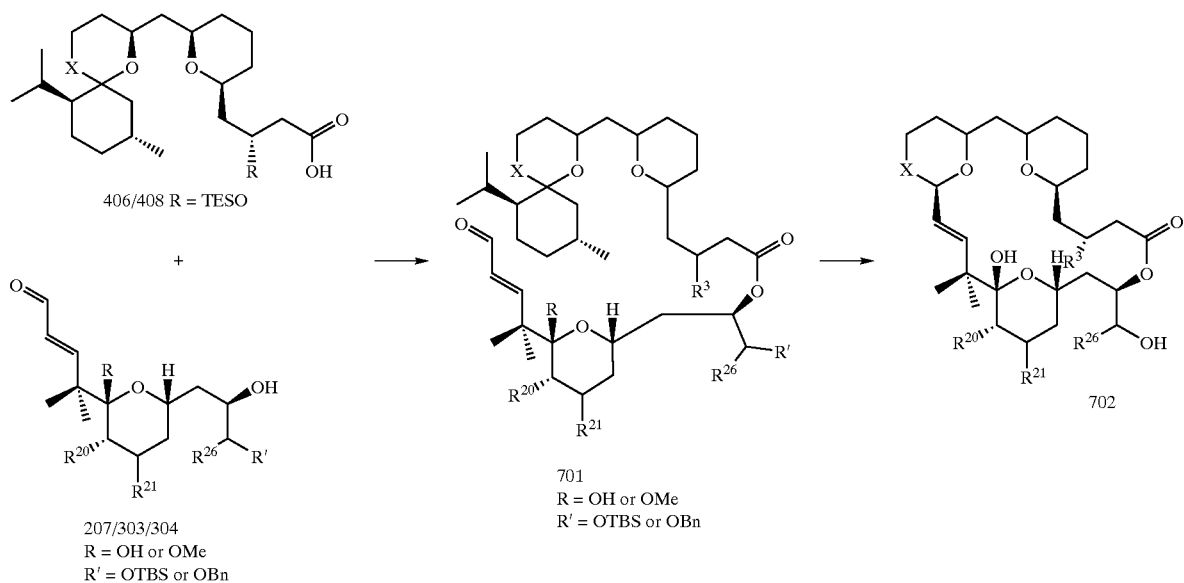
Reaction Scheme 7B illustrates the synthesis of the compounds of Formula III.

Reaction Scheme 7B
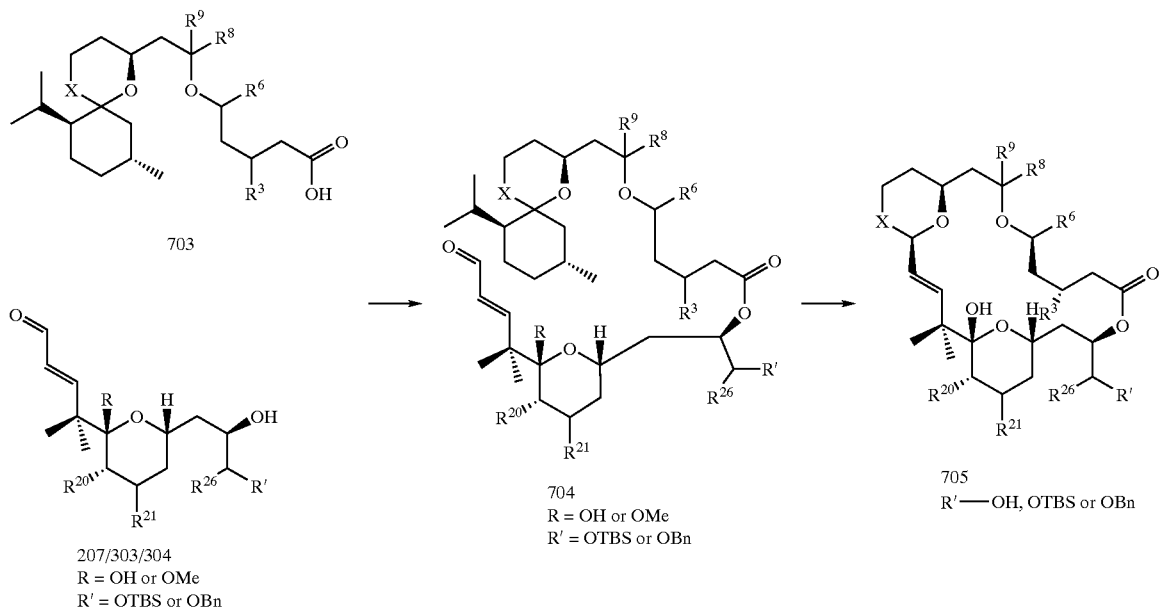
Reaction Scheme 8 illustrates synthesis of the Compounds of Formula IV, particularly where $R^{26}$ is methyl, the C26 des-methyl analogues of Formula IV being obtained by like synthesis.
Reaction Scheme 8
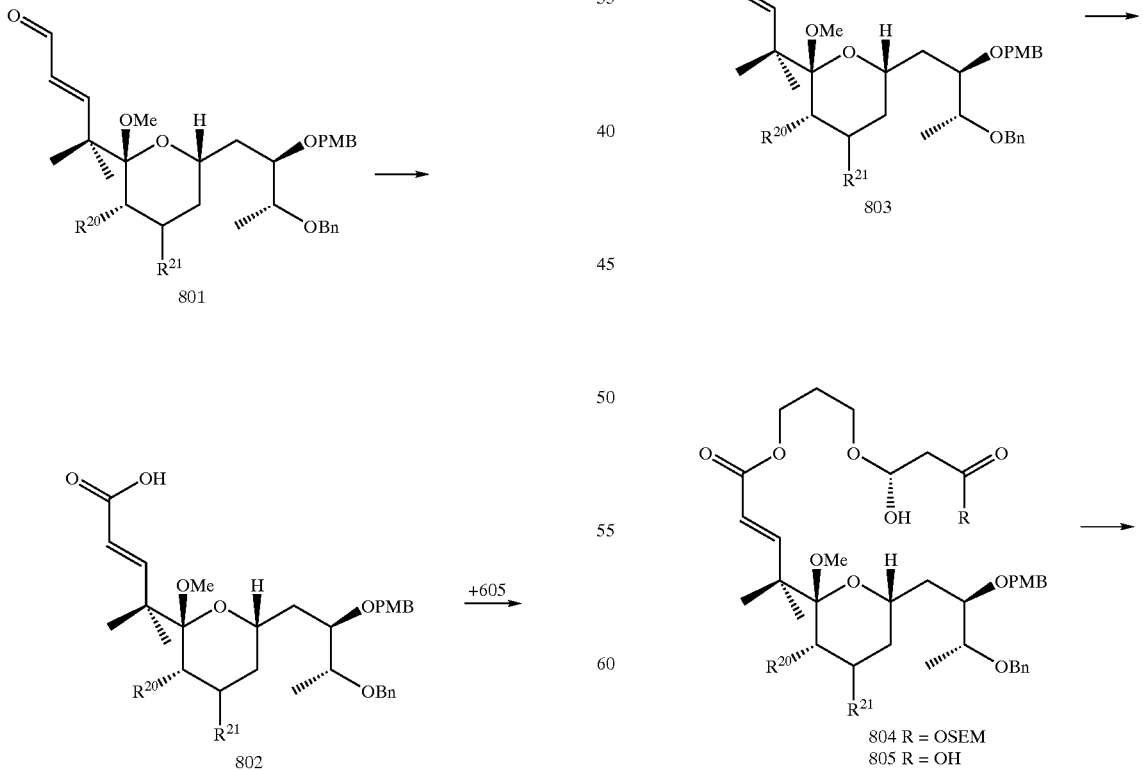

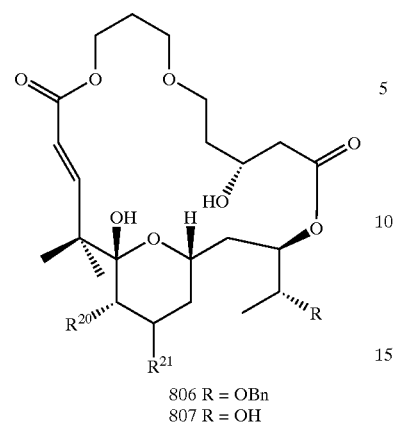
806 R = OBn
807 R = OH
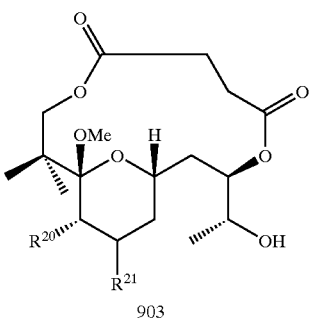
903
Reaction Schemes 10 and 11 illustrate the synthesis of compounds of the invention that are further derivatized at the C20 position, as discussed in Examples 4B, 4C and 4D.
Reaction Scheme 9 illustrates synthesis of the Compounds of Formula V.
Reaction Scheme 9
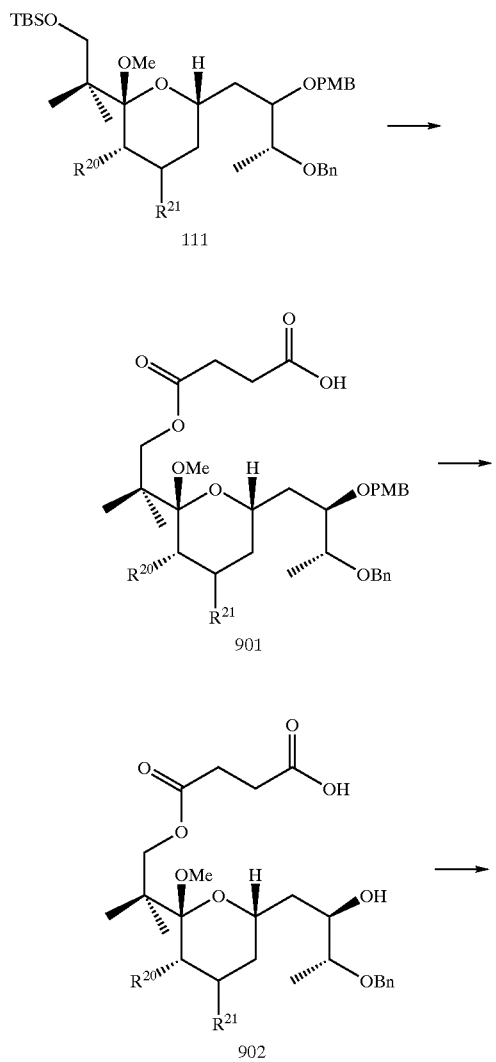
111
901
902
Reaction Scheme 10
(9)
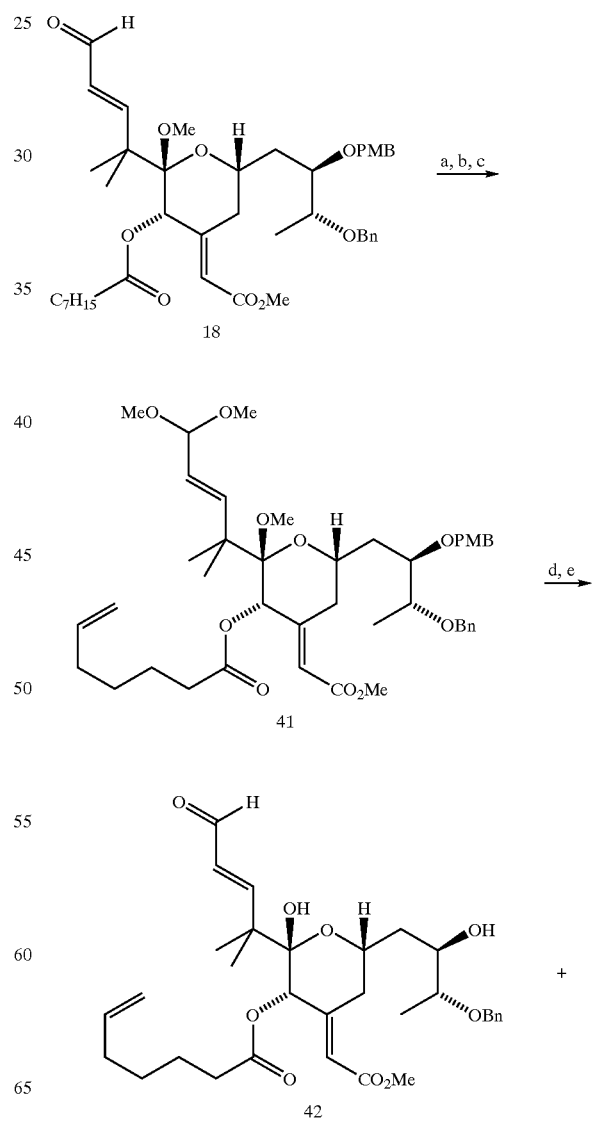
18
41
42

31
-continued

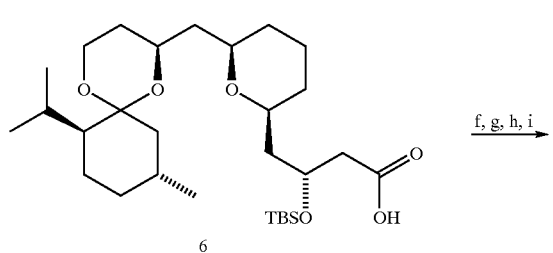

6

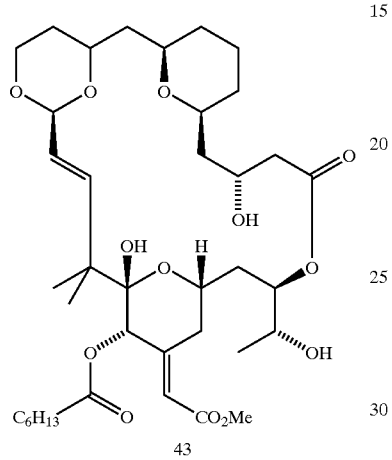

43 a) CH(OMe)₃, PPTS, MeOH; b) K₂CO₃, MeOH; c) heptenoic acid, Et₃N, DMAP, Yamaguchi's reagent, CH₂Cl₂ (84% for three steps); d) DDQ, CH₂Cl₂/H₂O (85%); e) 48% HF, CH₃CN/H₂O (80% yield); f) Yamaguchi's reagent, Et₃N, DMAP (80%); g) HF-Pyridine, THF (68%); h) Amberlyst 15, CH₂Cl₂ (70%); i) Pd(OH)₂, EtOAc, H₂, 1 atm (63% yield)

Reaction Scheme 11

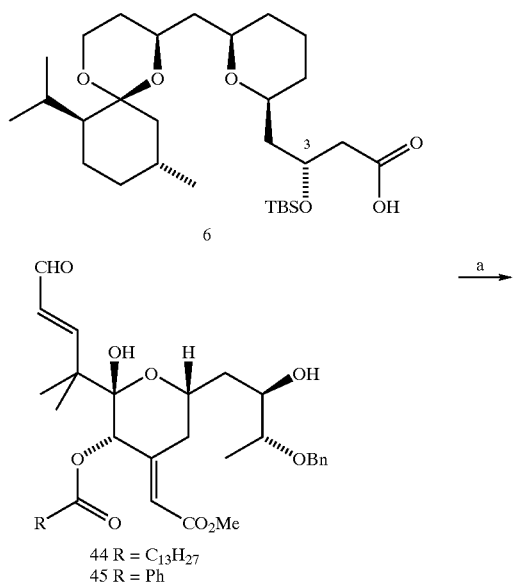

32
-continued

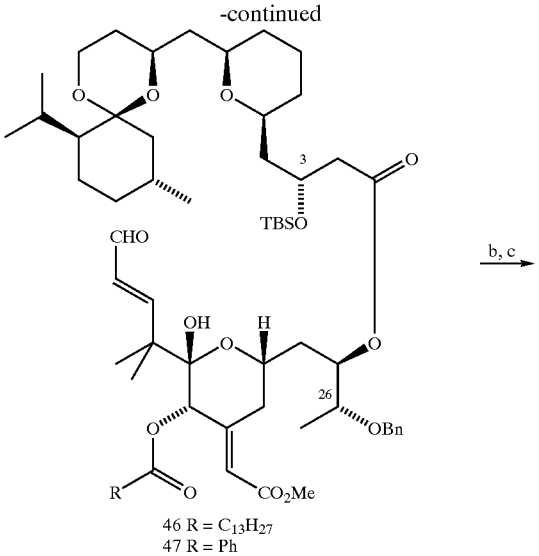

46 R = C₁₃H₂₇
47 R = Ph

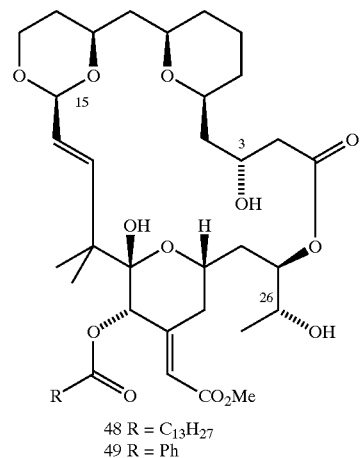

48 R = C₁₃H₂₇
49 R = Ph (a) 2, 4, 6-trichlorobenzoylchloride, Et₃N, DMAP then 44 or 45, CH₂Cl₂, rt, 90% for R = C₁₃H₂₇, 89% for R = Ph. (b) HF•pyridine, THF, rt, 83% for R = C₁₃H₂₇, 80% for R = Ph. (c) Pd(OH)₂, H₂, EtOAc, 1 atm, 97% for 48, 63% for 49.

Starting Materials. Conveniently, compounds of the invention can be prepared from starting materials that are commercially available or may be readily prepared by those skilled in the art using commonly employed synthetic methodology.

Reaction Scheme 1 illustrates a method for forming a synthon designated herein as 111 which is useful for providing the recognition domain in compounds of the invention, for example as detailed in Example 1. 6-(Tert-butyldimethylsilylhydroxy)-5-dimethylhexane-2,4-dione (101, Example 1B) is stirred with 2 equivalents of LDA (lithium diisopropylamine) in THF (tetrahydrofuran), followed by addition of 0.9 equivalents of 3R-p-methoxybenzyl-4R-benzylhydroxypentane-1-a1 (102, Example 1A) to afford diasteriomeric aldol mixture 103 after suitable purification. To 103 is then added a catalytic amount of p-methylphenylsulfonic acid (p-TsOH) with stirring at room temperature followed by base quenching to produce pyranone condensation product 104 as a mixture of α and β-isomers at C23 (104a and 104b). The β-isomer (104a) is separated from the α-isomer and is reacted with NaBH4 in the presence of $CeCl_3.7H_2O$, followed by quenching with aqueous brine to form an allylic alcohol (not shown) that can then be epoxidized with m-chloroperbenzoic acid (mCPBA) in 2:1 $CH_2Cl_2$:MeOH containing sodium bicarbonate as a buffer to yield a C19-methoxylated C20, C21 syn-diol 105. Selective benzoylation of the C21 equatorial alcohol with benzoyl chloride to afford C21 monobenzoate (not shown), followed by oxidation of the C20 hydroxyl with Dess-Martin periodinane (1,1,1-triacetoxy-1,1-dihydro-1,2-benziodoxol-3(1H)-one) at room temperature affords the corresponding 20-keto-21-benzoate product 106. Treatment of 106 with $SMI_2$ (2 equiv) yields a ketone 107 selectively deoxygenated at C21. Next, ketone 107 is reacted with LDA and $OHCCO_2CH_3$ in THF at −78° C. to afford aldol mixture 108. After purification, 108 is reacted with methanesulfonylchloride in $CH_2Cl_2$ containing triethylamine, followed by reaction with DBU (1,8-diazabicyclo[5.4.0]undec-7-ene) in THF to effect an aldol condensation and elimination of water, to yield an α,β-unsaturated methyl ester (enone 109) with an E-stereoconfiguration. Treatment of enone 109 with $NaBH_4$ in the presence of $CeCl_3.7H_2O$ produces exclusively the C20 axial alcohol 110. This product can then be esterified at C20, with octanoic acid for example, to yield the desired synthon 111.

It will be appreciated how the foregoing procedures can be exploited or modified to produce recognition region synthons having different substituents. For example, compounds where $R^{21}$ contains a C35 ester group having a Z-configuration are produced during formation of intermediate 109 (Example 1C) and can be isolated by chromatography. Similarly, other ester groups can be introduced at C35 by replacing the $OHCCO_2CH_3$ reactant used to form 108 above with an appropriately substituted compound of the form $OHCCO_2R'$, in which R' is other than methyl.

In addition, as detailed below, other substituents can be introduced in synthon 111 to generate substituent $R^{20}$ at C20 by substituting any of a variety of carboxylic acids for the octanoic acid reacted with axial alcohol 110 (as in the last step of Example 1C), including other saturated, unsaturated, aryl, and carboxylic acids. In synthesizing the compounds of the invention where $R^{20}$ has been varied, the substituent (e.g., a desired C20 ester substituent) can be introduced into a recognition region synthon prior to condensing the recognition region synthon with a linker synthon using the procedures described in Example 4. In Example 4A, the C20 octanoate substituent in synthon 111 can be replaced with an acetyl group by first protecting the base labile aldehyde group using trimethyl orthoformate to form the dimethyl acetal. The C20 octanoate ester can then be cleaved using a basic solution, such as $K_2CO_3$ in methanol, to afford the free C20 alcohol, followed by reaction with an activated form of acetic acid, such as acetic anhydride or acetyl chloride, to obtain the C20 acetate product. The product can then be deprotected at the C15 aldehyde, C19 oxygen, and C25 oxygen using benzoquinone compound DDQ (to remove the p-methoxybenzyl group and cleave the dimethyl acetal) followed by aqueous HF (demethylation at C19) to afford the corresponding C19 alcohol. This product can then be condensed with an appropriately substituted linker synthon to produce a desired bryostatin analogue, such as analogue 702.1, as detailed in Example 4A.

The protected alcohol precursor to many of the C26-desmethyl bryostatin analogues of the invention (the compounds of Formula I where $R^{26}$ is H) can be made as illustrated in Reaction Scheme 2. Di(benzyl ether) 111 can be hydrogenated over Pearlman's catalyst to produce the corresponding C25,C26 diol 201. Treatment of the diol with lead tetraacetate yields the corresponding C25 aldehyde (not shown), with the release of C26 and C27. Reaction of the aldehyde with $Cp_2Ti(Cl)CH_2Al(CH_3)_2$ (Tebbe's reagent) yields C25,C26 olefin 202. Alternatively, sodium periodate can be used in place of lead tetraacetate.

Treatment of olefin 202 with HF/pyridine is effective to remove the silyl protecting group, followed by treatment with Dess-Martin periodinane (supra) to oxidize the C17 alcohol to an aldehyde group, affording aldehyde 203. The C25,C26 olefin of 203 can be converted to C25,C26 diol 204 by reaction with chiral dihydroxylating reagent (DHQD)$_2$AQN in the presence of $K_3Fe(CN)_6$, $K_2CO_3$ and $K_2OsO_2(OH)_4$ in t-butanol. Product 204 is obtained as a 2:1 (α:β) mixture of 25-hydroxy diastereomers. The α-diastereomer can be removed later in the synthesis. Treatment of 204 with triethylsilyl chloride yields protected diol 205, which can be employed in the synthesis of the compounds of Formula V.

Addition of backbone atoms corresponding to C15 and C16 of the bryostatin backbone to 205 can be accomplished in four steps. First, the C17 aldehyde is allylated with allyl diethylborane. The reaction is quenched with saturated sodium bicarbonate to yield the desired C17 allyl adduct. The C17 hydroxyl group can then be acylated with acetic anhydride in the presence of triethylamine and 4-dimethylaminopyridine (DMAP), to afford a diastereomeric mixture of homoallylic C17 acetates. This product mixture can be oxidized using N-methylmorpholine N-oxide and osmium tetraoxide, followed by neutralization with sodium bicarbonate. After extraction, the residue is reacted with lead tetraacetate, followed by addition of DBU to cause elimination of the acetate group, yielding enal 206.

The C25 hydroxyl group of 206 can be unmasked in preparation for closure of the macrocycle as follows. First, enal 206 is treated with aqueous hydrofluoric acid to provide a crude diol intermediate in which the C19 methoxy group is converted to a free hydroxyl. Next, the diol product is reacted with tert-butyldimethylsilyl chloride (TBSCl) in the presence of imidazole to produce alcohol 207 containing a C25 hydroxyl group and C26 OTBS group as a 2:1 (β:α) mixture of C25 diastereomers. Silica gel chromatography can be used to resolve the diastereomers, affording the β diastereomer in 50–60% yield.

The protected alcohol precursor to many of the C26-methyl bryostatin analogues of the invention (Formula I where $R^{26}$ is methyl) can be made as illustrated in Reaction Scheme 3, via methods analogous to the preparations for 205 and 206. Deprotection and acylation of formula 111 may be accomplished, for example, by following the procedures described in Wender et al., (1998a).

Linker synthons for the compounds of Formula II (where X is a heteroatom) can be prepared, for example, as illustrated with reference to Reaction Scheme 4, and later described in Examples 2A and 2B. These compounds contain two rings that are analogous to the A and B rings of bryostatin, but lack the naturally occurring substituents at C7, C8, C9, and C13. The presence of a heteroatom, such as an oxygen, sulfur or nitrogen atom (the lone electron pair of which is stabilized) in place of C14 does not adversely affect activity of the end product, but is required for transacetylization in the later synthetic steps. The compounds of formulae 406 and 408 differ in that 402 provides a protecting group precursor for a hydroxyl group attached to C3, whereas 406 does not provide for a hydroxyl at C3.

The linker synthons for the compounds of Formula III (in which X is a heteroatom), which contain a B-ring-like structure but lack an A-ring, are prepared, for example, as illustrated with reference to Reaction Schemes 5A through 5C. Examples 2C and 2D describe methods for preparing synthons 504 and 508. In both examples, $R^8$ is a tert butyl group attached to C9. However, with reference to the preparation of 505, the t-BuLi reactant can be replaced by R'Li to generate the corresponding linker synthons of 508 where $R^8$ is R'. 504 additionally contains a TMS protecting group for synthesis of the compounds where $R^9$ is a hydroxyl attached to C9, rather than hydrogen. Also, both synthons contain a TBS protecting group for the compounds where $R^3$ is a hydroxyl group attached to C3. Example 2E describes the corresponding method for making synthon 507, which is unsubstituted at C9. Example 2G describes a method for preparing linker synthons in which C5 is provided as an ester carbonyl. In addition, the synthons in this Example contain an $R^6$ substituent that is preferably a saturated or unsaturated substituent containing 1 to 20 carbon atoms and optionally (1) one or more oxygen atoms and (2) optionally one or more nitrogen atoms. In synthon 514 in Example 2G, $R^8$ is —$C(CH_3)_2CH_2OC(=O)C_{13}H_{27}$. However, other $R^6$ substituents can be introduced by suitable modification of the procedure as will be evident to one of ordinary skill in the chemical arts.

Synthesis of a completely acyclic linker synthon 606 (where neither an A- nor a B-ring-like structure is present) is described with reference to Reaction Scheme 6 and in Example 2F.

As illustrated with reference to Reaction Scheme 7A, and further described in Example 3A, an alcohol such as 207, 303 or 304 is reacted with an acid such as 406 or 408 in a two step process to form the desired macrocyclic structure. After in situ conversion of the acid (408) to a mixed anhydride, the alcohol (207) is added to form ester 701. The ketal portion of 408 is then joined (in a process referred to as macrotranacetylization) to C15 of 701 by adding 70% HF/pyridine hydrofluoric acid to catalyze cleavage of the menthone ketal, cleavage of the TBS ethers at C3 and C26, and formation of a new ketal between the C15 aldehyde group and the linker diol moiety generated by release of the menthone (where X is oxygen), to afford desired analogue of Formula II where X is a heteroatom and $R^{26}$ is H (starting with alcohol 207) or methyl (starting with 303 or 304), i.e., compound of formula 702. This last reaction is also effective to set the stereocenter at C15 to a thermodynamically preferred configuration. The analogous synthesis of compounds of Formula III (where X is a heteroatom), first forming the ether bond between C1 and C25, is illustrated with reference to Reaction Scheme 7B (where formula 703 corresponds to any of formulae 504, 507, 508 or 513) and further described in Example 3C.

As illustrated with reference to Reaction Scheme 8, and further described in Example 3B, the compounds of Formula IV (such as formula 807) can be made from pharmacophoric synthon 801 and linker synthon 606 from Example 2F.

Reaction Scheme 9 illustrates synthesis of the compounds of Formula V, e.g., as further described in Example 3D, from synthon 111 and an activated dicarboxylic acid (succinic anhydride) to give formula 903.

Although the bryostatin analogues produced in Examples 3B, 3C and 3D all contain a C27 methyl group, analogous C26 desmethyl analogues can be readily synthesized using an appropriate C26 desmethyl synthon, such as C26 desmethyl synthon 207 described in Example 1C. Compounds of the invention having a naturally occurring bryostatin backbone (e.g., including a naturally occuring linker region), but lacking the C27 methyl group, can also be prepared by adapting synthetic protocols published by Kageyama et al. (1990) and Evans et al. (1998), which are incorporated herein by reference. In brief, the published methods are modified by utilizing synthons in which the C27 methyl group has been omitted, to afford the desired C26-desmethyl analogues.

As illustrated with reference to Reaction Scheme 10, synthesis of a C20 heptanoate ester 43 is described in Example 4B, using a similar reaction scheme to that employed in Example 4A, except that heptenoic acid in the presence of triethylamine, DMAP, and Yamaguchi's agent is used in place of acetic anhydride. Yamaguchi's reagent is again employed in step f to activate the COOH group of formula 6, followed by removal of the TBS group in step g, hydrolysis of the menthone and transacetylization in step h, and saturation of the double bond upon removal of the benzyl group by hydrogenolysis in step i. Synthesis of a C20 myristate ester analogue 48 (14 carbon atom chain) is illustrated with reference to Reaction Scheme 11 and described in Example 4C. Reaction Scheme 11 and Example 4D describes synthesis of a bryostatin analogue containing an aryl ester group (benzoate) at C20, by suitable adaptation of the procedure in Example 1C for making compound 207. It will be appreciated how these procedures can be modified to introduce other C20 esters by substituting the starting materials necessary to produce the desired products. In particular, C26 des-methyl analogues can be made using an appropriate C26 des-methyl synthon, such as 207 noted above.

The lactam analogues of the invention are obtained by converting the C25 hydroxyl group (e.g., of formula 207) to an amine under Mitsonobu conditions, after first protecting the aldehyde (and the C19 hydroxyl group in the corresponding compounds in Reaction Schemes 10 and 11) followed by formation of the macrocycle and de-protection under conditions analogous to those employed for the lactone analogues, as will be apparent to one skilled in the art.

The C26 des-methyl bryostatin homologues of the invention can be obtained by substituting homologous des-methyl starting materials for the starting materials employed in published bryostatin syntheses (e.g., Masamune 1988a, 1988b, Evans et al. 1998, Kageyama et al. 1990). For example, in the total synthesis of bryostatin 7, Serine is substituted for threonine in a Masamune's C17–C26 southern bryostatin synthesis to yield the corresponding C26 des-methyl sulfone. Other synthetic methodology will be apparent to those skilled in the art given the objective of providing such C26 des-methyl bryostatin homologues.

Preferred Processes and Last Steps

A C19,C26 hydroxyl-protected, C26 des-methyl bryostatin recognition domaine precursor and an optionally protected linker synthon are esterified, macrotransacetylated and de-protected to give the corresponding C26 des-methyl bryostatin analogue.

A bryostatin analogue precursor having the C26 hydroxyl substituted by a protecting group (particularly OBn) is reduced to give the corresponding compound of Formula I.

Serine is substituted for threonine in a Masamune's C17–C26 southern bryostatin synthesis to yield the corresponding C26 des-methyl sulfone, which in turn is employed in synthesis of a C26 des-methyl bryostatin homologue.

A compound of Formula I–VI is contacted with a pharmaceutically acceptable acid to form the corresponding acid addition salt.

A pharmaceutically acceptable acid addition salt of Formula I–VI is contacted with a base to form the corresponding compound of Formula I–VI.

Preferred Compounds

The following substituents, compounds and groups of compounds are presently preferred.

In the compounds of Formulae I–V, especially those of Formulae II–V, it is preferred that $R^{26}$ is H. Most preferred are the compounds of Formula II where $R^{26}$ is H, and of those where X is oxygen. Of the compounds where $R^{26}$ is H, additionally preferred are those compounds where $R^{20}$ is $O_2CR'$, especially where R' is alkyl (preferably about $C_7$–$C_{20}$ alkyl), alkenyl (preferably about $C_7$–$C_{20}$ alkenyl such as $CH_3$—$CH_2$—$CH_2$—CH=CH—CH=CH—) or aryl (preferably phenyl or naphthyl). Another group of preferred compounds where $R^{26}$ is H are those where $R^{21}$ is =$CR^aR^b$ (especially where one of $R^a$ or $R^b$ is H and the other is $CO_2R'$, and preferably where R'is $C_1$–$C_{10}$ alkyl, most preferably lower alkyl such as methyl).

The compounds of Formulae I–V, especially II–V, are preferred where $R^{20}$ is $O_2CR'$ and R' is alkyl (preferably about $C_7$–$C_{20}$ alkyl), alkenyl (preferably about $C_7$–$C_{20}$ alkenyl such as $CH_3$—$CH_2$—$CH_2$—CH=CH—CH=CH—) or aryl (preferably phenyl or naphthyl). Particularly preferred are those compounds where $R^{20}$ is $O_2CR'$ and $R^{21}$ is =$CR^aR^b$ (especially where one of $R^a$ or $R^b$ is H and the other is $CO_2R'$, and preferably where R' is $C_1$–$C_{10}$ alkyl, most preferably lower alkyl such as methyl).

The compounds of Formulae I–V, especially II–V, are preferred where $R^{21}$ is =$CR^aR^b$ (especially where one of $R^a$ or $R^b$ is H and the other is $CO_2R'$, and preferably where R' is $C_1$–$C_{10}$ alkyl, most preferably lower alkyl such as methyl).

Of the compounds according to Formula I, it is preferred that L be a group having from about 6 to about 14 carbon atoms.

Of the compounds according to Formulae II or III, it is preferred that X is oxygen.

Of the compounds according to Formulae II–IV, it is preferred that $R^3$ is OH, and especially preferred that X is oxygen in the case of Formulae II and III.

Of the compounds according to Formula II, it is preferred that $R^{20}$ is $O_2CR'$ where R' is alkyl (preferably about $C_7$–$C_{20}$ alkyl), alkenyl (preferably about $C_7$–$C_{20}$ alkenyl such as $CH_3$—$CH_2$—$CH_2$—CH=CH—CH=CH—) or aryl (preferably phenyl or naphthyl). Of these, further preferred are the compounds where $R^{21}$ is =$CR^aR^b$ (especially where one of $R^a$ or $R^b$ is H and the other is $CO_2R'$, and preferably where R' is $C_1$–$C_{10}$ alkyl, most preferably lower alkyl such as methyl).

Of the compounds according to Formula III, it is preferred that $R^9$ is H. It is further preferred that $R^8$ is —$(CH_2)_nO(O)CR'$, particularly where R' is alkyl, $R^6$ optionally being =O.

Further preferred are those compounds that combine various of the above-mentioned features. The single isomers highlighted in the reaction schemes and examples are also preferred.

Presently, most preferred is the compound of Formula II where X is oxygen, $R^3$ is OH, $R^{20}$ is —O—CO—$C_7H_{15}$, $R^{21}$ is =CH—$CO_2$Me and $R^{26}$ is H.

Utility, Testing and Administration

General Utility

The compounds of the present invention are useful as bryostatin-like therapeutic agents, and in pharmaceutical formulations and methods of treatment employing the same. Other compounds of the invention are useful a precursors in the synthesis of such agents. Importantly, in many cases, the compounds of the present invention can be readily synthesized on a large scale, and thus can be made readily available for commercial purposes as compared to the low yields and environmental problems inherent in the isolation of bryostatins from natural sources.

In one aspect, the compounds of the invention find use as anticancer agents in mammalian subjects. For example, representative cancer conditions and cell types against which the compounds of the invention may be useful include melanoma, myeloma, chronic lymphocytic leukemia (CLL), AIDS-related lymphoma, non-Hodgkin's lymphoma, colorectal cancer, renal cancer, prostate cancer, cancers of the head, neck, stomach, esophagus, anus, or cervix, ovarian cancer, breast cancer, peritoneal cancer, and non-small cell lung cancer. The compounds appear to operate by a mechanism distinct from the mechanisms of other anticancer compounds, and thus can be used synergistically in combination with other anticancer drugs and therapies to treat cancers via a multimechanistic approach. The compounds of the invention exhibit potencies comparable to or better than previous bryostatins against many human cancer types.

In another aspect, the compounds of the invention can be used to strengthen the immune system of a mammalian subject, wherein a compound of the invention is administered to the subject in an amount effective to increase one or more components of the immune system. For example, strengthening of the immune system can be evidenced by increased levels of T cells, antibody-producing cells, tumor necrosis factors, interleukins, interferons, and the like. Effective dosages may be comparable to those for anticancer uses, and can be optimized with the aid of various immune response assay protocols such as are known in the art (e.g., see Kraft, 1996; Lind, 1993; U.S. Pat. No. 5,358,711, all incorporated herein by reference). The compound can be administered prophyllactically, e.g., for subjects who are about to undergo anticancer therapies, as well as therapeutically, e.g., for subjects suffering from microbial infection, bum victims, subjects with diabetes, anemia, radiation treatment, or anticancer chemotherapy. The immunostimulatory activity of the compounds of the present invention is unusual among anticancer compounds and provides a dual benefit for anticancer applications. First, the immunostimulatory activity allows the compounds of the invention to be used in greater doses and for longer periods of time than would be possible for compounds of similar anticancer activity but lacking immunostimulatory activity. Second, the compounds of the present invention can offset the immunosuppressive effects of other drugs or treatment regimens when used in combination therapies. Additional features of the invention can be further understood from the following illustrative examples which are not intended to limit the scope of the invention in any way.

Testing

In practicing various aspects of the present invention, compounds in accordance with the invention can be tested for a biological activity of interest using any assay protocol that is predictive of activity in vivo. For example, a variety of convenient assay protocols are available that are generally predictive of anticancer activity in vivo.

In one approach, anticancer activity of compounds of the invention can be assessed using the protein kinase C assay detailed in Example 5. In this assay, $K_i$ values are determined for analogues based on competition with radiolabeled phorbol 12,13-dibutyrate for binding to a mixture of PKC isoenzymes. PKC enzymes are implicated in a variety of cellular responses which may be involved in the activity of the bryostatins.

Example 6 describes another protein kinase C assay which can be used to assess the binding affinities of compounds of the invention for binding to the C1B domain of PKCδ. Although all PKC isozymes are upregulated immediately after administration of bryostatin or tumor promoting phorbol esters followed by an extended down-regulation period, PKCδ appears to be protected against down regulation by bryostatin 1. Overexpression of PKCδ inhibits tumor cell growth and induces cellular apoptosis, whereas depleting cells of PKCδ can cause tumor promotion. Accordingly, this assay provides useful binding data for assessing potential anticancer activity.

Another useful method for assessing anticancer activities of compounds of the invention involves the multiple-human cancer cell line screening assays run by the National Cancer Institute (e.g., Boyd, 1989). This screening panel, which involves approximately 60 different human cancer cell lines, is a useful indicator of in vivo antitumor activity for a broad variety of tumor types (Grever et al., 1992, Monks et al., 1991), such as leukemia, non-small cell lung, colon, central nervous system (CNS), melanoma, ovarian, renal, prostate, and breast cancers. Antitumor activites can be expressed in terms of $ED_{50}$ (or $GI_{50}$), where $ED_{50}$ is the molar concentration of compound effective to reduce cell growth by 50%. Compounds with lower $ED_{50}$ values tend to have greater anticancer activities than compounds with higher $ED_{50}$ values. Example 7 describes a P388 murine lymphocytic leukemia cell assay which measures the ability of compounds of the invention to inhibit cellular growth.

Upon the confirmation of a compounds potential activity in the above in vitro assays, further evaluation is typically conducted in vivo in laboratory animals, for example, measuring reduction of lung nodule metastases in mice with B16 melanoma (e.g., Schuchter et al, 1991). The efficacy of drug combination chemotherapy can be evaluated, for example, using the human B-CLL xenograft model in mice (e.g., Mohammad et al, 1996). Ultimately, the safety and efficacy of compounds of the invention are evaluated in human clinical trials.

Experiments conducted in support of the present invention demonstrate that compounds of the present invention exhibit high potencies in several anticancer assays, as summarized in the Examples.

Administration

The invention includes a method of inhibiting growth, or proliferation, of a cancer cell, or enhancing the effectiveness of other drugs. In the method, a cancer cell is contacted with a bryostatin analogue compound in accordance with the invention in an amount effective to inhibit growth or proliferation of the cell. In a broader aspect, the invention includes a method of treating cancer in a mammalian subject, especially humans. In the method, a bryostatin analogue compound in accordance with the invention is administered to the subject in an amount effective to inhibit growth of the cancer in the patient. Similarly, in the immune modulation methods of the invention, a compound of the invention is administered to a subject in need thereof, in an amount herapeutically effective for bolstering of the immune system predisposed toward apoptosis.

Compositions and methods of the present invention have particular utility in the area of human and veterinary therapeutics. Generally, administered dosages will be effective to deliver picomolar to micromolar concentrations of the therapeutic composition to the target site. Typically, nanomolar to micromolar concentration at the target site should be adequate for many applications. Appropriate dosages and concentrations will depend on factors such as the particular compound or compounds being administered, the site of intended delivery, and the route of administration, all of which can be derived empirically according to methods well known in the art.

Administration of compounds of the invention in an appropriate pharmaceutical form can be carried out by any appropriate mode of administration. Thus, administration can be, for example, intravenous, topical, subcutaneous, transocular transcutaneous, intramuscular, oral, intra-joint, parenteral, peritoneal, intranasal, or by inhalation. The formulations may take the form of solid, semi-solid, lyophilized powder, or liquid dosage forms, such as, for example, tablets, pills, capsules, powders, sustained-release formulations, solutions, suspensions, emulsions, suppositories, retention enemas, creams, ointments, lotions, aerosols, and the like. In one embodiment, the formulation has a unit dosage form suitable for administration of a precise dose.

Pharmaceutical compositions of the invention typically include a conventional pharmaceutical carrier or excipient and may additionally include other medicinal agents, carriers, adjuvants, antioxidants, and the like. In one embodiment, the composition may comprise from about 1% to about 75% by weight of one or more compounds of the invention, with the remainder consisting of suitable pharmaceutical excipients. For oral administration, such excipients include pharmaceutical grades of mannitol, lactose, starch, magnesium stearate, sodium saccharine, talcum, cellulose, glucose, gelatin, sucrose, magnesium carbonate, for example. Appropriate excipients can be tailored to the particular composition and route of administration by methods well known in the art, e.g., (Gennaro, 1990). Additional guidance for formulations and methods of administration can be found in patent references concerning previously known bryostatins, such as U.S. Pat. Nos. 4,560,774 and 4,611,066 to Pettit et al., which are incorporated herein by reference.

Usually, for oral administration, the compositions will take the form of a pill, tablet or capsule. Thus the composition will contain, along with active drug, a diluent such as lactose, sucrose, dicalcium phosphate, and/or other material, a disintegrant such as starch or derivatives thereof; a lubricant such as magnesium stearate and the like; and a binder such a starch, gum acacia, polyvinylpyrrolidone, gelatin, cellulose and/or derivatives thereof.

The compounds of the invention may also be formulated into a suppository comprising, for example, about 0.5% to about 50% of a compound of the invention, disposed in a polyethylene glycol (PEG) carrier (e.g., PEG 1000 [96%] and PEG 4000 [4%]).

Liquid compositions can be prepared by dissolving or dispersing compound (e.g., from about 0.5% to about 20% of final volume), and optional pharmaceutical adjuvants in a carrier, such as, for example, aqueous saline, aqueous dextrose, glycerol, ethanol and the like, to form a solution or suspension. Useful vehicles also include polyoxyethylene sorbitan fatty acid monoesters, such as TWEEN™ 80, and polyethoxylated castor oils, such as Cremophor EL™ available from BASF (Wyandotte, Md.), as discussed in PCT Publ. No. WO 97/23208 (which is incorporated herein by reference), which can be diluted into conventional saline solutions for intravenous administration. Such liquid compositions are useful for intravenous administration. One such formulation is PET diluent which is a 60/30/10 v/v/v mixture of PEG 400, dehydrated ethanol, and TWEEN™-80. Liquid compositions may also be formulated as retention enemas.

The compounds of the invention may also be formulated as liposomes using liposome preparation methods known in the art. Preferably, the liposomes are formulated either as small unilamellar vesicles or as larger vesicles.

If desired, the composition to be administered may also contain minor amounts of non-toxic auxiliary substances such as wetting or emulsifying agents, pH buffering agents, such as, for example, sodium acetate, sorbitan monolaurate, triethanolamine oleate, and antioxidants.

For topical administration, the composition is administered in any suitable format, such as a lotion or a transdermal patch. For delivery by inhalation, the composition can be delivered as a dry powder (e.g., Inhale Therapeutics) or in liquid form via a nebulizer.

Methods for preparing such dosage forms are known or will be apparent to those skilled in the art; for example, see Gennaro (1990). The composition to be administered will, in any event, contain a quantity of one or more compounds of the invention in a pharmaceutically effective amount for relief of the condition being treated.

The compounds of the invention may also be introduced in a controlled-release form, for long-term delivery of drug to a selected site over a period of several days or weeks. In this case, the compound of the invention is incorporated into an implantation device or matrix for delayed or controlled release from the device.

The compounds can be incorporated in a biodegradable material, such as a biodegradable molded article or sponge. Exemplary biodegradable materials include matrices of collagen, polylactic acid-polyglycolic acid, and the like. In preparing bryostatin compounds in matrix form, the compounds may be mixed with matrix precursor, which is then crosslinked by covalent or non-covalent means to form the desired matrix. Alternatively, the compound can be diffused into a preformed matrix. Examples of suitable materials for use as polymeric delivery systems have been described e.g., Aprahamian, 1986; Emmanuel, 1987; Friendenstein, 1982; and Uchida, 1987.

Generally, compounds of the invention are administered in a therapeutically effective amount, i.e., a dosage sufficient to effect treatment, which may vary depending on the individual and condition being treated. Typically, a therapeutically effective daily dose is from 0.1 µg/kg to 100 mg/kg of body weight per day of drug. Given the high therapeutic activities of the compounds of the invention, daily dosages of from about 1 µg/kg and about 1 mg/kg of body weight may be adequate, although dosages greater than or less than this range can also be used.

It will be appreciated that the compounds of the invention may be administered in combination (i.e., together in the same formulation or in separate formulations administered by the same or different routes) with any other anti-cancer regimen deemed appropriate for the patient. For example, the compounds of the invention may be used in combination with other anticancer drugs such as vincristine, cisplatin, ara-C, taxanes, edatrexate, L-buthionine sulfoxide, tiazofurin, gallium nitrate, doxorubicin, etoposide, podophyllotoxins, cyclophosphamide, camptothecins, dolastatin, and auristatin-PE, for example, and may also be used in combination with radiation therapy. In a preferred embodiment, the combination therapy entails co-administration of an agent selected from: ara-C, taxol, cisplatin and vincristine.

EXAMPLES

General Techniques. Unless noted otherwise, materials were obtained from commercially available sources and used without further purification. Tetrahydrofuran (THF) and diethyl ether ($Et_2O$) were distilled from sodium benzophenone ketyl under a nitrogen atmosphere. Benzene, dichloromethane ($CH_2Cl_2$), acetonitrile ($CH_3CN$), triethylamine ($Et_3N$) and pyridine were distilled from calcium hydride under a nitrogen atmosphere. Chloroform ($CHCl_3$), carbon tetrachloride ($CCl_4$) and deuterated NMR solvents were dried over 1/16" bead 4 Å molecular sieves.

All operations involving moisture-sensitive materials were conducted in oven- and/or flame-dried glassware under an atmosphere of anhydrous nitrogen. Hygroscopic solvents and liquid reagents were transferred using dry Gastight™ syringes or cannulating needles. In cases where rigorous exclusion of dissolved oxygen was required, solvents were degassed via consecutive freeze, pump, thaw cycles or inert gas purge.

Nuclear magnetic resonance (NMR) spectra were recorded on either a Varian UNITY INOVA-500, XL-400 or Gemini-300 magnetic resonance spectrometer. $^1H$ chemical shifts are given in parts per million ($\delta$) downfield from tetramethylsilane (TMS) using the residual solvent signal ($CHCl_3=\delta7.27$, benzene=$\delta7.15$, acetone=$\delta2.04$) as internal standard. Proton ($^1H$) NMR information is tabulated in the following format: number of protons, multiplicity (s, singlet; d, doublet; t, triplet; q, quartet; sept, septet, m, multiplet), coupling constant(s) (J) in hertz and, in cases where mixtures are present, assignment as the major or minor isomer, if possible. The prefix app is occasionally applied in cases where the true signal multiplicity was unresolved and br indicates the signal in question was broadened. Proton decoupled $^{13}C$ NMR spectra are reported in ppm ($\delta$) relative to residual $CHCl_3$ ($\delta77.25$) unless noted otherwise.

Infrared spectra were recorded on a Perkin-Elmer 1600 series FTIR using samples prepared as thin films between salt plates. High-resolution mass spectra (HRMS) were recorded at the NIH regional mass spectrometry facility at the University of California, San Francisco. Fast Atom Bombardment (FAB) high-resolution mass spectra were recorded at the University of California, Riverside. Combustion analyses were performed by Desert Analytics, Tucson, Ariz., 85719 and optical rotations were measured on a Jasco DIP-1000 digital polarimeter.

Flash chromatography was performed using E. Merck silica gel 60 (240–400 mesh) according to the protocol of Still et al. (1978). Thin layer chromatography was performed using precoated plates purchased from E. Merck (silica gel 60 PF254, 0.25 mm) that were visualized using either a p-anisaldehyde or Ce(IV) stain.

For binding and cell-inhibition studies, dilutions of bryostatin and bryostatin analogues were performed in glass rather than plastic, to avoid problems associated with adsorption to plastic.

Example 1

Exemplary Precursors

1A. Protected Diol Aldehyde 102

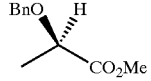
A1

Benzyl bromide (7.0 mL, 57.7 mmol) and freshly prepared Ag$_2$O (11.0 g, 48.1 mmol) were added successively to an Et$_2$O (150 mL) solution of R-(+)-methyl lactate (5.0 g, 48.1 mmol) at rt (room temperature). The resulting suspension was brought to reflux and stirred for 2 h. The reaction was cooled to rt, filtered through a pad of Celite™ and concentrated in vacuo. Chromatography on silica gel (10% EtOAc/hexanes) afforded 7.5 g (80%) of benzyl ether A1 as a colorless oil:

A1: R$_f$(15% EtOAc/hexanes)=0.66; IR 2988, 2952, 2874, 1750, 1497, 1454, 1372, 1275, 1207, 1143, 1066, 1025, 739, 698 cm$^{-1}$; $^1$H NMR (300 MHz, CDCl$_3$) δ1.44 (3H, d, J=6.8 Hz, C27), 3.75 (3H, s, CH$_3$O), 4.07 (1H, q, J=6.8 Hz, C26), 4.45 (1H, d, J=11.7 Hz, CH$_2$Ph), 4.69 (1H, d, J=11.7 Hz, CH$_2$Ph), 7.28–7.37 (5H, m, Ph); $^{13}$C NMR (75 MHz, CDCl$_3$) δ18.6, 51.8, 71.9, 73.9, 127.7, 127.8, 128.3, 137.4, 173.6; HRMS Calcd for C$_{11}$H$_{14}$O$_3$ (M$^+$): 194.0943. Found: 194.0942.

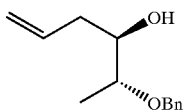
A3

To a solution of methyl ester A1 (6.3 g, 32.3 mmol) in Et$_2$O (150 mL) was added DIBAL-H (1.0M in hexanes, 38.75 mL) dropwise at −78° C. via cannulating needle. After 5 min at −78° C., the reaction was quenched with H$_2$O and gradually warmed to rt. The resultant thick emulsion was filtered through a pad of Celite™ and sand, rinsing thoroughly with Et$_2$O and EtOAc. The organic phase was washed with NaHCO$_3$ (2×), dried over MgSO$_4$ and concentrated in vacuo to afford crude aldehyde A2 (not shown) as a light yellow liquid.

To a solution of SnCl$_4$ (1.0M in CH$_2$Cl$_2$, 32.3 mmol) in CH$_2$Cl$_2$ (120 mL) was slowly added a CH$_2$Cl$_2$ solution of aldehyde A2 at −78° C. The mixture was stirred for an additional 10 min before allyltrimethylsilane (5.65 mL, 35.53 mmol) was added via syringe. The ensuing white suspension was kept at −78° C. for 10 min, quenched by addition of H$_2$O and allowed to warm to rt. The aqueous layer was extracted with Et$_2$O and the combined organics were dried over MgSO$_4$ and concentrated in vacuo. Chromatography on silica gel (10% EtOAc/hexanes) afforded 4.87 g (76%) of desired diastereomer A3 plus 300 mg (5%) of a putative mixture.

A3: R$_f$(15% EtOAc/hexanes)=0.44; IR (film) 3454, 3066, 3030, 2976, 2871, 1641, 1497, 1554, 1375, 1071, 1028, 992, 914, 737, 698 cm$^{-1}$; $^1$H NMR (300 MHz, CDCl$_3$) δ1.20 (3H, d, J=6.2 Hz, C27), 2.22 (1H, m, C24), 2.35 (1H, m, C24), 2.56 (1H, br s, OH), 3.45 (1H, m, C25), 4.25 (1H, m, C26), 4.44 (1H, d, J=11.5 Hz, CH$_2$Ph), 4.66 (1H, d, J=11.5 Hz, CH$_2$Ph), 5.10 (2H, m, CH$_2$=CH), 5.87 (1H, m, CH$_2$=CH), 7.28–7.35 (5H, m, Ph); $^{13}$C-NMR (75 MHz, CDCl$_3$) δ15.3, 37.4, 70.9, 74.1, 77.3, 117.03, 127.6, 127.7, 128.3, 134.7, 138.2; HRMS Calcd for C$_{13}$H$_{18}$O$_2$ (M$^+$): 206.1307. Found: 206.1313.

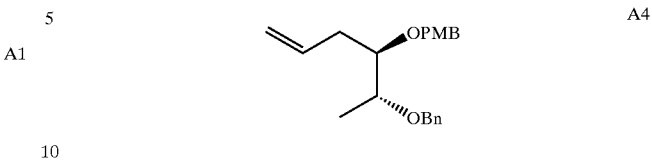
A4

To a suspension of potassium tert-butoxide (4.0 g, 35.7 mmol) in 120 mL anhydrous THF was added a solution of alcohol A3 (in 30 mL of THF) slowly over 15 min at 0° C. When complete, the mixture was stirred at rt for 45 min and then warmed to 60° C. for an additional 30 min. p-Methoxybenzylchloride (3.56 mL, 26 mmol) was added and the mixture was stirred at 60° C. for 4 h. The reaction was cooled to rt and quenched with sat. NH$_4$Cl. The aqueous layer was extracted with Et$_2$O (3×) and the combined organics were dried over MgSO$_4$ and concentrated in vacuo. The crude product was purified by flash chromatography (5% EtOAc/hexanes) to provide 6.80 g (88%) of differentially protected diol A4 as a colorless oil.

A4: R$_f$(15% EtOAc/hexanes)=0.59; IR (film) 3065, 2935, 2868, 1641, 1613, 1586, 1514, 1464, 1380, 1302, 1248, 1094, 1037, 913, 821, 737 cm$^{-1}$; $^1$H NMR (300 MHz, CDCl$_3$) δ1.17 (3H, d, J=6.3 Hz, C27), 2.27 (1H, m, C24), 2.40 (1H, m, C24), 3.44 (1H, ddd, J=7.7, 4.7, 4.6 Hz, C25), 3.62 (1H, dq, J=7.7, 6.3 Hz, C26), 3.78 (3H, s, CH$_3$O), 4.51 (1H, d, J=11.9 Hz, CH$_2$Ph), 4.52 (2H, s, CH$_2$Ph), 4.60 (1H, d, J=11.9 Hz, CH$_2$Ph), 5.04 (2H, m, CH$_2$=CH), 5.84 (1H, m, CH=CH$_2$), 6.83 (2H, d, J=8.7 Hz, Ar), 7.23–7.33 (7H, m, Ar); $^{13}$C-NMR (75 MHz, CDCl$_3$) δ15.0, 34.4, 55.1, 71.2, 72.1, 75.7, 80.9, 113.6, 116.6, 127.4, 127.6, 127.6, 128.3, 129.4, 130.9, 135.6, 138.9, 159.2; HRMS Calcd for C$_{21}$H$_{26}$O$_3$ (M$^+$): 326.1882. Found: 326.1876; Anal. Calcd for C$_{21}$H$_{26}$O$_3$: C, 77.27; H, 8.03. Found: C, 77.22; H, 8.16; [α]$_D^{20}$=−8.9° (c 1.43, CH$_2$Cl$_2$).

Formula 102

A4 (3.0 g, 9.2 mmol) was dissolved in 90 mL CH$_2$Cl$_2$/22.5 mL MeOH and cooled to −78° C. Ozone was bubbled through the solution which was carefully monitored for the disappearance of starting material by TLC (thin layer chromatography). When the consumption of A4 was judged complete, the system was immediately purged with N$_2$ for 20 min and treated with solid thiourea (840 mg, 11.04 mmol). The reaction was warmed to rt slowly over 5 hours and stirred at rt for 6 hours. The solvents were removed in vacuo, and the crude mixture was purified by flash chromatography (20% EtOAc/hexanes) to afford 2.40 g (80%) of aldehyde 102 as a colorless oil.

102: R$_f$ (15% EtOAc/hexanes)=0.31; IR (film) 2868, 2729, 1723, 1612, 1513, 1458, 1384, 1303, 1249, 1174, 1094, 822, 742 cm$^{-1}$; $^1$H NMR (300 MHz, CDCl$_3$) δ1.17 (3H, d, J=6.4 Hz, C27), 2.57 (1H, ddd, J=16.6, 7.8, 2.4 Hz, C24), 2.67 (1H, ddd, J=16.6, 4.4, 1.6 Hz, C24), 3.71 (1H, dq, J=6.4, 4.5 Hz, C26), 3.78 (3H, s, CH$_3$O), 4.05 (1H, ddd, J=7.8, 4.5, 4.4 Hz, C25), 4.45 (1H, d, J=11.8 Hz, CH$_2$Ph), 4.50 (2H, s, CH$_2$Ph), 4.58 (1H, d, J=11.8 Hz, CH$_2$Ph), 6.84 (2H, d, J=8.7 Hz, Ar), 7.20–7.35 (7H, m, Ar), 9.70 (1H, dd, J=2.4, 1.6 Hz, CHO); $^{13}$C NMR (75 MHz, CDCl$_3$) δ14.2, 44.1, 55.1, 70.9, 72.0, 74.5, 75.1, 113.8, 127.7, 127.7, 128.4, 129.5, 130.2, 138.4, 159.4, 201.4; HRMS Calcd for C$_{20}$H$_{24}$O$_4$ (M$^+$): 328.1675. Found: 328.1664; Anal. Calcd for C$_{20}$H$_{24}$O$_4$: C, 73.13; H, 7.37. Found: C, 72.81; H. 7.40; [α]$_D^{20}$=−9.1° (c 1.06, CH$_2$Cl$_2$).

1B. Diketone 101

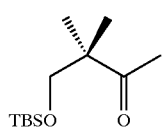

A6

A mixture of methylisopropyl ketone (53.4 mL, 0.5 mol) and paraformaldehyde (19.5 g, 0.65 mol) in 200 mL $CF_3CO_2H$ was stirred at 60° C. for 18 h. The reaction mixture was concentrated on a rotary evaporator (warm water bath) with a KOH trap and poured into a cold (5° C.) mixture of EtOAc and sat. aqueous $NaHCO_3$. The layers were separated and the organic layer was washed with brine, dried over $MgSO_4$, and concentrated in vacuo. Short path distillation gave the trifluoroacetate ester of 3,3-dimethyl-4-hydroxy butanone (bp=53–55° C. at 2 mm Hg, 72.4 g) in 68% yield. This material was dissolved in 400 mL MeOH and treated with 190 mL of 2N NaOH at 0° C. After 1 h at 0° C., the reaction mixture was concentrated in vacuo and the residue was partitioned between EtOAc and sat. aqueous $NH_4Cl$. The organic layer was washed with brine, dried over $MgSO_4$, and concentrated to afford 40.1 g (~100%) of 3,3-dimethyl-4-hydroxy butanone (A5) as a colorless liquid. Crude A5 was taken up in 200 mL anhydrous DMF and treated with t-butyldimethylsilylchloride (57.3 g, 0.38 mol) and imidazole (25.9 g, 0.38 mol) at 0° C. After stirring at rt for 2 h, the solution was diluted with EtOAc, washed with sat. aqueous $NaHCO_3$ solution and brine, dried over $MgSO_4$ and concentrated in vacuo. The residue was distilled under reduced pressure to afford silyl ether ketone A6 (bp=65° C. at 1.5 mm Hg, 55.76 g, 81%) as a colorless oil.

A6: $R_f$(25% EtOAc/hexanes)=0.90; IR (film) 2957, 2931, 2858, 1713, 1473, 1362, 1257, 1136, 1097, 838, 777 $cm^{-1}$; $^1$H NMR (300 MHZ, $CDCl_3$) δ0.03 (6H, s), 0.87 (9H, s), 1.09 (6H, s), 2.17 (3H, s), 3.57 (2H, s); $^{13}$C NMR (75 MHz, $CDCl_3$) δ5.7, 18.1, 21.4, 25.7, 26.1, 49.6, 70.2, 213.4; HRMS Calcd for $C_{12}H_{26}O_2Si$ ($M^+$—$CH_3$): 215.1467. Found: 215.1469.

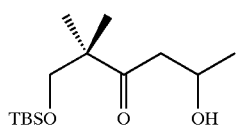

A7

To a stirred solution of diisopropylamine (12.6 mL, 96 mmol) in THF (200 mL) was added n-butyllithium (38.4 mL, 2.5M in hexane, 96 mmol) dropwise at 0° C. The mixture was stirred at 0° C. for 30 min, cooled to –78° C., and treated with a solution of ketone A6 (20.0 g, 87 mmol) in THF (50 mL) slowly over 10 min. After stirring at –78° C. for 40 min, acetaldehyde (5.34 mL, 96 mmol) was added and the mixture was kept at –78° C. for 2 h and at –40° C. for 1.5 h. The reaction was quenched with saturated $NH_4Cl$ solution (20 mL) and allowed to warm gradually to rt. The mixture was extracted with ether and the combined organics were washed with brine, dried over $MgSO_4$ and concentrated in vacuo to afford nearly pure aldol A7 (19 g, 80%) as a pale yellow oil. An analytical sample was obtained following chromatography on silica gel.

A7: $R_f$(15% EtOAc/hexanes)=0.33; IR (film) 2958, 2930, 2858, 1699, 1472, 1392, 1363, 1258, 1101, 838, 777 $cm^{-1}$; $^1$H NMR (300 MHz, $CDCl_3$) δ4.16 (1H, m), 3.55 (2H, s), 3.36 (1H, s), 2.74 (1H, dd, J=18.0, 2.4 Hz), 2.68 (1H, dd, J=18.0, 9.0 Hz), 1.16 (3H, d, J=6.3 Hz), 1.08 (3H, s), 1.07 (3H, s), 0.85 (9H, s), 0.01 (6H, s); $^{13}$C NMR (75 MHz, $CDCl_3$) δ–5.7, 18.1, 21.3, 22.3, 25.8, 46.2, 49.7, 63.9, 70.2, 216.8; Anal. Calcd for $C_{14}H_{30}O_3Si$: C, 61.26; H, 11.02. Found: C, 61.01; H, 11.28.

Formula 101

To a solution of oxalyl chloride (5.3 mL, 60.4 mmol) in $CH_2Cl_2$ (150 mL) was added dimethyl sulfoxide (8.56 mL, 120.8 mmol) dropwise at –78° C. After 20 min, a solution of crude alcohol A7 (15.0 g, 54.9 mmol) in $CH_2Cl_2$ (150 mL) was added over 10 min and the mixture was stirred at –78° C. for 1 h. $Et_3N$ (38 mL, 275 mmol) was added and the mixture was stirred for 20 min, brought to 0° C., quenched with sat. aqueous $NH_4Cl$ and diluted with EtOAc. The layers were separated and the aqueous layer was extracted with EtOAc (2×). The combined organics were washed with brine, dried over $MgSO_4$, and concentrated in vacuo. Flash chromatography on silica gel (5→10% EtOAc/hexanes) provided enolic β-diketone 101 (12.0 g, 81%) as a yellow oil.

101: $R_f$ (15% EtOAc/hexanes)=0.68; IR (film) 2957, 2930, 1606, 1472, 1362, 1257, 1102, 838, 777 $cm^{-1}$; $^1$H NMR (300 MHZ, $CDCl_3$) δ0.01 (6H, s), 0.85 (9H, s), 1.10 (6H, s), 2.05 (3H, s), 3.53 (2H, s), 5.62 (1H, s); $^{13}$C NMR (75 MHz, $CDCl_3$) δ–5.5, 18.3, 22.1, 25.5, 25.9, 44.9, 70.0, 98.0, 192.6, 198.5; Anal. Calcd for $C_{14}H_{28}O_3Si$: C, 61.72; H, 10.36. Found: C, 61.08; H, 10.43.

1C. Dibenzyl Ether Octanoate 111

Formulae 104a and 104b

To a solution of diisopropylamine (3.21 mL, 23 mmol) in 25 mL THF at –60° C. was added n-butyllithium (1.6 M in hexanes, 13.83 mL, 22.13 mmol) dropwise. The colorless solution was warmed to 0° C. and stirred for 30 min. A THF solution (35 mL) of diketone 101 (Example 1B) (2.98 g, 10.9 mmol) was subsequently added via cannula and the mixture was stirred for 1 h at 0° C. The reaction was re-cooled to –78° C. and treated with a solution of aldehyde 102 (Example 1A) (3.0 g, 9.15 mmol) in 35 mL THF. After 30 min at –78° C., the mixture was quenched with sat. $NH_4Cl$ and brought to rt. The aqueous layer was extracted with $Et_2O$, the combined organics were dried over $MgSO_4$ and the solvent was removed in vacuo. The crude residue was quickly passed through a column of silica gel (20% EtOAc/hexanes) to provide 5.40 g (98%) of aldol diastereomer mixture 103 as an approximately 1:1 mixture of diastereomers.

A portion of isolated 103 (2.50 g, 4.2 mmol) was dissolved in 60 mL anhydrous toluene and treated with 4 Å molecular sieves (1.55 g) and p-toluenesulfonic acid (60 mg). The reaction was stirred at room temperature for 4.5 h, quenched with 2 mL pyridine and concentrated. The residue was taken up in $Et_2O$, washed with sat. $NaHCO_3$, dried over $MgSO_4$ and the solvent was removed in vacuo. Flash chromatography (20–>25% EtOAc/hexanes) afforded pyrone compounds 104a (1.0 g) and 104b (1.2 g) in 90% overall yield as colorless oils.

104b: $R_f$ (30% EtOAc/hexanes)=0.59; $^1$H NMR (300 MHz, $CDCl_3$) δ0.05 (6H, s, TBS), 0.85 (9H, s, TBS), 1.05 (3H, s, C18 Me), 1.06 (3H, s, C18 Me), 1.20 (3H, d, J=5.8 Hz, C27), 1.98 (2H, m, C24), 2.12 (1H, dd, J=16.7, 3.6 Hz, C24), 2.28 (1H, dd, J=16.7, 13.7 Hz, C22), 3.44 (2H, s, C17), 3.54 (1H, m, C25), 3.72 (1H, m, C26), 3.81 (3H, s, CH$_3$O), 4.23 (1H, m, C23), 4.40 (1H, d, J=11.2 Hz, CH$_2$Ph), 4.47 (1H, d, J=11.8 Hz, CH$_2$Ph), 4.52 (1H, d, J=11.2 Hz, CH$_2$Ph), 4.63 (1H, d, J=11.8 Hz, CH$_2$Ph), 5.39 (1H, s, C20), 6.85 (2H, d, J=8.7 Hz, Ar), 7.17–7.35 (7H, m, Ar); $^{13}$C NMR (75 MHz, CDCl$_3$) δ–5.5, 14.7, 18.2, 22.4, 25.9, 34.5, 40.9, 42.4, 55.4, 69.6, 71.2, 72.0, 74.3, 76.2, 103.5, 114.1, 127.9, 128.0, 128.7, 128.8, 129.9, 130.4, 138.8, 159.7, 182.2, 193.7; HRMS Calcd for C$_{34}$H$_{50}$O$_6$Si (M$^+$): 582.3377. Found: 582.3370.

104a: R$_f$ (30% EtOAc/hexanes)=0.52; IR 2955, 2857, 1667, 1599, 1514, 1397, 1336, 1301, 1249, 1174, 1102, 838 cm$^{-1}$; $^1$H NMR (300 MHz, CDCl$_3$) δ0.05 (6H, s, TBS), 0.87 (9H, s, TBS), 1.10 (3H, s, C18 Me), 1.14 (3H, s, C18 Me), 1.21 (3H, d, J=6.3 Hz, C27), 1.71 (1H, m, C24), 2.10 (1H, m, C24), 2.42 (2H, m, C22), 3.48 (1H, d, J=9.3 Hz, C17), 3.58 (1H, d, J=9.3 Hz, C17), 3.76 (1H, m, C26), 3.82 (3H, s, CH$_3$0), 3.83 (1H, m, C25), 4.43 (1H, d, J=10.7 Hz, CH$_2$Ph), 4.56 (1H, br m, C23), 4.57 (1H, d, J=11.8 Hz, CH$_2$Ph), 4.63 (1H, d, J=10.7 Hz, CH$_2$Ph), 4.65 (1H, d, J=11.8 Hz, CH$_2$Ph), 5.47 (1H, s, C20), 6.87 (2H, d, J=8.6 Hz, Ar), 7.20 (2H, d, J=8.6 Hz, Ar), 7.32–7.38 (5H, m, Ar); $^{13}$C-NMR (75 MHz, CDCl$_3$) δ–5.6, 14.4, 18.1, 22.3, 22.5, 25.7, 35.2, 41.5, 42.3, 55.2, 69.4, 71.1, 72.8, 74.8, 75.9, 76.4, 103.2, 113.8, 127.5, 128.3, 129.3, 130.3, 138.5, 159.2, 181.1, 193.4; HRMS Calcd for C$_{34}$H$_{50}$O$_6$Si (M$^+$): 582.3377. Found: 582.3369; Anal. Calcd for C$_{34}$H$_{50}$O$_6$Si: C, 70.06; H, 8.65. Found: C, 69.95; H, 8.77; [α]$_D^{20}$=+43.9° (c 0.70, CH$_2$Cl$_2$).

Formula 105

To a solution of pyrone 104a (680 mg, 2.4 mmol) and CeCl$_3$.7H$_2$O (218 mg, 0.59 mmol) in 40 mL methanol was added solid NaBH$_4$ (89 mg, 2.3 mmol) in a single portion at –20° C. The reaction mixture was stirred for 1 h at –20° C. and then quenched with 50 mL brine. The mixture was brought to rt, filtered through a pad of Celite™ and extracted with EtOAc (4×). The combined organics were dried over Na$_2$SO$_4$ and concentrated in vacuo to afford a crude allylic alcohol. This moderately stable oil was carried forward without purification.

Crude allylic alcohol was dissolved in 45 mL CH$_2$Cl$_2$/MeOH (2:1) and treated with solid NaHCO$_3$ (243 mg, 2.9 mmol). Purified m-CPBA (377 mg, 2.20 mmol) was added in a single portion and the reaction mixture was stirred at rt for 1 h. The mixture was quenched with Et$_3$N (15 mL), stirred for 20 min, diluted with 200 mL Et$_2$O, and filtered through a pad of Celite™. The filtrate was concentrated in vacuo and the residue was purified by flash chromatography (40% EtOAc/hexanes) to give 650 mg (71% from 104a) of syn diol 105 as a colorless oil.

105: R$_f$ (30% EtOAc/hexanes)=0.29; IR (film) 3372, 1613, 1514, 1465, 1390, 1302, 1249, 1180, 1150, 1072, 935, 837, 779, 736, 698, 673 cm$^{-1}$; $^1$H NMR (300 MHz, CDCl$_3$) δ0.09 (6H, s, TBS), 0.91 (9H, s, TBS), 1.03 (3H, s, C18 Me), 1.07 (3H, s, C18 Me), 1.18 (3H, d, J=6.3 Hz, C27), 1.50–1.68 (2H, m, C24/C22), 1.80 (11H, m, C22), 2.57 (11H, app d, J=11.2 Hz, C24), 3.28 (3H, s, CH$_3$O), 3.39, (1H, d, J=10.1 Hz, C17), 3.62 (1H, d, J=11.2 Hz, C17), 3.79 (3H, s, CH$_3$O), 3.71–3.94 (5H, m, CH$_2$Ph, C23/C25/C26), 4.40 (1H, d, J=10.7 Hz, CH$_2$Ph), 4.56 (1H, d, J=11.8 Hz, CH$_2$Ph), 4.62 (1H, d, J=11.5 Hz, CH$_2$Ph), 5.40 (11H, d, J=2.5 Hz, OH), 6.84 (2H, d, J=8.7 Hz, PMB), 7.18 (2H, d, J=8.7 Hz, PMB), 7.37–7.26 (5H, m, Bn).

Formula 106

A solution of diol 105 (0.81 g, 1.28 mmol) and 4-dimethylaminopyridine (DMAP, 0.55 g, 4.48 mmol) in 22 mL CH$_2$Cl$_2$ was cooled to –10° C. and treated with benzoyl chloride (193 μL, 1.66 mmol) dropwise via syringe. The resulting mixture was stirred at –10° C. for 30 min, quenched with sat NaHCO$_3$ and diluted with EtOAc (150 mL). The organic layer was washed with H$_2$O and brine, dried over Na$_2$SO$_4$ and concentrated in vacuo to afford a crude mixture of C21 monobenzoate and 4-dimethylaminopyridine as a colorless paste.

The crude C21 monobenzoate was taken up in 45 mL CH$_2$Cl$_2$ and treated with solid 1,1,1-triacetoxy-1,1-dihydro-1,2-benziodoxol-3(1H)-one (Dess-Martin periodinane or DMP, 1.78 g, 4.20 mmol) at rt. The solution was stirred for 10 h at rt after which a second portion (0.50 g, 1.18 mmol) of DMP was added. The opaque white mixture was stirred for another 1.5 h and quenched with 30 mL sat. NaHCO$_3$/Na$_2$S$_2$O$_3$. The two phase system was vigorously stirred until the organic layer cleared (~25 min). The layers were separated and the aqueous phase was extracted with CH$_2$Cl$_2$ (2×). The combined organics were dried over Na$_2$SO$_4$ and concentrated in vacuo to provide a colorless semi-solid. Flash chromatography on silica gel (25% EtOAc/hexanes) gave 106 (0.85 g–90% from 105) as a colorless oil.

106: R$_f$ (15% EtOAc/hexanes)=0.43; IR (film) 2954, 2933, 1754, 1723, 1610, 1513, 1451, 1267, 1251 cm$^{-1}$; $^1$H NMR (300 MHz, CDCl$_3$) δ0.01 (6H, s, TBS), 0.88 (9H, s, TBS), 1.12 (3H, s, C18 Me), 1.14 (3H, s, C18 Me), 1.19 (3H, d, J=6.3 Hz, C27), 1.64–1.73 (1H, m, C24), 1.82–1.90 (1H, m, C24), 2.13 (1H, app q, J=12.4 Hz, C22), 2.40 (1H, ddd, J=12.4, 6.5, 1.6 Hz, C22), 3.54 (3H, s, C19 OCH$_3$), 3.65 (1H, d, J=9.2 Hz, C17), 3.69 (1H, d, J=9.2 Hz, C17) 3.72–3.81 (2H, m), 3.81 (3H, s, ArOCH$_3$), 3.89 (1H, m), 4.49 (1H, d, J=10.7 Hz, CH$_2$Ar), 4.57 (1H, d, J=13.0 Hz, CH$_2$Ar), 4.61 (1H, d, J=13.0 Hz, CH$_2$Ar), 4.62 (1H, d, J=10.7 Hz, CH$_2$Ar), 5.80 (1H, dd, J=12.9, 6.3 Hz, C21), 6.87 (2H, d, J=8.3 Hz, Ar), 7.26–7.36 (7H, m, Ar), 7.45 (2H, m, Ar), 7.58 (1H, app t, J=7.2 Hz, Ar), 8.09 (2H, d, J=7.2 Hz, Ar); $^{13}$C-NMR (75 MHz, CDCl$_3$) δ–5.3, 14.7, 18.5, 20.4, 20.6, 26.1, 35.5, 40.4, 45.1, 53.8, 55.5, 65.4, 67.2, 71.4, 73.0, 73.3, 75.1, 103.8, 114.1, 127.9, 128.6, 128.7, 129.7, 129.9, 130.2, 131.0, 133.6, 138.9, 159.6, 165.9, 198.6; HRMS Calcd for C$_{42}$H$_{58}$O$_9$Si (M$^+$-MeOH): 702.3588. Found: 702.3563; Anal. Calcd for C$_{42}$H$_{58}$O$_9$Si: C, 68.63; H, 7.96. Found: C, 68.28; H, 8.11; [α]$_D^{20}$=+22.4° (c 1.53, CH$_2$Cl$_2$).

Formula 107

A solution of benzoate 106 (0.85 g, 1.16 mmol) in 20 mL THF/MeOH (3:1) was titrated with SmI$_2$ (0.1 M in THF, 25.5 mL, 2.55 mmol) at –78° C. until an olive green color persisted. The reaction mixture was quenched with 4 mL sat. NaHCO$_3$, warmed to rt and diluted with EtOAc (150 mL). The organic layer was washed with NaHCO$_3$, H$_2$O and brine, dried over Na$_2$SO$_4$ and concentrated in vacuo. Flash chromatography on silica gel (20% EtOAc/hexanes) afforded ketone 107 (675 mg, 95%) as a light yellow oil.

107: R$_f$ (15% EtOAc/hexanes)=0.39; IR (film) 2954, 2930, 1723, 1612, 1514, 1464, 1250, 1088 cm$^{-1}$; $^1$H NMR (300 MHz, CDCl$_3$) δ0.01 (6H, s, TBS), 0.87 (9H, s, TBS), 0.95 (3H, s, C18 Me), 1.05 (3H, s, C18 Me), 1.19 (3H, d, J=6.3 Hz, C27), 1.64 (1H, m, C24), 1.85–1.96 (3H, m, C21+C24), 2.29 (1H, 5 line m, C22), 2.65 (1H, m, C22), 3.23 (3H, s, C19 OCH$_3$), 3.31 (1H, d, J=9.9 Hz, C17), 3.71 (1H, d, J=9.9 Hz, C17), 3.78 (3H, s, ArOCH$_3$), 3.79 (1H, m), 3.98 (1H, m), 4.17 (1H, m), 4.43 (1H, d, J=11.0 Hz, CH$_2$Ar), 4.58 (2H, s, CH$_2$Ar), 4.60 (1H, d, J=11.0 Hz, CH$_2$Ar), 6.84 (2H, d, J=8.7 Hz, PMB), 7.19 (2H, d, J=8.7 Hz, PMB), 7.28–7.35 (5H, m, Bn); $^{13}$CNMR (75 MHz, CDCl$_3$) δ–5.5, −5.4, 14.5, 18.6, 19.8, 20.2, 26.0, 29.7, 36.5, 38.2, 46.2, 52.4, 55.4, 68.6, 70.6, 71.3, 72.3, 74.7, 103.6, 114.1, 127.9, 128.7, 129.6, 131.0, 138.9, 159.5, 207.5; HRMS Calcd for $C_{35}H_{54}O_7Si$ ($M^+$-MeOH): 582.3377. Found: 582.3372; Anal. Calcd for $C_{35}H_{54}O_7Si$: C, 68.37; H, 8.85. Found: C, 68.04; H, 8.84; $[\alpha]_D^{20}$=+21.90° (c 0.72, $CH_2Cl_2$).

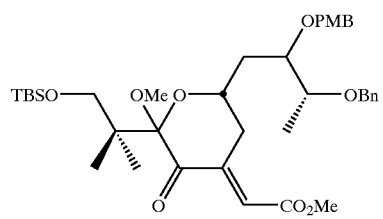

109.1 (Formula 109 where $R^{21}$ is =CH—$CO_2Me$)

To a solution of diisopropylamine (150 μL, 1.15 mmol) in THF (1.61 mL) was added n-BuLi (2.5 M in hexanes, 440 μL, 1.10 mmol) dropwise at 0° C. After 5 min at 0° C., a 1.81 mL aliquot (0.5 M LDA, 0.90 mmol) was removed via syringe and slowly added to a solution of ketone 107 (483 mg, 0.79 mmol) in THF (20 mL) at −78° C. The solution was stirred for 10 min, treated with a stock solution of $OHCCO_2Me$ (0.5 M in $Et_2O$, 4.0 mL, 2.0 mmol), kept at −78° C. for 20 min and quenched with 3 mL sat. $NH_4Cl$. The reaction mixture was brought to rt and diluted with 200 mL EtOAc. The organic layer was washed with $H_2O$ (2×) and brine, dried over $Na_2SO_4$ and concentrated in vacuo. The crude residue was chromatographed on silica gel (35% EtOAc/hexanes) to afford residual 107 (142 mg) and aldols 108 as a mixture of diastereomers (352 mg, 90% based on recovered 107).

The isolated 108 mixture and $Et_3N$ (418 μL, 3.0 mmol) were dissolved in anhydrous $CH_2Cl_2$ (15 mL) and cooled to −10° C. Methanesulfonylchloride (116 μL, 1.5 mmol) was added via syringe and the solution was stirred at −10° C. for 30 min. 5 mL sat. $NaHCO_3$ was added, the reaction mixture was warmed to rt and diluted with 100 mL EtOAc. The organic layer was washed with $H_2O$ and brine, dried over $Na_2SO_4$ and concentrated in vacuo. The residue was immediately dissolved in THF (30 mL) and treated with 1,8-diazabicyclo[5.4.0]undec-7-ene (DBU, 75 μL, 0.50 mmol) dropwise at rt. The resulting bright yellow solution was stirred at rt for 20 min, treated with sat. $NH_4Cl$ and diluted with 150 mL EtOAc. The organic layer was washed with $H_2O$ and brine, dried over $Na_2SO_4$ and concentrated in vacuo to afford an orange residue which was chromatographed on silica gel (20% EtOAc/hexanes) to afford exocyclic methacrylate (enone) 109.1 (267 mg, 78% from 108) as a yellow oil.

109.1: $R_f$ (30% EtOAc/hexanes)=0.63; IR (film) 2954, 2930, 1724, 1707, 1612, 1514, 1464, 1250, 1088 cm$^{-1}$; $^1$H NMR (300 MHz, $CDCl_3$) δ0.05 (6H, s, TBS), 0.81 (9H, s, TBS), 0.91 (3H, s, C18 Me), 1.00 (3H, s, C18 Me), 1.19 (3H, d, J=6.4 Hz, C27), 1.74 (1H, m, C24), 1.94 (1H, m, C24), 2.71 (1H, ddd, J=17.6, 12.4, 3.1 Hz, C22), 3.19 (3H, s, C19 $OCH_3$), 3.26 (1H, d, J=10.0 Hz, C17), 3.49 (1H, d, J=17.6 Hz, C22), 3.68 (1H, d, J=10.0 Hz, C17), 3.74 (3H, s), 3.77 (3H, s), 3.80 (1H, m), 3.97 (1H, m), 4.19 (1H, m), 4.40 (1H, d, J=10.9 Hz, $CH_2Ar$), 4.53–4.63 (3H, m, $CH_2Ar$), 6.64 (11H, d, J=1.9 Hz, C34), 6.82 (2H, d, J=8.7 Hz, PMB), 7.14 (2H, d, J=8.7 Hz, PMB), 7.27–7.36 (5H, m, Bn); $^{13}$C-NMR (75 MHz, $CDCl_3$) δ−5.9, −5.8, 14.1, 18.3, 19.3, 19.8, 25.7, 35.2, 36.0, 46.6, 51.6, 52.1, 55.1, 68.2, 69.5, 71.0, 71.7, 74.2, 76.0, 104.0, 113.8, 122.4, 127.6, 128.4, 129.1, 130.6, 138.6, 147.3, 159.2, 166.4, 196.2; HRMS Calcd for $C_{38}H_{56}O_9Si$ ($M^+$-MeOH): 652.3433. Found: 652.3435; Anal. Calcd for $C_{38}H_{56}O_9Si$: C, 66.64; H, 8.24. Found: C, 66.87; H, 8.13; $[\alpha]_D^{20}$=−55.8° (c 0.78, $CH_2Cl_2$).

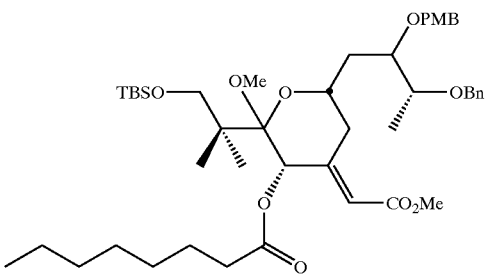

111.1 (Formula 111 where $R^{20}$ is —O—CO—$C_7H_{15}$ and $R^{21}$ is =CH—$CO_2Me$)

To a solution of enone 109.1 (502 mg, 0.734 mmol) and $CeCl_3 \cdot 7H_2O$ (137 mg, 0.367 mmol) in methanol (23 mL) was added solid $NaBH_4$ (56 mg, 1.47 mmol) in a single portion at −30° C. Rapid gas evolution subsided after 3 min. After an additional 30 min at −30° C., the reaction mixture was poured directly onto a silica gel column and the product quickly eluted with 25% EtOAc/hexanes to afford the corresponding axial alcohol 110.1 (478 mg) as a colorless oil.

Octanoic acid (232 mg, 1.61 mmol) and $Et_3N$ (292 μL, 2.20 mmol) were dissolved in 20 mL toluene and treated with 2,4,6-trichlorobenzoylchloride (230 μL, 1.47 mmol) dropwise at rt. After 1 h at rt, a toluene solution (7 mL) of freshly prepared 110.1 was added gradually via syringe and stirring was continued for 40 min. The reaction mixture was quenched with 10 mL sat. $NaHCO_3$, diluted with EtOAc and washed successively with sat. $NH_4Cl$ and brine. The organics were dried over $Na_2SO_4$, the solvent was removed in vacuo, and the residue was chromatographed on silica gel (25% EtOAc/hexanes) to provide octanoate 111.1 as a colorless oil (551 mg, 93% from 109.1).

111.1: $R_f$ (25% $Et_2O$/hexanes)=0.33; IR (film) 2928, 2857, 1747, 1722, 1667, 1614, 1514, 1463, 1250, 1155, 1081, 836.2 cm$^{-1}$; $^1$H NMR (300 MHz, $CDCl_3$) δ−0.01 (6H, s, TBS), 0.88 (12H, br s, TBS+octanoate Me), 0.99 (3H, s, C18 Me), 1.03 (3H, s, C18 Me), 1.19 (3H, d, J=6.3 Hz, C27), 1.20–1.35 (8H, m), 1.60–1.80 (3H, m), 1.89 (1H, m, C24), 2.31–2.40 (3H, m), 3.26 (3H, s, C19 $OCH_3$), 3.44 (1H, dd, J=15.6, 1.8 Hz, C22), 3.56 (1H, d, J=9.3 Hz, C17), 3.60 (1H, d, J=9.3 Hz, C17), 3.68 (3H, s), 3.78 (1H, m), 3.79 (3H, s), 3.93 (1H, dd, J=8.4, 4.8 Hz), 4.13 (1H, m), 4.38 (1H, d, J=10.8 Hz, $CH_2Ar$), 4.57 (1H, d, J=10.8 Hz, $CH_2Ar$), 4.60 (2H, s, $CH_2Ar$), 5.57 (1H, s, C20), 5.89 (1H, s, C34), 6.83 (2H, d, J=8.4 Hz, PMB), 7.16 (2H, d, J=8.4 Hz, PMB), 7.28–7.38 (5H, m, Bn); $^{13}$C NMR (75 MHz, $CDCl_3$) δ−5.4, 14.1, 14.2, 14.4, 18.4, 20.7, 22.7, 24.8, 26.0, 28.9, 26.0, 28.9, 31.7, 33.2, 34.6, 36.4, 47.1, 51.2, 55.3, 67.6, 68.1, 71.2, 72.2, 74.7, 76.5, 103.1, 114.0, 117.0, 127.8, 128.6, 129.5, 129.9, 130.9, 139.0, 153.1, 159.5, 166.7, 172.2; HRMS Calcd for $C_{46}H_{72}O_{10}Si$ ($M^+$-MeOH): 780.4632. Found: 780.4610; $[\alpha]_D^{20}$=−5.1° (c 1.80, $CH_2Cl_2$).

Example 2

Exemplary Linkers

2A. Ketal Acid 406

Formula 402

To a stirred solution of the 1,3 menthone acetal of 1,3,5-pentanetriol 401 (3.33 g, 13 mmol) prepared by the method of Harada et al. (1993) in 23 mL of anhydrous CH$_2$Cl$_2$ was added 1,1,1-triacetoxy-1,1-dihydro-1,2-benziodoxol-3(1H)-one (Dess-Martin periodinane, 6.60 g, 15.6 mmol) in a single portion. The mixture was stirred at rt for 30 min, poured onto a column of silica gel and the product eluted with 15% EtOAc/hexanes to afford 3.013 g (90%) of pure aldehyde 402 as a colorless oil.

402: R$_f$ (20% EtOAc/hexanes)=0.50; IR (film) 2952, 2869, 1728, 1456, 1383, 1308, 1265 cm$^{-1}$; $^1$H NMR (300 MHz, CDCl$_3$) δ9.80 (1H, dd, J=1.8, 2.5 Hz), 4.36 (1H, dddd, J=2.9, 4.3, 7.4, 8.2 Hz), 4.13 (1H, ddd, J=2.7, 11.7, 11.9 Hz), 3.83 (1H, ddd, J=1.3, 5.2, 11.7 Hz), 2.72 (1H, ddd, J=1.9, 3.1, 13.5 Hz), 2.56 (1H, ddd, J=2.5, 8.2, 16.1 Hz), 2.44 (1H, ddd, J=1.8, 4.3, 16.1 Hz), 2.39 (1H, dsept, J=1.6, 7.1 Hz), 1.54–1.76 (3H, m), 1.29–1.53 (4H, m), 1.17 (1H, ddd, J=1.9, 4.1, 12.4 Hz), 0.90 (3H, d, J=6.3 Hz), 0.87 (3H, d, J=7.0 Hz), 0.85 (3H, d, J=7.0 Hz), 0.72 (1H, t, J=13.2 Hz); $^{13}$C NMR (75 MHz, CDCl$_3$) δ201.4, 100.9, 63.8, 58.7, 51.1, 49.9, 37.2, 34.8, 31.1, 28.9, 24.2, 23.7, 22.2, 21.7, 18.8; HRMS Calc'd for C$_{15}$H$_{26}$O$_3$: 254.1882. Found: 254.1877; [α]$_D^{20}$–11.2° (c 1.28, CHCl$_3$).

Formulae 403a and 403b

To a stirred solution of aldehyde 402 (3.013 g, 11.86 mmol) in 40 mL of anhydrous CH$_2$Cl$_2$ was added a solution of (+)-Eu(hfc)$_3$ (1.42 g, 1.19 mmol) in CH$_2$Cl$_2$ (16 mL) at rt. The resultant clear yellow solution was stirred for 5 min before 1-methoxy-3-(trimethylsilyloxy)-1,3-butadiene (3.47 mL, 3.07 g, 17.8 mmol) was introduced via syringe. The yellow solution was stirred at rt for 20 h, treated with 0.5 mL CF$_3$CO$_2$H and stirred for an additional 15 min. The solution was quenched with sat. NaHCO$_3$, diluted with EtOAc (200 mL), washed with H$_2$O and brine, dried over MgSO$_4$ and concentrated in vacuo. Purification by flash chromatography (20–>25% EtOAc/hexanes) provided anti pyrone 403b (2.53 g, 66%) and syn pyrone 403a (1.30 g, 34%) as colorless solids.

403b: mp=113–114° C. (hexanes); R$_f$ (15% EtOAc/hexanes)=0.25; $^1$H NMR (300 MHz, CDCl$_3$) δ7.31 (1H, d, J=6.0 Hz), 5.40 (1H, d, J=6.0 Hz), 4.67 (1H, dddd, J=3.0, 5.8, 9.6, 11.8 Hz), 4.03–4.15 (2H, m), 3.81 (1H, ddd, J=1.2, 5.2, 11.6 Hz), 2.70 (1H, ddd, J=1.9, 2.8, 13.5 Hz), 2.42–2.56 (2H, m), 2.38 (1H, dsept, J=1.6, 6.9 Hz), 1.91 (1H, ddd, J=2.3, 9.6, 14.3 Hz), 1.28–1.75 (8H, m), 1.18 (1H, ddd, J=1.9, 3.9, 12.5 Hz), 0.88 (3H, d, J=6.6 Hz), 0.87 (3H, d, J=7.1 Hz), 0.83 (3H, d, J=6.9 Hz), 0.70 (1H, t, J=12.6 Hz); $^{13}$C NMR (75 MHz, CDCl$_3$) δ192.7, 162.9, 107.3, 100.7, 75.7, 63.3, 58.9, 51.1, 42.5, 41.7, 37.3, 34.8, 31.7, 29.0, 24.2, 23.6, 22.2, 21.9, 18.9; LRMS (EI): 322 (68), 307 (22), 265 (33), 237 (67), 153 (24), 191 (94), 139 (52), 112 (20), 97 (100), 83 (31), 81 (47), 71 (24), 69 (35); HRMS Calcd for C$_{19}$H$_{30}$O$_4$: 322.2144. Found: 322.2142; Anal. Calcd for C$_{19}$H$_{30}$O$_4$: C, 70.77; H, 9.38. Found: C, 70.91; H, 9.58; [α]$_D^{20}$+42.50° (c 1.59, CH$_2$Cl$_2$).

403a: R$_f$ (15% EtOAc/hexanes)=0.15; IR 2952, 2869, 1682, 1597, 1456, 1405, 1269 cm$^{-1}$; $^1$H NMR (300 MHz, CDCl$_3$) δ7.33 (1H, d, J=6.0 Hz), 5.40 (1H, dd, J=0.9, 6.0 Hz), 4.61 (1H, dddd, J=2.8, 11.6, 12.0 Hz), 4.09 (1H, ddd, J=2.8, 11.6, 12.0 Hz), 4.00 (1H, dddd, J=1.0, 4.2, 8.3, 15.5 Hz), 3.81 (1H, ddd, J=1.4, 5.4, 11.6 Hz), 2.67 (1H, ddd, J=1.9, 3.2, 13.5 Hz), 2.63 (1H, dd, J=13.3, 16.8 Hz), 2.47 (1H, ddd, J=0.9, 4.0, 16.8 Hz), 2.39 (1H, dsept, J=1.6, 6.9 Hz), 2.02 (1H, ddd, J=5.6, 8.3, 14.0 Hz), 1.79 (1H, ddd, J=4.2, 6.9, 14.0 Hz), 1.20–1.75 (7H, m), 1.17 (1H, ddd, J=1.9, 3.8, 12.6 Hz), 0.89 (3H, d, J=6.7 Hz), 0.87 (3 H, d, J=6.9 Hz), 0.86 (3H, d, J=6.9 Hz), 0.70 (1H, t, J=13.5 Hz); $^{13}$C NMR (75 MHz, CDCl$_3$) δ192.6, 163.3, 107.1, 100.7, 76.4, 63.9, 58.8, 51.1, 41.6, 40.9, 37.3, 34.7, 31.4, 29.3, 24.2, 23.7, 22.2, 21.8, 18.8; LRMS (EI): 322 (61), 307 (18), 265 (27), 237 (56), 151 (21), 139 (33), 112 (17), 97 (100), 83 (26), 81 (34), 71 (17), 69 (60); HRMS Calcd for C$_{19}$H$_{30}$O$_4$: 322.2144. Found: 322.2146; [α]$_D^{20}$–57.8° (c 1.5, CH$_2$Cl$_2$).

Formula 404

To a stirred solution of pyrone 403a (1.30 g, 4.04 mmol) in 40 mL of anhydrous MeOH was added CeCl$_3$.7H$_2$O (904 mg, 2.43 mmol) at rt. After stirring for 10 min, the mixture was cooled to –40° C. and NaBH$_4$ (306 mg, 8.09 mmol) was added in one portion. The mixture was stirred for an additional 15 min before quenching with a 1:1 mixture of brine and H$_2$O. The aqueous layer was extracted with EtOAc (4×). The combined organics were washed with sat. NaHCO$_3$ and brine, dried over Na$_2$SO$_4$ and concentrated to afford a clear oil. Purification by flash chromatography (30% EtOAc/hexanes containing 1% Et$_3$N) afforded unstable allylic alcohol 404 (1.08 g, 82%) as a single diastereomer.

404: IR (film) 3386, 2951, 2869, 1643, 1456, 1380, 1307, 1268, 1231 cm$^{-1}$; $^1$H NMR (300 MHz, CDCl$_3$) δ6.35 (1H, br d, J=5.4 Hz), 4.75 (1H, ddd, J=1.9, 1.9, 6.1 Hz), 4.36–4.46 (1H, m), 4.08–4.17 (1H, m), 4.08 (1H, ddd, J=2.7, 12.4, 12.4 Hz), 3.98 (1H, dddd, J=2.7, 5.2, 7.9, 10.9 Hz), 3.81 (1H, ddd, J=1.5, 5.2, 11.5 Hz), 2.69 (1H, br d, J=13.5 Hz), 2.39 (1H, dsept, J=1.7, 6.9 Hz), 2.18 (1H, dddd, J=1.7, 1.9, 6.4, 13.0 Hz), 1.90 (1H, ddd, J=6.6, 7.7, 14.0 Hz), 1.33–1.74 (9H, m), 1.17 (1H, ddd, J=1.9, 4.4, 12.3 Hz), 0.90 (3H, d, J=6.2 Hz), 0.88 (6H, d, J=6.9 Hz), 0.69 (1H, t, J=12.7 Hz); $^{13}$C NMR (75 MHz, CDCl$_3$) δ145.3, 105.5, 100.6, 71.4, 64.3, 63.0, 58.9, 51.2, 41.5, 37.7, 37.4, 34.9, 31.3, 29.2, 24.2, 23.7, 22.2, 21.8, 18.8; [α]$_D^{20}$+2.00° (c 0.59, CHCl$_3$).

Formula 405

To a solution of 1.08 g (3.32 mmol) of allylic alcohol 404 in 66 mL of ethylvinylether was added mercury(II) trifluoroacetate (142 mg, 0.33 mmol) in a single portion at –10° C. The resulting colorless solution was stirred for 20 h at 5° C., diluted with Et$_2$O, washed with sat. NaHCO$_3$ and brine, dried over Na$_2$SO$_4$, and concentrated in vacuo to give a clear, colorless oil. Rapid flash chromatography (10% EtOAc/hexanes containing 1% Et$_3$N) afforded 865 mg (74%) of the corresponding allyl vinyl ether along with 208 mg (19%) of recovered 404. The vinyl ether was immediately dissolved in 100 mL n-nonane and heated at 145° C. for 3.5 h. The solution was cooled to 70–80° C. and the solvent was removed by short path distillation at reduced pressure. The remaining residue was purified by flash chromatography (10% EtOAc/hexanes) to provide Claisen product 405 (612 mg, 71%) as a colorless oil.

405: R$_f$ (30% EtOAc/hexanes)=0.75; IR (film) 2950, 2869, 1728, 1646, 1456, 1373, 1307, 1267 cm$^{-1}$; $^1$H NMR (300 MHz, CDCl$_3$) δ9.78 (1H, t, J=2.4 Hz), 5.89 (1H, dddd, J=2.0, 2.0, 4.7, 10.0 Hz), 5.64 (1H, dddd, J=1.3, 1.3, 2.5, 10.0 Hz), 4.57–4.66 (1H, m), 4.08 (1H, ddd, J=2.7, 12.1, 12.1 Hz), 3.90–4.01 (1H, m), 3.66–3.82 (2H, m), 2.69 (1H, ddd, J=1.9, 3.0, 13.4 Hz), 2.55 (2H, dd, J=2.4, 6.2 Hz), 2.40 (1H, dsept, J=1.6, 6.9 Hz), 1.12–2.14 (12H, m), 0.89 (3H, d, J=6.6 Hz), 0.88 (6H, d, J=7.1 Hz), 0.68 (1H, t, J=12.9 Hz); $^{13}$C NMR (75 MHz, CDCl$_3$) δ201.7, 128.5, 126.3, 100.5, 70.6, 70.5, 64.4, 59.1, 51.2, 48.5, 42.5, 37.4, 34.9, 31.5, 30.7, 29.1, 24.3, 23.7, 22.2, 21.9, 18.9; MS (EI) 350 (51), 335 (45), 322 (14), 293 (65), 279 (15), 265 (52), 255 (15), 139 (17), 135 (29), 97 (28), 83 (43), 81 (100), 79 (17), 69 (27), 67 (24); HRMS Calcd for C$_{21}$H$_{34}$O$_4$: 350.2457. Found: 350.2466; [α]$_D^{27}$ 0° (CH$_2$Cl$_2$).

Formula 406

To a stirred mixture of trimethylsilyl diethylphosphonoacetate (72 µL, 76.7 mg, 0.286 mmol) in anhydrous THF (1 mL) was added of n-butyllithium (2.5 M in hexanes, 109 µL, 0.272 mmol) dropwise at −78° C. After stirring for 20 min at −78° C. and 15 min at rt, the mixture was cooled to −78° C. and treated with a THF solution (1 mL) of aldehyde 405 (45 mg, 0.129 mmol). The mixture was allowed to warm to rt over 2 h and stirring was continued for 1 h. The mixture was diluted with 50 mL EtOAc and acidified with 10 mL of a 0.1 N aqueous NaHSO$_4$ solution. The phases were separated and the aqueous phase was extracted with EtOAc (3×). The combined organic extracts were washed with brine, dried over MgSO$_4$, and concentrated to give a colorless oil. Rapid filtration through a short pad of silica gel (20% acetone/benzene) gave a crude product which was dissolved in 2 mL methanol. Palladium on activated charcoal (10%, ~5 mg) was added and the mixture was stirred at room temperature for 18 h under balloon pressure of hydrogen gas. Filtration through Celite™ and flash chromatography on silica gel (40% EtOAc/hexanes containing 1% acetic acid) gave 21.8 mg (0.055 mmol, 43%) of ketal carboxylic acid 406 as a clear, colorless oil. R$_f$ (40% EtOAc/hexanes+1% AcOH) 0.44; IR (film) 3500–2500, 2938, 2868, 1711, 1456, 1377, 1307, 1268, 1158, 1113 cm$^{-1}$; $^1$H NMR (300 MHz, CDCl$_3$) δ4.08 (ddd, 1 H, J=2.6, 12.4, 12.4 Hz), 3.98 (dddd, 1 H, J=2.4, 6.6, 6.6, 10.7 Hz), 3.81 (ddd, 1 H, J=1.2, 5.2, 11.5 Hz), 3.38–3.47 (m, 1 H), 3.21–3.31 (m, 1H), 2.70 (br d, 1 H, J=12.5 Hz), 2.29–2.47 (m, 3 H), 1.62–1.86 (m, 5 H), 1.34–1.62 (m, 11 H), 1.07–1.30 (m, 3H), 0.78–0.98 (m, 1 H), 0.88 (d, 6 H, J=7.2 Hz), 0.88 (d, 3 H, J=7.0 Hz), 0.67 (t, 1 H, J=12.9 Hz); $^{13}$C NMR (75 MHz, CDCl$_3$) δ179.1, 100.5, 74.2, 64.6, 59.2, 51.2, 42.9, 37.3, 35.4, 34.9, 33.7, 31.50, 31.46, 31.3, 29.0, 24.2, 23.7, 23.6, 22.2, 21.8, 20.9, 18.8; HRMS Calcd for C$_{23}$H$_{40}$O$_5$: 396.2876. Found: 396.2870; [α]$^{23}_D$−10.5° (c 1.66, CHCl$_3$).

2B. Ketal Acid 408

Formula 407

To a solution of the aldehyde 405 (Example 2A, 274 mg, 0.778 mmol) in ethyl acetate (5 mL) was added Pd/C (10 mg) and the atmosphere was exchanged to hydrogen, which was applied for 30 min. The mixture was filtered and concentrated to give the corresponding crude saturated aldehyde, which was directly used in the next step.

A stock solution of Ipc$_2$B(allyl) was prepared by first dissolving (−)-Ipc$_2$BOMe (700 mg, 2.22 mmol) in ether (4.15 mL) at 0° C. and adding 1M allyl magnesium bromide (1.78 mL, 1.78 mmol). The mixture was warmed to rt and stirred for 30 min. In a separate flask, the aldehyde was dissolved in ether (4 mL) and treated with the stock solution of Ipc$_2$B(allyl) (0.3 M, 3.9 mL, 1.17 mmol) at −78° C. After stirring for 2 h at −78° C., the mixture was treated with hydrogen peroxide (30%, 2 mL) and sodium hydroxide (15%, 2 mL) and warmed to rt. After another 2 h, the mixture was partitioned between ethyl acetate and brine. The aqueous layer was extracted with ethyl acetate. The combined organic layers were dried over sodium sulfate, and concentrated to give the corresponding crude homoallylic alcohol, which was directly used in the next step.

To a solution of the crude homoallylic alcohol alcohol in methylene chloride (5 mL) at 0° C. was added TBSOTf (534 µL, 2.33 mmol) and diisopropyl ethyl amine (676 µL, 3.89 mmol) and stirred for 30 min. The mixture was directly loaded onto silica gel and purified to give the corresponding alkene (237 mg, 60% in 3 steps).

To a solution of the alkene (10 mg, 0.0197 mmol) in tert-butanol (1 mL) at rt was added a solution of KMnO$_4$ (0.6 mg, 0.0039 mmol) and NaIO$_4$ (17 mg, 0.0788 mmol) in water (buffered pH 7, 1 mL). After 30 min, the reaction mixture was quenched with sodium thiosulfate. The mixture was partitioned between ethyl acetate and brine. The aqueous layer was extracted with ethyl acetate. The combined organic layers were dried over sodium sulfate, and concentrated. Column chromatography afforded TBS ether 407 (6.3 mg, 71%).

407: R$_f$=0.20 (25% ethyl acetate/exane); [α]$^{25}_D$=22.6° (c 0.58, CH$_2$Cl$_2$); IR (neat)=2933, 1712, 1457, 1255, 1114 cm$^{-1}$; $^1$H NMR (400 MHz, CDCl$_3$) δ4.32 (m, 1 H), 4.08 (m, 1 H), 3.93 (m, 1 H), 3.81 (m, 1 H), 3.44 (m, 2 H), 2.69 (d, J=13.2 Hz, 1 H), 2.62 (dd, J=15.2, 5.2 Hz, 1 H), 2.48 (dd, J=15.2, 5.2 Hz, 1 H), 2.40 (quint, J=6.8 Hz, 1 H), 1.85–1.15 (m, 20 H), 0.88 (br s, 18 H), 0.12 (s, 3 H), 0.11 (s, 3 H); $^{13}$C NMR (100 MHz, CDCl$_3$) δ173.48, 100.44, 73.88, 73.52, 66.15, 64.26, 59.14, 51.24, 43.89, 43.25, 42.48, 37.43, 43.97, 32.13, 31.89, 30.93, 29.23, 25.74, 24.31, 23.77, 23.52, 22.25, 21.89, 19.15, 17.92, −4.77; HRMS: calcd for (C$_{29}$H$_{54}$O$_6$Si)=526.3689; found (M)=526.3687

Formula 408

To a solution of TBS ether 407 (9.3 mg, 0.0177 mmol) in THF (0.5 mL) at rt was added pyridine (127 µL) and HF pyridine (51 µL, 1.77 mmol) and stirred for 18 h. The mixture was partitioned between ethyl acetate and water (pH 4). The aqueous layer was extracted with ethyl acetate. The combined organic extracts were dried over sodium sulfate, concentrated in vacuo and the resulting crude hydroxy acid was used in the next step without further purification.

To a solution of crude hydroxy acid in methylene chloride (1.5 mL) at rt was added TESCl (26 µL, 0.0708 mmol) and TEA (19 µL, 0.142 mmol) and the mixture was stirred for 4 h. The mixture was treated with water (pH 4, 1 mL) and stirred for another 10 min. The aqueous layer was extracted with ethyl acetate. The combined organic extracts were dried over sodium sulfate and then concentrated. The crude product was purified by silica gel chromatography to give the TES acid 408 (7 mg, 75%—2 steps).

408: R$_f$=0.30 (33% ethyl acetate in hexane); [α]$^{25}_D$=34.00 (c 0.42, CH$_2$Cl$_2$); IR (film)=2951, 1711, 1457, 1378, 1114, 1005, 976 cm$^{-1}$; $^1$H NMR (400 MHz, CDCl$_3$) δ4.33 (m, 1 H), 4.09 (m, 1 H), 3.95 (m, 1 H), 3.81 (m, 1 H), 3.45 (m, 1 H), 2.70 (d, J=14 Hz, 1 H), 2.64 (dd, J=15.6, 5.2 Hz, 1 H), 2.51 (dd, J=15.6, 5.2 Hz, 1 H), 2.40 (m, 1 H), 1.86–1.15 (m, 21 H), 0.98 (t, J=8.0 Hz, 9 H), 0.89 (m, 9 H), 0.66 (q, J=8.0 Hz, 6 H); $^{13}$C NMR (100 MHz, CDCl$_3$) δ173.06, 100.45, 73.94, 73.70, 66.33, 64.28, 59.12, 51.21, 43.90, 43.23, 42.48, 37.40, 34.96, 32.12, 31.86, 31.00, 29.20, 24.33, 23.77, 23.52, 22.23, 21.89, 19.00, 6.79, 4.73; HRMS: calcd for (C$_{29}$H$_{54}$O$_6$Si)=526.3689; found (M)=526.3717.

2C. 9-Hydroxy-9-t-Butyl L3 Linker Synthon 504

Formula 501

To a solution of aldehyde 402 (Example 2A supra, 803 mg, 3.16 mmol) in ether (10 mL) was added a solution of 4-pentenyl magnesium bromide (0.8M in ether, 4.74 mL, 3.79 mmol) at −78° C. and the mixture was stirred for 30 min. The reaction was quenched with aq. sat. NH$_4$Cl (10 mL) and allowed to warm to rt. The mixture was then extracted with EtOAc (3×10 mL) and the combined organics were dried over MgSO$_4$, and concentrated in vacuo. The resulting residue was dissolved in CH$_2$Cl$_2$ (15 mL) and Dess-Martin Periodinane (2.02 g, 4.74 mmol) was added at rt. After 3 hours, sat. aq. Na$_2$SO$_3$ (10 mL) and sat. aq. NaHCO$_3$ (10 mL) was added. The mixture was extracted with CHCl$_3$ (3×10 mL), washed with sat. aq. NaHCO$_3$ (10 mL), dried over MgSO$_4$, and concentrated in vacuo. The residue was purified by column chromatography (90% EtOAc/hexane) to obtain ketone 501 (730 mg, 71.6%) as a colorless oil. 501: IR (film) 2957, 2362, 1716, 1637 cm$^{-1}$; $^1$H NMR (300 MHz, CDCl$_3$) δ, 0.62–0.92 (11H, m), 1.12–1.70 (9H, m) 2.03 (2H, dd, J=14.77, 7.63 Hz), 2.24–2.71 (6H, m), 3.79 (1H, ddd, J=11.53, 5.22,1.37 Hz), 4.10 (1H, td, J=11.88, 2.81 Hz), 4.224.31 (1H, m), 4.94–5.03 (2H, m), 5.68 (1H, m); $^{13}$C NMR (75 MHz, CDCl$_3$) δ, 18.82, 21.70, 22.13, 22.37, 23.62, 24.18, 28.59, 31.34, 32.95, 34.76, 37.32, 43.73, 49.33, 51.09, 58.81, 65.39, 100.73, 115.21, 138.04, 209.56; HRMS (EI) Calc'd. for C$_{20}$H$_{34}$O$_3$: 322.2508. Found: 322.2497. $[α]_D^{25}$=5.520° (c 4.79, CH$_2$Cl$_2$).

502.1 (Formula 502 Where R$^8$ is t-butyl)

To a solution of ketone 501 (35 mg, 0.109 mmol) in ether (0.6 mL) was added t-BuLi (1.6 M in pentane, 75 μL, 0.12 mmol) dropwise at −78° C. The mixture was stirred at rt for 30 min. and then quenched with sat. aq. NH$_4$Cl (2 mL). The mixture was allowed to warm to rt and was then extracted with EtOAc (3×5 mL). The combined organics were washed with brine, dried over Na$_2$SO$_4$, and concentrated in vacuo. Chromatography (10% EtOAc/hexane) afforded a major diastereomer A31a (17.5 mg, 42%) along with a minor diastereomer A31b. (7.4 mg, 18%) as colorless oils (structures not shown). A31a: IR (film): 2956, 1639, 1456 cm$^{-1}$; $^1$H NMR (400 MHz, CDCl$_3$) δ, 0.73 (1H, t, J=12.88 Hz), 0.89–0.94 (18H, m), 1,17–1.76 (14H, m), 2.00–2.09 (2H, m), 2.38–2.42 (1H, m), 2.73 (1H, d, J=13.73 Hz), 3.47 (1H, s), 3.79 (1H, dd, J=11.60, 5.06 Hz), 4.12 (1H, td, J=11.97, 2.44 Hz), 4.25–4.29 (1H, m), 4.91 (1H, d, J=10.17 Hz), 4.98 (1H, d, J=17.63 Hz), 5.77–5.84 (1H, m); 13C NMR (75 MHz, CDCl$_3$) δ19.07, 22.20, 22.25, 23.15, 23.45, 24.66, 25.43, 25.52, 28.98, 31.80, 34.36, 34.51, 34.60, 36.84, 37.54, 39.29, 39.63, 51.30, 58.92, 67.73, 79.0, 101.26, 114.31, 139.03; HRMS (EI) Calc'd. for C$_{24}$H$_{44}$O$_3$: 380.3290. Found: 380.3281. $[α]_D^{25}$=5.89° (c 0.85, CDCl$_3$).

To a solution of major diastereomer A31a (332 mg, 0.872 mmol) in THF (5 mL) was added KHMDS (0.5M in toluene, 5.24 mL, 2.62 mmol) in an ice bath. TMSCl (284 mg, 2.62 mmol) was added and the mixture was stirred for 30 minutes. The mixture was quenched with sat. aq. NH$_4$Cl (5 mL) and extracted with EtOAc (3×5 mL). The combined organics were washed with brine (5 mL), dried over MgSO$_4$, and then concentrated in vacuo. Chromatography (5% EtOAc/hexane) providing 502.1 (395 mg, 100%) as a white solid. 502.1: m.p.=60.0° C.; IR (film) 2953, 1642, 1455 cm$^{-1}$; $^1$H NMR (300 MHz, CDCl$_3$) δ, 0.132 (6H, s), 0.134 (3H, s), 0.67–1.71 (33H, m), 1.95–1.99 (2H, m), 2.36–2.46 (1H, m), 2.71 (1H, app d, J=14.3 Hz), 3.74–3.79 (1H, m), 3.88–3.94 (1H, m), 4.07 (1H, td, J=11.75, 2.96 Hz), 4.95 (1H, d, J=10.41 Hz), 5.00 (1H, d, J=17.33 Hz), 5.74–5.85 (1H, m); $^{13}$C NMR (75 MHz, CDCl$_3$) δ2.9, 5.3, 18.9, 21.7, 22.2, 23.8, 24.3, 25.3, 26.2, 29.1, 34.2, 34.8, 35.0, 37.6, 39.2, 40.0, 51.3, 59.3, 65.6, 82.9, 100.7, 114.6, 138.7; HRMS (EI) Calc'd. for C$_{27}$H$_{52}$O$_3$Si: 452.3686. Found: 452.3670; $[α]_D^{26}$=−11.33° (c 1.56, CDCl$_3$).

503.1 (Formula 503 Where R$^8$ is t-butyl)

To a solution of 502.1 (98 mg, 0.216 mmol) in CH$_2$Cl$_2$ (8 mL) and MeOH (0.5 mL) was bubbled O$_3$ at −78° C. until a blue color persists. Nitrogen gas was then used to purge the system and (EtO)$_3$P (54 mg, 0.324 mmol) was subsequently added. The mixture was stirred for 3 h and then slowly warmed to rt. Sat. aq. Na$_2$SO$_3$ (10 mL) was added and the mixture was extracted with CHCl$_3$ (3×10 mL). The combined organics were then washed with brine (10 mL), dried over MgSO$_4$ and concentrated in vacuo. Chromatography (0.5% EtOAc/hexane) afforded 503.1 (63 mg, 64.1%) as a colorless oil. 503.1: IR (film) 2941, 1715, 1454 cm$^{-1}$; $^1$H NMR (400 MHz, CDCl$_3$) δ0.134 (9H, s), 0.73 (1H, t, J=13.13 Hz), 0.9–1.81 (32H, m), 2.34–2.42 (3H, m), 2.72 (1H, d, J=12.29 Hz), 3.77 (1H, dd, J=11.59, 4.58 Hz), 3.92–3.96 (1H, m), 4.08 (1H, td, J=12.28, 2.01 Hz), 9.77 (1H, s); $^{13}$C NMR (100 MHz, CDCl$_3$) δ, 3.39, 18.98, 19.29, 22.60, 24.23, 24.71, 26.75, 29.76, 34.41, 35.15, 37.77, 38.01, 39.66, 42.95, 45.26, 51.67, 59.64, 65.90, 83.08, 100.99, 202.26; HRMS (EI) Calc'd. for C$_{26}$H$_{50}$O$_4$Si: 454.3478. Found: 452.3475; $[α]_D^{27}$=−6.330° (c 2.9, CH$_2$Cl$_2$).

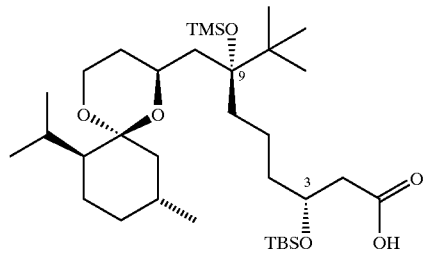

504.1 (Formula 504 Where R$^8$ is t-butyl)

To (−)-Ipc$_2$BOMe (108.8 mg, 0.34 mmol) (weighed in an inert atmosphere) was added diethyl ether (340 μL). The flask was cooled to −78° C. and allylmagnesium bromide (1.0 M, 310 μL, 0.31 mmol) was added. The precipitous mixture was stirred for 15 min. at −78° C. and then slowly warmed to rt and stirred for 1 hour. Diethyl ether (340 mL) was added and then a pre-cooled solution of aldehyde 503.1 (40.1 mg, 0.109 mmol) in diethyl ether (160 μL) was added dropwise. The suspension was stirred for 1 h, then the temperature was slowly raised to rt and 3N NaOH (240 μL), 30% hydrogen peroxide (100 μL) and diethyl ether (400 μL) was added. The biphasic mixture was refluxed for 1 h and then quenched with water (9 mL) and extracted with ethyl acetate (4×10 mL). The combined organics were washed with brine (10 mL), dried over sodium sulfate and the solvent was removed in vacuo. Chromatography on silica gel (12.5% EtOAc/hexane) afforded the crude homoallylic alcohol as a yellow oil. To this oil in methylene chloride (500 μL) was added imidazole (19 mg, 0.276 mmol) and TBSCl (21 mg, 0.138 mmol). The reaction was sealed and stirred for 14 h. The reaction was then quenched with a saturated solution of sodium bicarbonate (2 mL) and extracted with ethyl acetate (3×5 mL). The combined organics were washed with brine (5 mL), dried over sodium sulfate, filtered and the solvent was removed in vacuo. Filtration over silica gel (5% EtOAc/hexane) afforded a crude silyl ether A34 as a yellow oil (structure not shown). A34: IR (film) 2956, 1644, 1462 cm$^{-1}$; $^1$H NMR (400 MHz, CDCl$_3$) δ0.05 (6H, s), 0.05 (9H, s), 0.7–1.70 (42H, m), 2.21 (2H, d, J=6.48 Hz), 2.38–2.44 (2H, m), 2.72 (2H, d, J=13.36 Hz), 3.71 (1H, t, J=5.43 Hz), 3.77 (1H, dd, J=11.53, 3.59 Hz), 3.88–3.93 (1H, m), 4.07 (1H, td, J=11 91, 3.06 Hz), 5.02 (1H, s), 5.06 (1H, d, J=3.66 Hz), 5.77–5.88 (1H, m); $^{13}$C NMR (100 MHz, CDCl$_3$) δ−4.06, 3.39, 19.38, 21.48, 22.23, 22.72, 24.25, 24.78, 26.27, 26.69, 29.52, 34.58, 35.25, 38.06, 38.38, 38.50, 39.68, 42.02, 43.11, 59.68, 51.72, 65.98, 72.08, 83.20, 100.98, 117.06, 135.66; $[\alpha]_D$=−4.180° (c 1.0, CDCl$_3$).

To crude silyl ether A34 in t-butanol (2.3 mL), water (1.4 mL) and pH 7 phosphate buffer (465 μL) was added NaIO$_4$ (79 mg, 0.368 mmol) followed by KMnO$_4$ (2.9 mg, 0.0184 mmol). The purple solution was stirred for 3 h and then water (3 mL) was added. This mixture was then extracted with ethyl acetate (4×5 mL) and the combined organics were washed with brine (5 mL), dried over sodium sulfate and filtered. The solvent was removed in vacuo and chromatography on silica gel (12.5% EtOAc, 0.1% acetic acid/hexanes) afforded acid 504.1 as well as the β-C3 diastereomeric alcohol. 504.1: IR (film): 3433, 2956, 1712, 1461 cm$^{-1}$; $^1$H NMR (400 MHz, CDCl$_3$) δ0.08 (3H, s), 0.09 (3H, s), 0.13 (6H, s), 0.70–1.70 (48H, m), 2.35–2.55 (3H, m), 2.72 (1H, d, J=12.74 Hz), 3.78 (1H, dd, J=11.34, 3.97 Hz,), 3.90–3.92 (1H, m), 4.75 (1H, dd, J=12.45, 11.97 Hz), 4.15 (1H, t, J=4.89 Hz); $^{13}$C NMR (100 MHz, CDCl$_3$) δ −4.53, −4.10, 3.39, 18.32, 19.39, 21.29, 22.29, 22.66, 24.23, 24.75, 26.12, 26,72, 29.64, 34.49, 35.19, 38.04, 38.38, 38.81, 39.71, 42.11, 43.08, 51.67, 59,65, 65.93, 69.51, 83.10, 101.01, 176.69; $[\alpha]_D^{28}$=−8.19° (c 2.70, CDCl$_3$).

2D. 9-t-Butyl L4 Linker Synthon 508

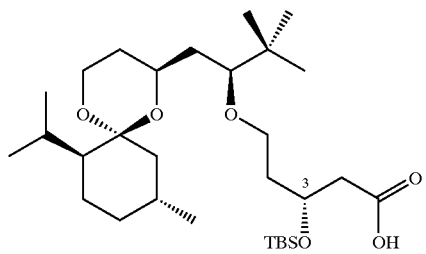

508.1 (Formula 508 where $R^8$ is t-butyl)

To (−)-Ipc$_2$BOMe (108.8 mg, 0.34 mmol) (weighed in an inert atmosphere) was added diethyl ether (340 μL). The flask was cooled to −78° C. and allylmagnesium bromide (1.0 M, 310 μL, 0.31 mmol) was added. The precipitous mixture was stirred for 15 min. at −78° C. and then slowly warmed to rt and stirred for 1 hour. Diethyl ether (340 mL) was added and then a pre-cooled solution of an aldehyde 506(0.109 mmol) (structure not shown) prepared as described for compound 10 in Wender et al. (1998c) in diethyl ether (160 μL) was added dropwise. The suspension was stirred for 1 h, then the temperature was slowly raised to rt and 3N NaOH (240 μL), 30% hydrogen peroxide (100 μL) and diethyl ether (400 μL) was added. The biphasic mixture was refluxed for 1 h and then quenched with water (9 mL) and extracted with ethyl acetate (4×10 mL). The combined organics were washed with brine (10 mL), dried over sodium sulfate and the solvent was removed in vacuo. Chromatography on silica gel (12.5% EtOAc/hexane) afforded the crude homoallylic alcohol as a yellow oil. To this oil in methylene chloride (500 μL) was added imidazole (19 mg, 0.276 mmol) and TBSCl (21 mg, 0.138 mmol). The reaction was sealed and stirred for 14 h. The reaction was then quenched with a saturated solution of sodium bicarbonate (2 mL) and extracted with ethyl acetate (3×5 mL). The combined organics were washed with brine (5 mL), dried over sodium sulfate, filtered and the solvent was removed in vacuo. Filtration over silica gel (5% EtOAc/hexane) afforded a crude silyl ether as a yellow oil. To this oil in t-butanol (2.3 mL), water (1.4 mL) and pH 7 phosphate buffer (465 μL) was added NaIO$_4$ (79 mg, 0.368 mmol) followed by KMnO$_4$ (2.9 mg, 0.0184 mmol). The purple solution was stirred for 3 h and then water (3 mL) was added. This mixture was then extracted with ethyl acetate (4×5 mL) and the combined organics were washed with brine (5 mL), dried over sodium sulfate and filtered. The solvent was removed in vacuo and chromatography on silica gel (12.5% EtOAc, 0.1% acetic acid/hexanes) afforded acid 508.1 (34 mg, 56%) as a colorless oil. 508.1: Rf (15% ethyl acetate/hexanes)=0.17; IR (film) 2700–3300, 2954, 2869, 1713, 1107, 837, 776 cm$^{-1}$; $^1$H NMR (300 MHz, CDCl$_3$) δ0.08 (6H, s), 0.69 (1H, t, J=13.1 Hz), 0.76–0.90 (27H, m), 1.17–1.25 (3H, m), 1.39–1.61 (6H, m), 1.70–1.82 (3H, m), 2.40 (1H, dsept, J=7.2, 0.9 Hz), 2.58 (1H, dd, J=13.1, 5.6 Hz), 2.68 (1H, br d, J=12.6 Hz), 2.91 (1H, t, J=4.8 Hz), 3.41 (1H, dd, J=5.9, 2.3 Hz), 3.63–3.77 (2H, m), 3.82 (1H, dd, J=11.7, 4.2 Hz), 4.066 (1H, td, J=12.0, 2.7 Hz), 4.23–4.29 (1H, m), 9.20–9.40 (1H, br s); $^{13}$C NMR (100 MHz, C$_6$D$_6$) δ −5.1, −4.8, 17.8, 18.9, 21.9, 22.1, 23.7, 24.3, 25.6, 26.0, 29.1, 31.8, 34.9, 35.7, 37.3, 38.7, 41.8, 51.3, 59.2, 66.6, 66.9, 67.2, 84.5, 174.7; HRMS (FAB) Calc'd. for C$_{30}$H$_{58}$O$_6$Si: 542.4002, Found: 542.4005; $[\alpha]_D^{22}$=−5.88° (c 1.67, CH$_2$Cl$_2$).

2E. Linker Synthon 507

To (−)-Ipc$_2$BOMe (108.8 mg, 0.34 mmol) (weighed in an inert atmosphere) was added diethyl ether (340 μL). The flask was cooled to −78° C. and allylmagnesium bromide (1.0 M, 310 μL, 0.31 mmol) was added. The precipitous mixture was stirred for 15 min. at −78° C. and then slowly warmed to rt and stirred for 1 hour. Diethyl ether (340 mL) was added and then a pre-cooled solution of an aldehyde 506 (0.109 mmol) (structure not shown) prepared as described for compound 9 in Wender et al. (1998c) in diethyl ether (160 μL) was added dropwise. The suspension was stirred for 1 h, then the temperature was slowly raised to rt and 3N NaOH (240 μL), 30% hydrogen peroxide (100 μL) and diethyl ether (400 μL) was added. The biphasic mixture was refluxed for 1 h and then quenched with water (9 mL) and extracted with ethyl acetate (4×10 mL). The combined organics were washed with brine (10 mL), dried over sodium sulfate and the solvent was removed in vacuo. Chromatography on silica gel (12.5% EtOAc/hexane) afforded the crude homoallylic alcohol A40 (structure not shown) as a yellow oil. Rf (35% ethyl acetate/hexanes)= 0.65; IR (film) 3455, 2950, 2868, 1456, 1373, 1308, 1265, 1110, 997 cm$^{-1}$; $^1$H NMR (300 MHz, CDCl$_3$) δ0.68 (1H, t, J=13.5 Hz), 0.83–0.92 (10H, m), 1.39–1.52 (5H, m), 1.57–1.72 (3H, m), 1.71 (1H, d, J=4.9 Hz), 2.24 (1H, t, J=4.9 Hz), 2.35–2.42 (2H, m), 2.70 (3H, br d, J=12.4 Hz), 3.46–3.60 (3H, m), 3.62–3.70 (1H, m), 3.77–3.95 (3H, m), 4.11 (1H, dd, J=11.9, 2.7 Hz), 5.07 (2H, dd, J=9.5, 1.9 Hz), 5.70–5.91 (1H, m); $^{13}$C NMR (100 MHz, CDCl$_3$) δ13.9, 16.4, 17.5, 21.1, 22.0, 23.1, 29.1, 30.7, 31.1, 31.8, 33.7, 37.3, 46.1, 51.1, 56.9, 64.7, 65.0, 66.8, 113.3, 129.3; $[\alpha]_D^{20}$=2.5° (c 0.8, CDCl$_3$).

To A40 in methylene chloride (500 μL) was added imidazole (19 mg, 0.276 mmol) and TBSCl (21 mg, 0.138 mmol). The reaction was sealed and stirred for 14 h. The reaction was then quenched with a saturated solution of sodium bicarbonate (2 mL) and extracted with ethyl acetate (3×5 mL). The combined organics were washed with brine (5 mL), dried over sodium sulfate, filtered and the solvent was removed in vacuo. Filtration over silica gel (5% EtOAc/hexane) afforded a crude silyl ether A41 (structure not shown) as a yellow oil. Rf (35% ethyl acetate/hexanes)= 0.65; IR (film): 2953, 2864, 1641, 1472, 1372, 1255, 1108, 830 cm$^{-1}$; $^1$H NMR (300 MHz, CDCl$_3$) δ0.05 (3H, s), 0.05 (3H, s), 0.67 (1H, t, J=13.5 Hz), 0.81–0.96 (18H, m), 1.11–1.20 (1H, m), 1.35–1.47 (4H, m), 1.52–1.71 (5H, m), 2.22 (1H, br s), 2.35–2.42 (2H, m), 2.70 (3H, br d, J=12.2 Hz), 3.38–3.54 (4H, m), 3.78–3.97 (3H, m), 4.10 (1H, dd, J=11.9, 2.8 Hz), 5.05 (2H, dd, J=9.4, 1.8 Hz), 5.69–5.91 (1H, m); $^{13}$C NMR (100 MHz, CDCl$_3$) δ–9.5, –9.1, 13.3, 14.1, 17.1, 17.5, 18.9, 19.5, 21.1, 24.1, 27.0, 30.2, 31.8, 32.0, 32.6, 37.5, 46.4, 54.4, 59.5, 61.9, 62.8, 64.1, 95.6, 112.0, 130.0; [α]$_D^{20}$=16.2° (c 1.0, CH$_2$Cl$_2$).

To A41 in t-butanol (2.3 mL), water (1.4 mL) and pH 7 phosphate buffer (465 μL) was added NaIO$_4$ (79 mg, 0.368 mmol) followed by KMnO$_4$ (2.9 mg, 0.0184 mmol). The purple solution was stirred for 3 h and then water (3 mL) was added. This mixture was then extracted with ethyl acetate (4×5 mL) and the combined organics were washed with brine (5 mL), dried over sodium sulfate and filtered. The solvent was removed in vacuo and chromatography on silica gel (12.5% EtOAc, 0.1% acetic acid/hexanes) afforded acid 507. IR (film): 2700–3300, 2952, 2866, 1738, 1471, 1373, 1307, 1146, 1103, 837, cm$^{-1}$; $^1$H NMR (300 MHz, CDCl$_3$) δ0.06 (3H, s), 0.07 (3H, s), 0.67 (1H, app t, J=13.1 Hz), 0.81–0.89 (19H, m), 1.14–1.20 (1H, m), 1.35–1.47 (5H, m), 1.50–1.82 (4H, m), 2.34–2.41 (1H, m), 2.45–2.53 (2H, m), 2.69 (3H, br d, J=13.7 Hz), 3.44–3.51 (4H, m), 3.80 (1H, dd, J=11.5, 3.9 Hz), 3.87–3.95 (1H, m), 4.02–4.09 (1H, m), 4.22–4.29 (1H, m); $^{13}$C NMR (100 MHz, CDCl$_3$) δ–9.6, 13.1, 14.1, 17.1, 17.5, 18.9, 19.5, 20.9, 24.2, 26.9, 30.1, 32.0, 32.3, 32.6, 37.7, 46.4, 54.3, 59.6, 61.9, 62.1, 95.7, 171.5; HRMS (FAB) Calc'd. for C$_{26}$H$_{50}$O$_6$Si: 486.3379, Found: 486.3377; [α]$_D^{20}$=9.4° (c 1.3, CH$_2$Cl$_2$).

2F. Ether Diester Linker Synthon 606

The following procedure, referred to as the "general isolation procedure", was used to purify various reaction products below. The reaction mixture is quenched by dropwise addition of saturated aqueous ammonium chloride, and the resultant mixture is allowed to partition between solvent and brine or water. The aqueous layer is extracted with 1 to 3 portions of ethyl acetate. The combined organic extracts are dried over sodium sulfate and concentrated in vacuo.

Formula 602

To a solution of 3-(p-methoxybenzyloxy)propyl allyl ether 601 (1.0 g, 4.3 mmol) in THF (10 mL) was added 9-BBN (20.6 mL of 0.5 M solution in THF, 10.3 mmol), and the mixture was stirred for 2 h at rt. Hydrogen peroxide (30%, 10 mL) and sodium hydroxide (15%, 10 mL) were added and the mixture was stirred for 3 h. The general isolation procedure afforded crude product which was purified further by silica gel chromatography to give the expected purified alcohol A51 (870 mg, 75%) (structure not shown). R$_f$=0.25 (50% ethyl acetate in hexane); IR (neat)= 3423, 2934, 2864, 1612, 1513, 1248, 1098 cm$^{-1}$; $^1$H NMR (300 MHz, CDCl$_3$) δ7.25 (d, J=8.7 Hz, 2 H), 6.87 (d, J=8.7 Hz, 2 H), 4.43 (s, 2 H), 3.80 (s, 3 H), 3.75 (q, J=5.7 Hz, 2 H), 3.60 (t, J=5.7 Hz, 2 H), 3.52 (m, 4 H), 2.46 (br t, 1 H), 1.84 (m, 4 H); $^{13}$C NMR (75 MHz, CDCl$_3$) δ129.36, 113.83, 72.63, 70.34, 68.33, 66.89, 62.20, 55.23, 31.88, 29.96.

To a solution of DMSO (1.38 mL, 19.5 mmol) in methylene chloride (5 mL) at –78° C. was added oxalyl chloride (850 μL, 9.74 mmol) dropwise. After 5 min, alcohol A51 from the preceding step (870 mg, 6.49 mmol) in methylene chloride (2 mL) was added and the mixture was stirred for another 20 min. TEA (triethylamine, 4.31 mL, 32.5 mmol) was added. After 10 min, the mixture was warmed to rt. The standard isolation procedure afforded the expected aldehyde 602 (760 mg, 89%). R$_f$=0.40 (33% ethyl acetate in hexane); IR (neat)=2863, 1724, 1612, 1513, 1248, 1098 cm$^{-1}$; $^1$H NMR (300 MHz, CDCl$_3$) δ9.75 (s, 1 H), 7.25 (d, J=9.0 Hz, 2 H), 6.87 (d, J=9.0 Hz, 2 H), 4.42 (s, 2 H), 3.80 (s, 3 H), 3.74 (t, J=6.0 Hz, 2 H), 3.51 (m, 4 H), 2.62 (m, 2 H), 1.84 (quint, J=6.3 Hz, 2 H); $^{13}$C NMR (75 MHz, CDCl$_3$) δ201.49, 159.26, 130.65, 129.31, 113.78, 72.57, 68.08, 66.69, 64.40, 55.19, 43.75, 29.86.

Formula 603

(–)-Ipc$_2$BOMe (1.91 g, 6.04 mmol) in ether (4 mL) was treated with allylmagnesium bromide (4.83 mL, 4.83 mmol) at rt. After 30 min, the mixture was cooled to –78° C. The aldehyde 602 (370 mg, 2.76 mmol) in ether (1.5 mL) was added and stirred for 2 h at –78° C. 15% NaOH (1.5 mL) and 30% hydrogen peroxide (1.5 mL) were added and the mixture was warmed to rt. After 2 h, the mixture was diluted with ethyl acetate and washed with brine. Column chromatography yielded the expected alcohol A53 (383 mg, 80%) (structure not shown). Alcohol A53 (150 mg, 0.852 mmol) in methylene chloride (4 mL) was treated with TBSCl (168 mg, 1.11 mmol) and imidazole (116 mg, 1.7 mmol) at rt. After overnight, the reaction was worked up by the standard procedure. Column chromatography afforded expected TBS alkene ether 603 (195 mg, 79%). 603: R$_f$=0.50 (10% ethyl acetate in hexane); [α]$^{25}_D$=13.6° (c 1.08, CH$_2$Cl$_2$); IR (neat)=2952, 2856, 1717, 1613, 1513, 1471, 1362, 1248, 1110 cm$^{-1}$; $^1$H NMR (400 MHz, CDCl$_3$) δ7.26 (d, J=8.4 Hz, 2 H), 6.88 (d, J=8.4 Hz, 2 H), 5.81 (m, 1 H), 5.04 (m, 2 H), 4.43 (s, 2 H), 3.86 (s, 3 H), 3.49 (m, 7H), 2.23 (m, 2 H), 1.87 (m, 2 H), 1.69 (m, 2 H), 0.89 (s, 9 H), 0.06 (s, 3 H), 0.05 (s, 3 H); $^{13}$C NMR (100 MHz, CDCl$_3$) δ159.09, 134.96, 130.60, 116.93, 113.71, 72.59, 68.91, 67.80, 67.48, 67.18, 55.23, 42.28, 36.62, 30.16, 25.85, 18.08, –4.39, –4.76

Formula 605

Alkene ether 603 (195 mg, 0.672 mmol) in tert-butanol-water (pH 7) (1:1, 4 mL) was treated with KMnO$_4$ (11 mg, 0.0672 mmol) and sodium periodate (548 mg, 2.56 mmol) in water (0.5 mL). After 30 min, the reaction was quenched with sodium thiosulfate. The mixture was diluted with ethyl acetate. The organic layer was washed with brine, dried over sodium sulfate, and concentrated to give a crude acid 604. The crude acid in methylene chloride (3 mL) was treated with SEMCl (2-(trimethylsilyl)ethoxymethyl chloride, 301:L, 1.7 mmol) and TEA (452:L, 3.4 mmol) at rt and stirred for 2 h. The reaction was worked up by the standard procedure to afford the expected SEM ester 605.

SEM ester 605 in wet methylene chloride (3 mL) was treated with DDQ (291 mg, 1.28 mmol). After 1 h, the mixture was directly purified by silica gel chromatography to give the alcohol product 606 (86 mg, 29% for 3 steps). 606: R$_f$=0.25 (25% ethyl acetate in hexane); [α]$^{25}_D$=0.4° (c 0.82, CH$_2$Cl$_2$); IR (neat)=3458, 2955, 1741, 1472, 1378, 1250, 1116 cm$^{-1}$; $^1$H NMR (400 MHz, CDCl$_3$) δ5.25 (q, J=2.8 Hz, 2 H), 4.25 (quint, J=6.4 Hz, 2 H), 3.71 (m, 4 H), 3.52 (m, 4 H), 2.50 (d, J=6.0 Hz, 2 H), 2.44 (br, 1 H), 1.79 (m, 4 H), 0.94 (t, J=8.4 Hz, 2 H), 0.85 (s, 9 H), 0.05 (s, 3 H), 0.03 (s, 3 H), 0.00 (s, 9 H); $^{13}$C NMR (100 MHz, CDCl$_3$)

δ171.04, 88.97, 69.88, 67.88, 67.25, 66.45, 61.81, 42.84, 37.12, 32.02, 25.71, 17.97, 17.91, −1.48, −4.81, −4.86

2G. C5 Ester-Open C7 Linker Synthon 513

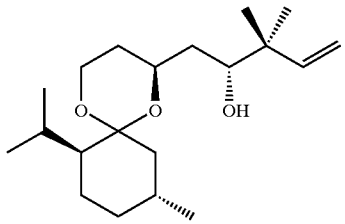
509a

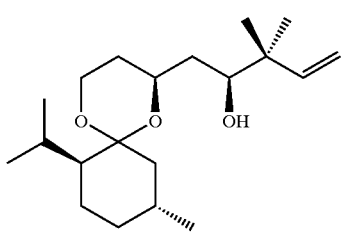
509b

To menthone aldehyde 402 (400 mg, 1.56 mmol) from Example 2A in DMF (12 mL) was added prenyl bromide (396 mg, 1.56 mmol) followed by indium powder (359 mg, 3.13 mmol) at rt. After 30 min., the reaction was diluted with EtOAc (20 mL) and saturated aqueous ammonium chloride (15 mL). The layers were separated and the aqueous layer was re-extracted with EtOAc (3×10 mL). The combined organics were washed with brine (15 mL) and dried over sodium sulfate. The solvent was removed in vacuo and chromatography (7.5% EtOAc/pentane) to afford 509a (105 mg, 21%) and 509b (321 mg, 63%).

Undesired isomer 509a can be recycled by the following procedure: To 509a (320.8 mg, 0.98 mmol) in methylene chloride (3 mL) was added Dess-Martin Periodinane (707 mg, 1.67 mmol) and stirred for 1 h at room temperature. The reaction was diluted with methylene chloride (3 mL), saturated sodium bicarbonate (3 mL) and sodium thiosulfate (3 mL) and stirred for 1 h. The layers were separated and the aqueous layer was re-extracted with EtOAc (4×5 mL). The combined organics were dried over sodium sulfate and the solvent was removed in vacuo. The crude ketone was dissolved in MeOH (17.3 mL) and $CeCl_3 \cdot 7H_2O$ (1.83 g, 4.9 mmol) was added and stirred for 5 min. The solution was cooled to −50° C. and $NaBH_4$ (74.5 mg, 19.6 mmol) was added. The reaction was stirred for 30 min. and then poured into a separatory funnel containing EtOAc (30 mL), water (18 mL) and brine (30 mL). The layers were separated and the aqueous layer was extracted with EtOAc (3×10 mL). The combined organics were dried over sodium sulfate and the solvent was removed in vacuo. Chromatography (7.5%–20% EtOAc/pentane) provided 509b (177 mg, 53%) and 509a (56 mg, 18%). 509a: $R_f$ (7.5% EtOAc/pentane)= 0.186; IR (film): 3496.8, 2953.9, 2869.6, 1458.0, 1374.4, 1308.3, 1266.5, 1157.8, 1130.7, 1102.0, 977.6, 912.2 cm$^{-1}$; $^1$H-NMR (300 MHz, CDCl$_3$) δ0.68 (1H, t, J=12.9 Hz), 0.85–0.89 (9H, m), 0.98 (3H, s), 0.99 (3H, s), 1.14–1.76 (10H, m), 2.38 (1H, sept, J=6.9 Hz), 2.73 (1H, br. d, J=13.5 Hz), 3.59 (1H, br. d, J=9.9 Hz), 3.78 (1H, dd, J=11.7, 5.4 Hz), 4.02 (1H, d, J=11.4), 4.11 (1H, d, J=13.2), 5.00–5.09 (2H, m), 5.81 (1H, dd, J=17.6, 11.0 Hz); $^{13}$C-NMR (75 MHz, CDCl$_3$) δ18.8, 21.7, 22.0, 22.4, 23.1, 23.8, 24.3, 29.1, 31.9, 34.9, 37.4, 38.5, 41.2, 51.2, 59.1, 64.5, 73.5, 100.4, 113.2, 145.4; HRMS calc'd for $C_{20}H_{36}O_3$: 324.2664; found: 324.2664; $[\alpha]^{24.0}_d$:+19.36° (c 8.16, CH$_2$Cl$_2$). 509b: $R_f$ (7.5% EtOAc/pentane)=0.37; IR (film): 3520.4, 2953.6, 2870.2, 1455.8, 1375.6, 1309.4, 1266.0, 1130.3, 1090.0, 973.3, 914.4 cm$^{-1}$; $^1$H-NMR (300 MHz, CDCl$_3$) δ0.73 (1H, t, J=13 Hz), 0.83–0.92 (9H, m), 1.00 (3H, s), 1.01 (3H, s), 1.18–1.77 (10H, m), 2.39 (1H, sept, J=7 Hz), 2.73 (1H, br. d, J=13.5 Hz), 3.53 (1H, d, J=9.9 Hz), 3.57(1H, s), 3.79 (1H, dd, J=11.7, 4.8 Hz), 4.00–4.15 (2H, m), 4.96–5.02 (2H, m), 5.87 (1H, dd, J=17.1, 11.1 Hz); $^{13}$C-NMR (75 MHz, CDCl$_3$) δ18.9, 21.9, 22.2, 22.3, 23.3, 23.8, 24.2, 28.9, 31.8, 34.6, 37.3, 38.0, 41.1, 50.9, 58.8, 70.3, 78.9, 101.0, 111.9, 145.7; HRMS calc'd for $C_{20}H_{36}O_3$: 324.2664; found: 324.2665; $[\alpha]^{25.1}_d$:−1.94° (c 9.75, CH$_2$Cl$_2$).

Formula 510

To a solution of 509b (282 mg, 0.87 mmol) in MeOH (3.3 mL) and methylene chloride (13 mL) at −78° C. was bubbled ozone for 5 min. or until a blue color persisted. The solution was then purged with nitrogen for 5 min. $NaBH_4$ (138 mg, 3.65 mmol) was then added and stirred for 1 h at −78° C., and 2 h at 0° C. Saturated ammonium chloride (15 mL) and water (5 mL) were then poured into the reaction and the layers were separated. The aqueous layer was extracted with methylene chloride (4×5 mL). The combined organics were dried over sodium sulfate and the solvent was removed in vacuo, yielding crude diol 510: $R_f$ (20% EtOAc/pentane)=0.195; IR (film): 3452.3, 2954.1, 2871.3, 1455.5, 1383.4, 1308.9, 1266.9, 1131.4, 1047.2, 972.6 cm$^{-1}$; $^1$H-NMR (300 MHz, CDCl$_3$) δ0.74 (1H, t, J=13 Hz), 0.85–0.89 (12H, m), 0.92 (3H, d, J=6.6 Hz), 1.12–1.25 (2H, m), 1.39–1.78 (7H, m), 2.39 (1H, sept, J=6.9 Hz), 2.73 (1H, br. d, J=13.5 Hz), 3.48 (3H, m), 3.70–3.73 (1H, m), 3.80 (1H, dd, J=11.4, 5.1 Hz), 4.08–4.15 (3H, m); $^{13}$C-NMR (75 MHz, CDCl$_3$) δ18.8, 19.0, 22.2, 22.3, 22.5, 23.7, 24.2, 29.0, 31.8, 34.5, 37.3, 37.6, 38.0, 50.9, 58.8, 70.6, 72.0, 80.5, 101.0; HRMS calc'd for $C_{19}H_{36}O_4$: 328.2614; found: 328.2619; $[\alpha]^{26.0}_d$:−0.78° (c 5.48, CH$_2$Cl$_2$).

Formula 511

To crude diol 510 was added pyridine (316 μL, 3.91 mmol) and chloroacetic anhydride (229 mg, 1.3 mmol) at −78° C. and stirred for 2 hr. Saturated aqueous sodium bicarbonate (10 mL) was added and the layers were separated. The aqueous layer was extracted with methylene chloride (3×5 mL). The combined organics were dried over sodium sulfate and the solvent was removed in vacuo. Chromatography (10%–20%–30% EtOAc/pentane) provided residual starting material A61 (89.8 mg, 31%) and chloroacetate ester 511 (152.5 mg, 44%). 511: $R_f$ (20% EtOAc/pentane)=0.56; IR (film): 3515.2, 2954.4, 2871.9, 1738.5, 1455.8, 1371.6, 1308.7, 1132.8, 972.7 cm$^{-1}$; $^1$H-NMR (300 MHz, CDCl$_3$) δ0.75 (1H, t, J=13.2 Hz), 0.87 (3H, d, J=2.7 Hz), 0.89 (3H, d, J=3 Hz), 0.92–0.93 (10H, m), 1.19–1.26 (2H, m), 1.39–1.79 (7H, m), 2.40 (1H, quin, J=6.9 Hz), 2.74 (1H, br. d, J=13.2 Hz), 3.65–3.66 (2H, m), 3.81 (1H, dd, J=11.6, 4.7 Hz), 4.00–4.17 (4H, m), 4.07 (2H, s); $^{13}$C-NMR (75 MHz, CDCl$_3$) δ18.9, 19.3, 21.4, 22.2, 22.3, 23.8, 24.2, 29.0, 31.8, 34.5, 37.3, 37.4, 38.2, 40.9, 50.9, 58.8, 70.5, 71.6, 76.1, 101.0, 167.3; HRMS calc'd for $C_{21}H_{37}ClO_5$: 404.2330; found: 404.2329; $[\alpha]^{24.3}_d$:+4.95° (c 3.43, CH$_2$Cl$_2$).

Formula 512

To acid 28 (structure not shown) prepared as described in Theisen et al. (1998) (hydrogen (3R, 1'R)-1-(1'-napthyl) ethyl 3-[(tert-butyldimethylsilyl)oxy] pentanedioate, 309 mg, 0.744 mmol) in toluene (6 mL) was added triethylamine (263 µL, 1.98 mmol) followed by the Yamaguchi reagent (124 µL, 0.79 mmol) and stirred for 2 hr at room temperature. DMAP (303 mg, 2.50 mmol) was then added followed by 511 (190 mg, 0.469 mmol) and the mixture was stirred for 45 min. The reaction was then diluted with EtOAc (5 mL) and saturated aqueous sodium bicarbonate (10 mL) was added. The layers were separated and the aqueous layer was extracted with EtOAc (3×5 mL). The combined organics were washed with saturated aqueous ammonium chloride (10 mL), the layers were separated and the aqueous layer was extracted with EtOAc (2×5 mL). The combined organics were dried over sodium sulfate and the solvent was removed in vacuo. Chromatography (5%–10% EtOAc/pentane) provided 512 (311.9 mg, 83%): $R_f$ (10% EtOAc/pentane)=0.46; IR (film): 2953.8, 2868.2, 1738.1, 1471.9, 1373.6, 1307.9, 1258.5, 1160.3, 1108.7, 1069.3, 977.5, 837.0, 777.9 cm$^{-1}$; $^1$H-NMR (500 MHz, CDCl$_3$) δ0.04 (3H, s), 0.12 (3H, s), 0.61 (1H, t, J=13.2 Hz), 0.79 (9H, s), 0.82–0.92 (9H, m), 0.94 (3H, s), 0.95 (3H, s), 1.12–1.15 (1H, m), 1.35–1.47 (1H, m), 1.56–1.65 (4H, m), 1.69 (3H, d, J=6.5 Hz), 1.72–1.79 (1H, m), 2.37 (1H, quin, J=6.9 Hz), 2.56–2.63 (4H, m), 2.68 (1H, dd, J=15.3, 5.3 Hz), 3.64–3.68 (1H, m), 3.76 (1H, dd, J=11.8, 4.8 Hz), 3.86 (1H, d, J=11 Hz), 3.97 (1H, td, J=12.6, 1.8 Hz), 4.01 (1H, d, J=11 Hz), 4.05 (2H, s), 4.51 (1H, quin, J=6 Hz), 4.98 (1H, dd, J=9.5, 1.0 Hz), 6.64 (1H, q, J=6.5 Hz), 7.42–7.53 (3H, m), 7.57 (1H, d, J=7.0 Hz), 7.78 (1H, d, J=8.0 Hz), 7.85 (1H, d, J=8.5 Hz), 8.06 (1H, d, J=8.5 Hz) ); $^{13}$C-NMR (125 MHz, CDCl$_3$) δ−5.1, −4.8, 14.2, 17.8, 19.0, 20.3, 21.4, 21.7, 21.8, 22.3, 23.7, 24.3, 25.6, 28.8, 31.0, 34.9, 37.2, 37.3, 38.1, 40.7, 41.8, 42.1, 51.1, 58.9, 65.6, 65.7, 69.7, 70.9, 73.0, 100.5, 123.1, 123.2, 125.3, 125.6, 126.2, 128.4, 128.8, 130.1, 133.8, 137.3, 167.1, 170.1, 170.4; HRMS calc'd for C$_{44}$H$_{67}$ClO$_9$Si (+1Na): 825.4149; found: 825.4141; $[\alpha]^{25.5}_d$:−2.17° (c 8.42, CH$_2$Cl$_2$).

Formula 513

To 512 (156 mg, 0.194 mmol) in EtOAc (4.4 mL) at room temperature was added Pd(OM)$_2$/C (75 mg). The black slurry was stirred and the flask was evacuated and refilled with hydrogen (5 times). After 5.5 h under 1 atm. of hydrogen, the reaction was poured directly onto a silica column pre-packed with pentane and eluted (20% EtOAc+ 1% AcOH/pentane) to provide 119 mg of linker synthon 513 in 95% yield. 513: $R_f$ (20% EtOAc+1% AcOH/pentane)= 0.27; IR (film): 2800.0–3422.4, 2954.1, 2866.6, 1738.3, 1714.1, 1473.1, 1375.8, 1308.0, 1258.4, 1159.6, 1107.3, 977.0, 837.3, 778.8 cm$^{-1}$; $^1$H-NMR (300 MHz, CDCl$_3$) δ0.08 (3H, s), 0.09 (3H, s), 0.66 (1H, t, J=13.0 Hz), 0.85–0.92 (19H, m), 0.95 (3H, s), 0.97 (3H, s), 1.06–1.25 (1H, m), 1.33–1.50 (4H, m), 1.58–1.81 (4H, m), 2.37 (1H, dsept, J=6.6, 1.2 Hz), 2.53 (1H, dd, J=15.3, 6.9 Hz), 2.58–2.60 (3H, m), 2.66 (1H, dd, J=15.0, 4.8 Hz), 3.64–3.68 (1H, m), 3.79 (1H, dd, J=11.7, 4.2 Hz), 3.86 (1H, d, J=11.1 Hz), 3.98–4.03 (1H, m), 4.00 (1H, d, J=11.1 Hz), 4.06 (2H, s), 4.49 (1H, quin, J=5.9 Hz), 4.98 (1H, dd, J=9.6, 1.8 Hz)); $^{13}$C-NMR (75 MHz, CDCl$_3$) δ−5.1, −4.8, 17.9, 19.0, 20.3, 21.4, 21.7, 22.3, 23.7, 24.3, 25.7, 28.8, 31.1, 34.9, 37.3, 37.4, 38.2, 40.7, 41.9, 42.0, 51.1, 58.9, 65.7, 65.7, 70.9, 73.3, 100.6, 167.2, 170.2, 176.4; HRMS calc'd for C$_{32}$H$_{57}$ClO$_9$Si (+1Na): 671.3348; found: 671.3358; $[\alpha]^{27.4}_d$:−20.46° (c 7.46, CH$_2$Cl$_2$).

Example 3

Exemplary Bryostatin Analogues

3A. Formula II—C26 Des-Methyl Bryostatin Analogue (702)

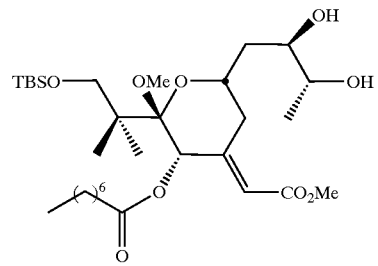

201.1 (Formula 201 where $R^{20}$ is —O—CO—C$_7$H$_{15}$ and $R^{21}$ is =CH—CO$_2$Me)

To di-benzyl ether 111.1 (Example 1C, 503 mg, 0.169 mmol) in EtOAc (12.3 mL) at room temperature is added Pd(OH)$_2$/C (82 mg). The black slurry was stirred vigorously and the flask was evacuated and refilled 4 times with hydrogen (1 atm). After 1 h, the reaction was poured directly onto a silica column and eluted (50% EtOAc/pentane to 100% EtOAc) to provide 201.1 (240.2 mg, 65%) as a colorless oil.

201.1: $R_f$ (50% EtOAc/pentane)=0.36; IR (film)=3424, 2955, 2930, 2857, 1748, 1722, 1156, 1081, 837, 776 cm$^{-1}$; $^1$H NMR (300 MHz, CDCl$_3$) δ0.00 (6H, s), 0.84–0.93 (12H, m), 0.96 (3H, s), 0.98 (3H, s), 1.20 (3H, d, J=6.0 Hz), 1.15–1.38 (10H, m), 1.62 (1H, t, J=7.1 Hz), 1.71 (1H, t, J=5.7 Hz), 2.25–2.45 (2H, m), 2.54 (1H, s), 2.89 (1H, d, J=4.2 Hz), 3.34–3.48 (1H, m), 3.36 (3H, s), 3.52 (2H, dd, J=15.9, 9.6 Hz), 3.58–3.76 (3H, m), 3.67 (3H, s), 4.14–4.26 (1H, m), 5.55 (1H, s), 5.89 (1H, s); $^{13}$C NMR (75 MHz, CDCl$_3$) δ−5.5, 14.0, 18.4, 19.4, 20.7, 22.5, 24.6, 25.9, 28.8, 29.0, 31.6, 32.4, 34.4, 39.0, 46.6, 51.1, 51.3, 67.5, 68.4, 70.9, 71.9, 72.3, 103.1, 116.9, 152.4, 166.5, 171.8; $[\alpha]^{23.9}_D$=−2.24° (c=6.53, CH$_2$Cl$_2$).

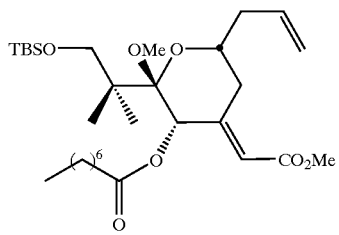

202.1 (Formula 202 where $R^{20}$ is —O—CO—C$_7$H$_{15}$ and $R^{21}$ is =CH—CO$_2$Me)

To diol 201.1 (26.8 mg, 0.045 mmol) in benzene (1.2 mL) under nitrogen at 0° C. was added triethylamine (30 µL, 0.227 mmol) followed by lead tetraacetate (50 mg, 0.113 mmol). The resulting suspension was stirred at 0° C. for 20 min. and was then quenched with an aqueous solution of saturated ammonium chloride (5 mL) and extracted with ethyl acetate (3×5 mL). The combined organic layers were dried over sodium sulfate, the solution was decanted and then the solvent was removed in vacuo to provide the crude aldehyde (structure not shown) which was taken immediately to the next step.

To the crude aldehyde (34 mg, 0.061 mmol) in TEF (1.4 mL) under nitrogen at 0° C. was added a 0.5M solution of the Tebbe reagent in toluene (122 μL, 0.061 mmol) dropwise. The reddish-black slurry was stirred at 0° C. for 15 min. and was then quenched with a saturated aqueous solution of sodium bicarbonate (5 mL). The biphasic mixture was extracted with ethyl acetate (3×5 mL). The combined organic layers were dried over sodium sulfate, the solution was decanted and then the solvent was removed in vacuo. Chromatography (5% EtOAc/pentane) provides olefin 202.1 (19 mg, 56%—2 steps) as a colorless oil.

202.1: $R_f$ (10% EtOAc/pentane)=0.62; IR (film)=2955, 2930, 2857, 1747, 1722, 1667, 1155, 1082, 837, 775 cm$^{-1}$; $^1$H NMR (300 MHz, CDCl$_3$) δ0.01 (6H, s), 0.80–0.90 (12H, m), 0.96 (3H, s), 1.00 (3H, s), 1.20–1.38 (10H, m), 1.56–1.72 (1H, m), 2.24–2.46 (4H, m), 3.43 (1H, d, J=15.9 Hz), 3.30 (3H, s), 3.54 (2H, dd, J=18.9, 9.3 Hz), 3.68 (3H, s), 3.87–3.91 (1H, m), 5.09–5.16 (2H, m), 5.53 (1H, s), 5.80–5.98 (1H, m), 5.88 (1H, s); $^{13}$C NMR (75 MHz, CDCl$_3$) δ –5.4, 14.0, 18.4, 20.5, 20.6, 22.6, 24.7, 25.9, 28.9, 29.0, 31.6, 32.1, 34.5, 40.0, 47.0, 51.1, 67.3, 71.0, 72.1, 103.0, 116.6, 117.7, 133.8, 153.1, 166.6, 171.9; $[\alpha]^{22.0}_D$=–7.91° (c=1.91, CH$_2$Cl$_2$).

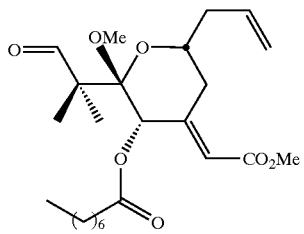

203.1 (Formula 203 where $R^{20}$ is —O—CO—C$_7$H$_{15}$ and $R^{21}$ is =CH—CO$_2$Me)

To a solution of silyl ether 202.1 (101.7 mg, 0.1833 mmol) and pyridine (267 μL, 3.30 mmol) in THF (1.53 mL) in a polypropylene vial was added 70% HF/pyridine complex (104.8 μL, 3.67 mmol) at room temperature. The solution was stirred for 18 hours and was then quenched with a saturated aqueous solution of sodium bicarbonate (5 mL). The biphasic mixture was extracted with ethyl acetate (4×5 mL). The combined organic layers were dried over sodium sulfate, the solution was decanted, and the solvent was removed in vacuo to afford the corresponding de-silylated alcohol (structure not shown) as a pale yellow oil which was used immediately in the next step.

The crude alcohol was dissolved in CH$_2$Cl$_2$ (2 mL) and treated with a single portion of 1,1,1-triacetoxy-1,1-dihydro-1,2-benziodoxol-3(1H)-one (Dess-Martin periodinane, 117 mg, 0.275 mmol) at room temperature. The mixture was stirred for 45 min and quenched with saturated aqueous NaHCO$_3$/Na$_2$S$_2$O$_3$ (2 mL). The two phase system was vigorously stirred until the organic layer has cleared (90 min). The layers were then separated and the aqueous phase was extracted with CH$_2$Cl$_2$ (4×5 mL). The combined organic layers were dried over sodium sulfate, the solution was decanted and then the solvent was removed in vacuo. Chromatography on silica gel (7.5% EtOAc/hexanes) provides aldehyde 203.1 (43.7 mg, 54%—2 steps) as a colorless oil.

203.1: $R_f$ (15% EtOAc/pentane)=0.58; IR (film)=2930, 2857, 1750, 1723, 1668, 1160, 1048 cm$^{-1}$; $^1$H NMR (300 MHz, CDCl$_3$) δ0.86 (3H, t, J=6.3 Hz, octanoate Me), 1.00 (3H, s, C18 Me), 1.16 (3H, s, C18 Me), 1.18–1.31 (10H, m), 1.46–1.60 (2H, m), 2.18 (2H, t, J=7.4 Hz), 2.43 (2H, t, J=6.6 Hz), 3.39 (3H, s), 3.66 (1H, d, J=18.9 Hz), 3.69 (3H, s), 3.74–3.84 (1H, m), 5.13–5.20 (2H, m), 5.85–6.00 (1H, m), 5.96 (1H, s), 9.71 (1H, s); $^{13}$C NMR (75 MHz, CDCl$_3$) δ14.1, 16.3, 19.1, 22.6, 24.3, 28.9, 30.4, 31.6, 38.9, 40.0, 51.2, 51.4, 54.0, 71.5, 71.9, 102.2, 118.2, 119.8, 133.4, 150.3, 166.4, 171.7, 202.4; $[\alpha]^{23.6}_D$=–6.07° (c=2.23, CH$_2$Cl$_2$).

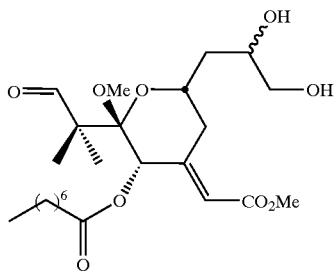

204.1 (Formula 204 where $R^{20}$ is —O—CO—C$_7$H$_{15}$ and $R^{21}$ is =CH—CO$_2$Me)

A dihydroxylating stock solution was generated by dissolving (DHQD)$_2$AQN (3.6 mg, 0.00425 mmol), K$_3$Fe(CN)$_6$ (425 mg, 1.275 mmol), K$_2$CO$_3$ (175 mg, 1.275 mmol) and K$_2$OsO$_2$(OH)$_4$ (0.65 mg, 0.00175 mmol) in t-BuOH (2.1 mL) and water (2.1 mL). The resulting solution was stirred at room temperature for 3 h. 504 μL of this stock solution was added to olefin 203.1 (7.4 mg, 0.017 mmol) pre-dissolved in t-BuOH (200 μL) and water (200 μL) under nitrogen at 0° C. The resulting solution was stirred at 0–5° C. for 2 days. Water (2 mL) was then added and the biphasic mixture was then extracted with EtOAc (4×5 mL). The combined organic layers were dried over sodium sulfate, the solution was decanted and then the solvent was removed in vacuo. Chromatography (90% EtOAc/pentane to 100% EtOAc) provides diol 204.1 (5.6 mg, 70%) as an approximately 2.2:1 (β:α) mixture of diastereomers as a colorless oil.

204.1: $R_f$ (90% EtOAc/pentane)=0.36; IR (film)=3418, 2932, 2860, 1750, 1722, 1668, 1159, 1081, 1052 cm$^{-1}$; $^1$H NMR (400 MHz, CDCl$_3$) δ0.86 (3H, t, J=6.8 Hz), 1.01 (3H, s, major), 1.02 (3H, s, minor), 1.15 (3H, s, minor), 1.17 (3H, s, major), 1.20–1.36 (10H, m), 1.47–1.61 (1H, m), 1.70–1.85 (1H, m), 2.10–2.32 (3H, m), 2.55 (1H, br. s, major), 3.09 (1H, br. s, minor), 3.42–3.80 (4H, m), 3.45 (3H, s, minor), 3.46 (3H, s, major), 3.69 (3H, s), 3.98–4.20 (2H, m), 5.20 (1H, s, major), 5.25 (1H, s, minor), 5.96 (1H, s), 9.68 (1H, s, minor) 9.68 (1H, s, major); $^{13}$C NMR (100 MHz, CDCl$_3$) δ14.0, 16.5, 16.7, 19.0, 19.1, 22.5, 24.3, 28.9, 31.3, 31.3, 31.6, 33.9, 38.8, 38.9, 51.3, 51.3, 51.5, 51.6, 53.9, 66.7, 67.2, 68.2, 68.7, 70.3, 71.0, 71.4, 71.7, 102.2, 102.6, 119.6, 119.7, 150.0, 166.3, 171.7, 183.9, 201.8, 202.2.

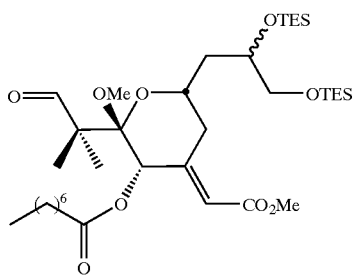

205.1 (Formula 205 where R[20] is —O—CO—C$_7$H$_{15}$ and R[21] is =CH—CO$_2$Me)

To diol 204.1 (28.5 mg, 0.0603 mmol) in methylene chloride (2.45 mL) was added pyridine (141.3 µL, 1.75 mmol) followed by TESCl (176 mL, 1.05 mmol) at room temperature. The resulting clear solution was stirred at room temperature for 15 h. Triethylamine (250 µL) was then added and the solution was directly loaded onto a silica column and eluted (5% EtOAc+5% triethylamine/pentane) to afford bis silyl ether 205.1 (42.2 mg, 100%) as an approximately 2.2:1 (β:α) mixture of diastereomers as a colorless oil.

205.1: R$_f$ (5% EtOAc+5% triethylamine/pentane)=0.58; IR (film)=2955, 2877, 1754, 1724, 1668, 1462, 1231, 1159, 1107, 1007, 743 cm$^{-1}$; $^1$H NMR (400 MHz, CDCl$_3$) δ0.44–0.65 (12H, m), 0.86 (3H, t, J=6.8 Hz), 0.88–0.98 (18H, m), 0.98 (3H, s, major), 1.00 (3H, s, minor), 1.14 (3H, s, major), 1.15 (3H, s, minor), 1.18–1.32 (10H, m), 1.58–1.71 (1H, m), 1.82–2.00 (1H, m), 2.09–2.21 (3H, m), 3.30–3.71 (3H, m), 3.41 (3H, s, minor), 3.43 (3H, s, major), 3.68 (3H, s, minor), 3.69 (3H, s, major), 3.90–4.10 (2H, m), 5.19 (1H, s, minor), 5.22 (1H, s, major), 5.94 (1H, s, minor), 6.00 (1H, s, major), 9.69 (1H, s, major) 9.70 (1H, s, minor); $^{13}$C NMR (100 MHz, CDCl$_3$) δ4.3, 4.3, 4.9, 5.2, 6.2, 6.7, 6.8, 6.9, 14.0, 16.4, 16.5, 18.9, 19.0, 22.5, 24.3, 28.9, 29.7, 31.4, 31.6, 31.8, 33.9, 41.2, 41.5, 51.1, 51.2, 51.4, 51.7, 53.9, 67.3, 67.5, 68.0, 69.3, 69.8, 70.3, 71.1, 71.3, 102.1, 102.3, 119.4, 119.5, 150.2, 150.3, 151.0, 166.2, 166.2, 171.7, 202.5, 202.6.

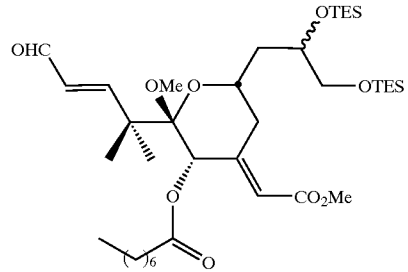

206.1 (Formula 206 where R[20] is —O—CO—C$_7$H$_{15}$ and R[21] is =CH—CO$_2$Me)

To a solution of diethylmethoxyborane (361 µL, 2.75 =mol) in Et$_2$O (2.14 mL) was added allylmagnesium bromide (1.0M in Et$_2$O, 2.50 mmol, 2.50 mL) dropwise at 0° C. The white precipitous mixture was stirred at 0° C. for 60 min. and then allowed to stand for 5 min. A 41.6 µL aliquot (0.5 M allyldiethylborane, 0.021 mmol) of this solution was added dropwise to aldehyde 205.1 (7.3 mg, 0.01 mmol) in 0.5 mL Et$_2$O at −10° C. After stirring for 30 min., the reaction was quenched with aqueous saturated NH$_4$Cl (5 mL). The biphasic mixture was then extracted with EtOAc (3×5 mL). The combined organic layers were dried over sodium sulfate, the solution was decanted and then the solvent was removed in vacuo to provide a colorless oil which was taken directly onto the next step.

The crude residue was dissolved in CH$_2$Cl$_2$ (1 mL) and treated successively with triethylamine (17.4 µL, 0.125 mmol), 4-dimethylaminopyridine (15.3 mg, 0.125 mmol) and Ac$_2$O (6 µL, 0.06 mmol) at room temperature. The solution was stirred for 17 h and then pipetted directly onto a short column of silica gel and the products eluted with 7.5% EtOAc/hexanes to afford a diastereomeric mixture of homoallylic acetates (7.9 mg, 97%—2 steps) as a colorless oil.

A portion of the isolated homoallylic acetate (5 mg, 0.0064 mmol) was dissolved in THF (253 µL) and H$_2$O (25.3 µL) and treated with N-methylmorpholine N-oxide (1.6 mg, 0.014 mmol) followed by OsO$_4$ (4 wt % in H$_2$O—16 µL, 0.0025 mmol) at room temperature. The homogeneous solution was stirred for 3 h, and then aqueous saturated sodium bicarbonate (4 mL) and water (1 mL) was added. The biphasic mixture was extracted with EtOAc (5×5 mL). The combined organic layers were dried over sodium sulfate, the solution was decanted and then the solvent was removed in vacuo to provide a colorless oil which was taken directly to the next step.

The resulting residue was immediately dissolved in benzene (0.4 mL) and treated with Et$_3$N (2.6 µL, 0.025 mmol) at room temperature. Solid Pb(OAc)$_4$ (4.2 mg, 0.0096 mmol) was quickly added in one portion and the resulting yellow precipitous mixture was stirred vigorously for 30 min. 1,8-Diazabicyclo[5.4.0]undec-7-ene (DBU, 12 µL, 0.08 mmol) was introduced and the reaction mixture was stirred for another 30 min. The mixture was added directly to a silica column and eluted (10% EtOAc/Pet. ether) to provide unsaturated aldehyde 206.1 (3.4 mg, 73%—2 steps) as an approximately 2.2:1 (β:α) mixture of diastereomers as a colorless oil.

206.1: R$_f$ (10% EtOAc/Pet. ether)=0.42; IR (film)=2955, 2877, 1748, 1723, 1692, 1461, 1229, 1154, 1105, 1008, 743 cm$^{-1}$; $^1$H NMR (400 MHz, CDCl$_3$) δ0.55–0.68 (12H, m), 0.87 (3H, t, J=6.8 Hz), 0.92–1.02 (18H, m), 1.15 (3H, s), 1.18 (3H, s), 1.20–1.34 (10H, m), 1.48–1.60 (2H, m), 1.85–2.03 (1H, m), 2.04–2.23 (2H, m), 2.27–2.39 (1H, m), 3.45–3.68 (2H, m), 3.38 (3H, s, minor), 3.40 (3H, s, major), 3.69 (3H, s, minor), 3.70 (3H, s, major), 3.95–4.05 (1H, m), 4.06–4.17 (1H, m), 5.45 (1H, s, minor), 5.47 (1H, s, major), 5.89 (1H, s), 5.93 (1H, dd, J=16.1/7.8 Hz, major), 5.93 (1H, dd, J=16.1/7.8 Hz, minor), 7.33 (1H, d, J=16.1 Hz, major), 7.36 (1H, d, J=16.1 Hz, minor), 9.53 (1H, d, J=7.8 Hz, major), 9.54 (1H, d, J=7.8 Hz, minor); $^{13}$C NMR (100 MHz, CDCl$_3$) δ4.3, 4.4, 4.9, 5.4, 6.7, 6.8, 6.9, 7.0, 14.0, 21.7, 21.8, 22.5, 23.6, 23.8, 24.5, 28.9, 28.9, 31.6, 32.5, 32.8, 34.4, 41.2, 41.6, 47.3, 51.2, 51.4, 51.5, 67.3, 67.6, 68.9, 69.2, 69.8, 70.3, 71.0, 71.1, 102.4, 102.6, 117.6, 117.7, 126.7, 151.6, 166.2, 167.2, 171.7, 194.6.

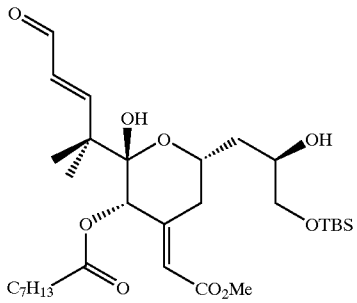

207.1b (Formula 207 where $R^{20}$ is —O—CO—$C_7H_{15}$ and $R^{21}$ is =CH—$CO_2Me$)

Enal 206.1 (22 mg, 0.03 mmol) was dissolved in acetonitrile (2 mL) and water (205 µL) at room temperature. 48% aqueous HF (388 µL, 12.1 mmol) was added dropwise and the resulting clear solution was stirred at room temperature for 75 min. and was then quenched with a saturated aqueous solution of sodium bicarbonate (15 mL) and water (3 mL). The mixture was extracted with ethyl acetate (5×10 mL). The combined organic layers were dried over sodium sulfate, the solution was decanted and then the solvent was removed in vacuo to provide a crude diol which was taken immediately to the next step.

A 0.75 mM silylating solution was generated by the addition of imidazole (62 mg, 0.91 mmol) and TBSCl (45.6 mg, 0.3 mmol) to methylene chloride (3.9 mL) at room temperature under nitrogen. To the crude diol dissolved in methylene chloride (3.9 mL) and DMF (0.4 mL) was added the above stock solution (1 mL) and stirred at room temperature for 2 h. The solution was then quenched with an aqueous solution of saturated ammonium chloride (10 mL) and extracted with methylene chloride (4×10 mL). The combined organic layers were further washed with brine (10 mL) and then dried over sodium sulfate. The solution was decanted and then the solvent was removed in vacuo. Chromatography (40% EtOAc/pentane) provides the silylated C25 β isomer 207.1b (10.4 mg, 57.4%) along with the silylated C25 α isomer 207.1a (4.6 mg, 25.4%) as colorless oils.

207.1b: $R_f$ (40% EtOAc/pentane)=0.38; IR (film)=3421, 2930, 2857, 1723, 1691, 1257, 1156, 1110, 837, 779 cm$^{-1}$; $^1$H NMR (400 MHz, CDCl$_3$) δ0.10 (6H, s), 0.87 (3H, t, J=6.8 Hz), 0.92 (9H, s), 1.14 (3H, s), 1.15 (3H, s), 1.18–1.32 (10H, m), 1.49 (1H, t, J=7.2 Hz), 1.66–1.74 (1H, m), 1.84–2.00 (1H, m), 1.98–2.15 (3H, m), 3.49 (1H, dd, J=10.0, 6.0 Hz), 3.66–3.76 (1H, m), 3.70 (3H, s), 3.82–4.00 (2H, m), 4.07 (1H, t, J=6.6 Hz), 4.20 (1H, t, J=10.8 Hz), 5.13 (1H, s), 5.96 (1H, dd, J=16.0/7.7 Hz), 6.03 (1H, s), 7.35 (1H, d, J=16.0 Hz), 9.57 (1H, d, J=7.7 Hz); $^{13}$C NMR (100 MHz, CDCl$_3$) δ-5.3, 14.0, 18.4, 20.0, 22.5, 23.1, 24.4, 25.9, 28.9, 28.9, 31.1, 31.6, 34.5, 39.0, 45.7, 51.3, 67.1, 67.2, 67.9, 72.6, 99.7, 120.7, 127.6, 150.1, 166.1, 171.7, 194.5; $[α]^{26.6}_D$=−27.24° (c=1.04, CH$_2$Cl$_2$).

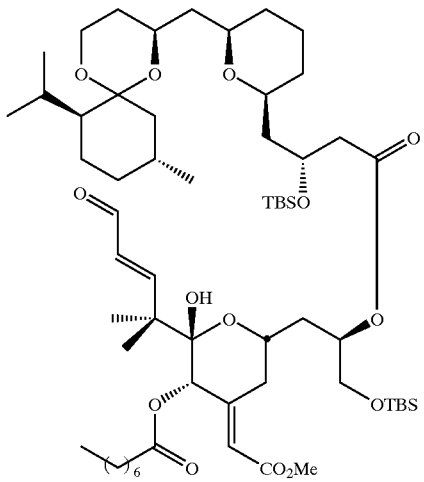

701.1 (Formula 701 where $R^{20}$ is —O—CO—$C_7H_{15}$, $R^{21}$ is =CH—$CO_2Me$ and $R^{26}$ is H)

To a solution of acid 408 Example 2B, 11.2 mg, 0.02 mmol) in toluene (0.9 mL) was added 2,4,6-trichlorobenzoyl chloride (3.2 µl, 0.02 mmol) at room temperature and the mixture was stirred for 45 min. Alcohol 207.1b (10.2 mg, 0.017 mmol) and DMAP (10.4 mg, 0.085 mmol) in toluene (1.4 mL) were added and stirred for 30 min. The mixture was directly loaded onto a silica gel column and eluted (7.5% EtOAc/pentane) to afford the ester 701.1 (15.2 mg, 79%).

701.1: $R_f$ (15% ethyl acetate/pentane)=0.29; IR (film)= 3492, 2930, 2859, 1725, 1691, 1155, 1112, 837, 777 cm$^{-1}$; $^1$H NMR (400 MHz, CDCl$_3$) δ0.04 (3H, s), 0.05 (3H, s), 0.07 (6H, s), 0.68 (1H, t, J=13.2 Hz), 0.60–0.92 (30H, m), 1.10–1.30 (18H, m), 1.34–1.84 (18H, m), 1.85–2.14 (3H, m), 2.34–2.52 (3H, m), 2.68 (1H, d, J=12.3 Hz), 3.13 (1H, s), 3.34–3.46 (2H, m), 3.60–3.70 (3H, m), 3.68 (3H, s), 3.76–3.86 (2H, m), 3.86–3.96 (1H, m), 4.06 (1H, dt, J=11.9, 2.1 Hz), 4.24–4.34 (1H, m), 5.11 (1H, s), 5.20–5.32 (1H, m), 5.96 (1H, dd, J=16.1, 7.8 Hz), 6.00 (1H, s), 7.42 (1H, d, J=16.1 Hz), 9.58 (1H, d, J=7.8 Hz); $^{13}$C NMR (100 MHz, CDCl$_3$) δ-5.3, -5.3, -4.7, -4.6, 14.0, 18.0, 18.3, 19.2, 20.1, 21.9, 22.3, 22.5, 22.9, 23.6, 23.7, 23.8, 24.3, 24.5, 25.8, 28.9, 28.9, 29.2, 30.9, 31.0, 31.6, 31.8, 31.9, 32.0, 34.5, 35.0, 37.4, 37.4, 43.5, 43.8, 44.7, 45.6, 51.2, 51.3, 59.2, 64.4, 64.9, 65.7, 66.3, 71.1, 72.7, 73.4, 73.8, 99.5, 100.4, 120.5, 127.5, 150.5, 166.4, 166.5, 171.7, 172.1, 194.6; $[α]^{24.4}_D$=−27.42° (c=0.87, CH$_2$Cl$_2$).

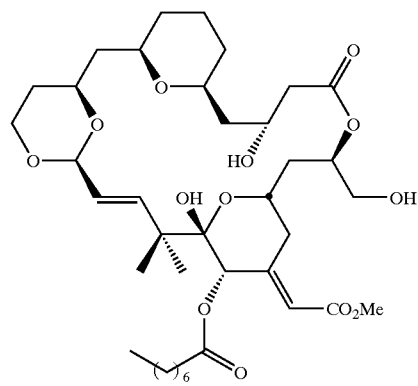

702.1 (Formula 702 where $R^3$ is OH, $R^{20}$ is —O—CO—$C_7H_{15}$, $R^{21}$ is =CH—$CO_2Me$ and $R^{26}$ is H)

To seco aldehyde 701.1 (15 mg, 0.013 mmol) in THF (3.7 mL) at room temperature in a plastic flask was added 70%

HF/pyridine dropwise. The resulting yellow solution was stirred for 2 hr and was then quenched with a saturated aqueous solution of sodium bicarbonate (12.5 mL) and water (7.5 mL). The biphasic mixture was extracted with ethyl acetate (5×15 mL). The combined organic layers were dried over sodium sulfate, the solution was decanted and then the solvent was removed in vacuo. Chromatography (70% EtOAc/pentane) provides 702.1 (7 mg, 73%) (the corresponding compound of Formula II where X is oxygen) as an amorphous solid.

702.1: $R_f$ (80% EtOAc/pentane)=0.29; IR (film)=3454, 3332, 2932, 2858, 1723, 1663, 1138, 976 cm$^{-1}$; $^1$H NMR (400 MHz, CDCl$_3$) δ0.86 (3H, t, J=6.7 Hz), 1.01 (3H, s), 1.17 (3H, s), 1.18–1.38 (12H, m), 1.40–1.66 (7H, m), 1.72–1.88 (3H, m), 1.94–2.14 (3H, m), 2.29 (1H, dt, J=7.5/1.7 Hz), 2.52 (1H, d, J=7.2 Hz), 3.45 (1H, t, J=11.2 Hz), 3.53 (1H, t, J=10.6 Hz), 3.61–3.72 (4H, m), 3.68 (3H, s), 3.88 (3H, t, J=12.4 Hz), 4.02–4.09 (2H, m), 4.10–4.19 (1H, m), 4.48 (1H, d, J=11.6 Hz), 5.02 (1H, d, J=7.6 Hz), 5.10 (1H, s), 5.13 (1H, s), 5.34–5.39 (1H, m), 5.40 (1H, dd, J=15.0/7.6 Hz), 5.97 (1H, d, J=15 Hz), 5.99 (1H, s); $^{13}$C NMR (100 MHz, CDCl$_3$) δ14.1, 19.3, 22.5, 23.0, 24.4, 24.7, 28.9, 29.0, 31.0, 31.3, 31.4, 31.6, 32.4, 34.6, 35.9, 39.9, 42.5, 42.9, 45.1, 51.1, 64.5, 65.8, 66.3, 68.6, 71.6, 74.1, 75.8, 76.0, 78.7, 98.9, 102.4, 119.9, 125.7, 142.6, 151.7, 167.0, 172.1, 172.6; $[\alpha]^{24.0}_D$=−20.02° (c=0.70, CH$_2$Cl$_2$).

3B. Formula IV—Bryostatin Analogue Containing Ether Diester Linker (807)

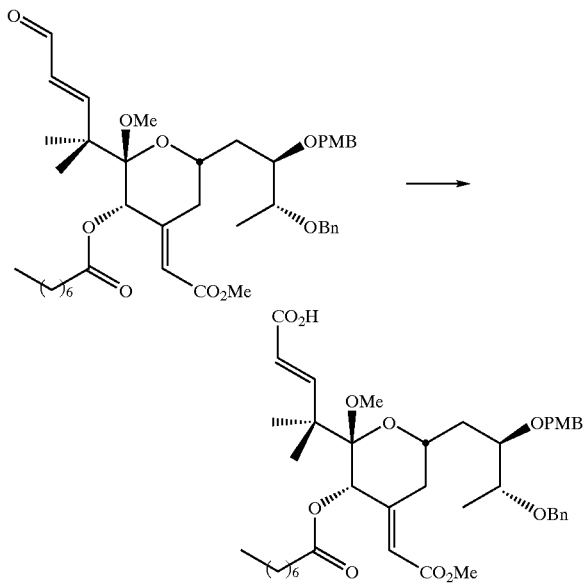

801.1 and 802.1 (Formulae 801 and 802 where $R^{20}$ is —O—CO—C$_7$H$_{15}$ and $R^{21}$ is =CH—CO$_2$Me)

Enal 801.1, prepared as described for compound 13 in Wender et al. (1998a) (22 mg, 0.030 mmol) in a tert-butanol-THF solution of 2-methyl 2-butene (1:1, 3 mL) was treated with sodium chlorite (14 mg, 0.152 mmol) and monobasic sodium phosphate (21 mg, 0.152 mmol) in water (0.5 mL). After 1 h, the mixture was diluted with ethyl acetate. The organic layer was dried over sodium sulfate. Column chromatography afforded acid 802.1: $R_f$=(25% ethyl acetate in hexane); $[\alpha]^{25}_D$=−5.97° (c 0.40, CH$_2$Cl$_2$); IR (neat)=2932, 1716, 1644, 1514, 1456, 1374 cm$^{-1}$; $^1$H NMR (500 MHz, CDCl$_3$) δ7.59 (d, J=16.0 Hz, 1 H), 7.38 (m, 5H), 7.18 (d, J=8.5 Hz, 2 H), 6.85 (d, J=8.5 Hz, 2 H), 5.88 (s, 1 H), 5.24 (d, J=16.0 Hz, 1 H), 5.51 (s, 1 H), 5.66 (d, J=11.0 Hz, 1 H), 5.60 (d, J=11.0 Hz, 2 H), 5.39 (d, J=11.0 Hz, 1 H), 4.13 (br, 1 H), 3.97 (m, 1 H), 3.85 (m, 1 H), 3.81 (s, 3 H), 3.70 (s, 3 H), 3.49 (d, J=14.5 Hz, 1 H), 3.26 (s, 3 H), 2.41 (t, J=14.5 Hz, 1H), 2.26 (m, 2H), 2.00 (m, 1 H), 1.76 (m, 1 H), 1.29~1.16 (m, 21 H), 0.88 (t, J=7.0 Hz, 3 H); $^{13}$C NMR (125 MHz, CDCl$_3$) δ172.28, 172.05, 166.29, 159.69, 159.10, 152.00, 138.62, 130.51, 129.17, 128.35, 127.61, 127.52, 117.07, 114.72, 113.75, 102.40, 76.19, 74.30, 71.68, 71.11, 70.80, 68.65, 55.23, 51.16, 48.83, 46.87, 36.08, 35.35, 34.13, 32.97, 31.62, 28.89, 24.53, 23.32, 22.50, 22.25, 14.25, 14.07,

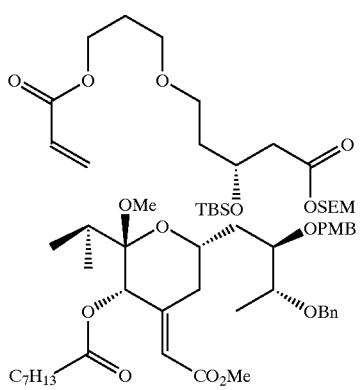

803.1 (Formula 803 where $R^{20}$ is —O—CO—C$_7$H$_{15}$ and $R^{21}$ is =CH—CO$_2$Me)

Acid 802.1 (22 mg, 0.030 mmol) in toluene (3 mL) was treated with Yamaguchi's reagent (6:L, 0.0395 mmol) and TEA (16:L, 0.122 mmol). After 30 min, alcohol 606 from Example 2F (17 mg, 0.0395 mmol) and DMAP (11 mg, 0.0912 mmol) in toluene (1 mL) was added and stirred for 1 h. The mixture was directly purified by silica gel column to give ester 803.1 (27 mg, 77% yield): $R_f$=(25% ethyl acetate in hexane); $[\alpha]^{25}_D$=−21.4° (c 0.82, CH$_2$Cl$_2$); IR (neat)=2930, 2858, 1720, 1652, 1612, 1514, 1464, 1383, 1250, 1110 cm$^{-1}$; $^1$H NMR (500 MHz, CDCl$_3$) δ7.46 (d, J=16.0 Hz, 1 H), 7.36 (m, 5 H), 7.18 (d, J=8.5 Hz, 2 H), 6.85 (d, J=8.5 Hz, 2 H), 5.87 (s, 1 H), 5.67 (d, J=16.0 Hz, 1 H), 5.50 (s, 1 H), 5.29 (q, J=6.0 Hz, 2 H), 4.63 (m, 3 H), 4.39 (d, J=11.0 Hz, 1 H), 4.29 (t, J=11.0 Hz, 1 H), 4.20 (m, 2 H), 4.12 (t, J=11.0 Hz, 1 H), 3.96 (m, 1 H), 3.86~3.66 (m, 7 H), 3.47 (m, 5 H), 3.25 (s, 3 H), 2.53 (d, J=6.5 Hz, 2 H), 2.39 (br, 1 H), 2.24 (m, 2 H), 1.99~0.85 (m, 26 H), 0.09 (s, 3 H), 0.07 (s, 3 H), 0.04 (s, 9 H); $^{13}$C NMR (125 MHz, CDCl$_3$) δ172.04, 171.07, 167.24, 166.30, 159.10, 157.02, 152.11, 138.68, 130.56, 129.18, 128.35, 128.17, 127.61, 117.04, 115.34, 113.74, 102.42, 88.96, 76.35, 74.48, 71.74, 71.13, 70.90, 68.59, 67.86, 67.34, 67.02, 66.59, 66.61, 61.52, 55.22, 51.12, 46.70, 42.93, 37.24, 36.17, 34.12, 31.64, 29.18, 28.99, 28.88, 25.75, 24.53, 23.45, 22.54, 22.38, 18.00, 17.95, 14.36, 14.06, −1.46, −4.80.

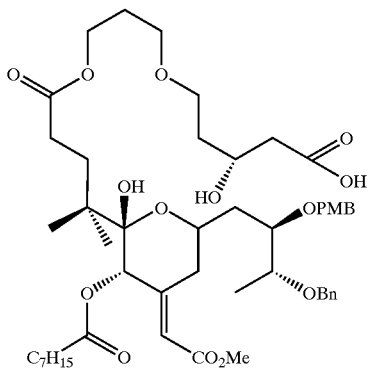

805.1 (Formula 805 Where $R^{20}$ is —O—CO—$C_7H_{15}$ and $R^{21}$ is =CH—$CO_2Me$)

Ester 803.1 (27 mg, 0.0233 mmol) in wet methylene chloride (2 mL) was treated with DDQ (11 mg, 0.0466 mmol) and stirred for 1 h. The mixture was directly purified by silica gel to give the expected alcohol silyl ether product of Formula 804. This silyl ether in acetonitrile-water (10:1, 1.5 mL) was treated with aqueous HF (100:L, 48%). After 4 h, the mixture was neutralized with aqueous sodium bicarbonate. The aqueous layer was extracted with ethyl acetate. The combined organic layer was dried over sodium sulfate. The crude hydroxy acid product 805.1 was used for the next step.

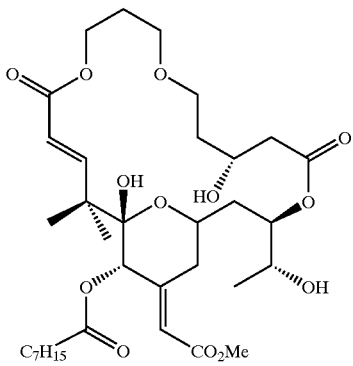

807.1 (Formula 807 where $R^{20}$ is —O—CO—$C_7H_{15}$ and $R^{21}$ is =CH—$CO_2Me$)

To a solution of DCC (13 mg, 0.0623 mmol), DMP.HCl (10 mg, 0.0623 mmol) and DMAP (11 mg, 0.089 mmol) was added hydroxy acid 805.1 (7 mg, 0.0089 mmol) in methylene chloride (3 mL) by syringe pump over 10 h. The resultant mixture was loaded directly onto a silica gel column and purified to give C26-O-benzyl ether lactone of Formula 806 where $R^{20}$ is —O—CO—$C_7H_{15}$ and $R^{21}$ is =CH—$CO_2Me$ (806.1) (3.5 mg, 50%). 806.1: $R_f$=(25% ethyl acetate in hexane); $[\alpha]^{25}_D$=4.74° (c 0.47, $CH_2Cl_2$); IR (neat)=3746, 3323, 2926, 2851, 1739, 1718, 1624, 1436, 1159 cm$^{-1}$; $^1$H NMR (500 MHz, CDCl$_3$) δ7.39 (br s, 5 H), 6.84 (d, J=16.0 Hz, 1 H), 6.03 (s, 1 H), 5.80 (d, J=16.0 Hz, 1 H), 5.41 (br d, J=12.5 Hz, 1 H), 5.20 (s, 1 H), 5.15 (s, 1 H), 4.64 (q, J=12.0 Hz, 2 H), 4.47 (q, J=5.5, 11.5 Hz, 1 H), 4.31 (m, 3 H), 3.99 (t, J=11.0 Hz, 1 H), 3.80~3.43 (m, 8 H), 2.52 (m, 2 H), 2.37~1.07 (m, 22 H), 0.89 (t, J=6.5 Hz, 3 H).

To a solution of benzyl ether 806.1 (1 mg) in methylene dichloride (0.5 mL) was added boron trichloride (excess) at −78° C., and the mixture was warmed to −20° C. over 1 h. The reaction mixture was quenched with aqueous sodium bicarbonate. The standard isolation procedure afforded bryostatin analogue 807.1. $R_f$=(25% ethyl acetate in hexane); $[\alpha]^{25}_D$=4.17° (c=0.30, $CH_2Cl_2$); IR (neat)=3480, 2927, 2856, 2361, 1718, 1281, 1161, 1105 cm$^{-1}$; $^1$H NMR (500 MHz, PhH) δ6.82 (d, J=16.5 Hz, 1 H), 6.03 (s, 1 H), 5.80 (d, J=16.5 Hz, 1 H), 5.24 (s, 1 H), 5.17 (br s, 2 H), 4.36 (m, 3 H), 4.01 (t, J=2.5 Hz, 1 H), 3.84 (q, J=6.5 Hz, 1 H), 3.68 (m, 7 H), 3.46 (t, J=9.0 Hz, 1 H), 2.57 (m, 2 H), 2.33 (m, 2 H), 2.18 (m, 1 H), 2.11~1.23 (m, 23H), 0.90 (t, J=10.0 Hz, 3 H); $^{13}$C NMR (125 MHz, PhH) δ174.37, 172.11, 171.38, 152.76, 151.21, 121.46, 120.31, 119.94, 99.21, 86.71, 73.84, 73.67, 71.96, 70.03, 68.76, 68.38, 65.14, 51.13, 45.48, 41.06, 35.99, 34.58, 32.91, 31.63, 31.14, 29.00, 28.86, 28.65, 24.68, 23.18, 22.55, 21.13, 19.64, 14.05.

3C. Formula III—Bryostatin Analogue Containing Selected C7 Substituent (705)

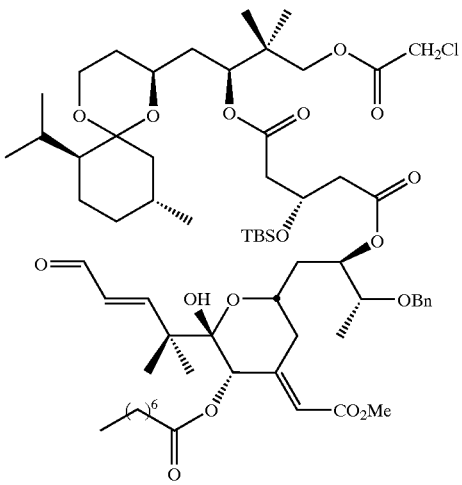

704.1 (Formula 704 where R is OH R' is OBn $R^3$ is TBSO, $R^5$ is =O, $R^7$ is t-Bu-$O_2$CMeCl, $R^8$ is H, $R^{20}$ is —O—CO—$C_7H_{15}$, $R^2$ is =CH—$CO_2Me$ and $R^{26}$ is Me)

To a methyl hemiacetal prepared as described for compound 14 in Wender et al. (1998a) (30 mg, 0.05 mmol) in acetonitrile (2.8 mL) and water (0.3 mL) was added 48% aq. HF (480 μL) and stirred at room temp. for 2 hrs. The reaction was then quenched with a saturated solution of sodim bicarbonate (5 mL) and extracted with EtOAc (5 mL×4). The combined organics were dried over sodium sulfate and the solvent was removed in vacuo to give expected hemiacetal (a compound according to Formula 303 where $R^{20}$ is —O—CO—$C_7H_{15}$ and $R^{21}$ is =CH—$CO_2Me$).

To crude acid 513 from Example 2G (47 mg, 0.075 mmol) in toluene (2.6 mL) was added triethylamine (27 μL, 0.2 mmol) and trichlorobenzoyl chloride (12.5 μL, 0.08 mmol), and the mixture was stirred for 90 min. To the resulting solution is added a solution containing the crude hemiacetal and DMAP (30.4 mg, 0.25 mmol) in toluene (4 mL). The resulting precipitous mixture was stirred for 2 h and then added directly to a silica column and eluted (15% EtOAc/pentane to 25% EtOAc/pentane) to afford seco aldehyde 704.1 (41.7 mg, 70%): $R_f$ (15% EtOAc/pentane)=0.14; IR (film): 3497.9, 2953.6, 2867.5, 1738.2, 1688.9, 1469.9, 1378.0, 1258.1, 1158.4, 1109.2, 982.5, 835.5, 779.2, 734.9 cm$^{-1}$; $^1$H-NMR (500 MHz, CDCl$_3$) δ0.05 (3H, s), 0.08 (3H, s), 0.66 (1H, t, J=13.0 Hz), 0.79–0.88 (21H, m), 0.91–0.96 (1H, m), 0.95 (3H, s), 0.97 (3H, s), 1.15 (3H, s), 1.17–1.29 (15H, m), 1.36–1.50 (6H, m), 1.59–1.78 (5H, m), 1.87–2.13 (5H, m), 2.38 (1H, dquin, J=6.8, 1.3 Hz), 2.51–2.64 (5H, m), 3.31 (1H, s), 3.60–3.68 (2H, m), 3.68 (3H, s), 3.76–3.80 (1H, m), 3.78 (1H, d, J=11.0 Hz), 3.83–3.93 (1H, m), 3.99–4.07 (1H, m), 4.00 (1H, d, J=11.0 Hz), 4.07 (2H, d, J=3.0 Hz), 4.43–4.48 (1H, m), 4.56 (1H, d, J=12.0 Hz), 4.63 (1H, d, J=12.0 Hz), 4.96 (1H, dd, J=9.5, 2.0 Hz), 5.12 (1H, s), 5.41–5.44 (1H, m), 5.95 (1H, dd, J=16.0, 8.0 Hz), 6.00 (1H, d, J=2.0 Hz), 7.27–7.35 (5H, m), 7.38 (1H, d, J=16.0 Hz), 9.49 (1H, d, J=8.0 Hz); $^{13}$C-NMR (125 MHz, CDCl$_3$) δ−5.1, −4.8, 14.0, 15.0, 17.9, 19.0, 19.8, 20.2, 21.6, 21.7, 22.4, 22.5, 22.8, 23.7, 24.3, 24.4, 25.7, 28.8, 28.8, 28.9, 30.9, 31.1, 31.6, 34.5, 34.9, 35.4, 37.2, 37.5, 38.1, 40.7, 41.6, 42.0, 45.7, 51.1, 51.2, 58.9, 65.6, 65.7, 66.1, 70.8, 71.1, 71.4, 72.5, 73.1, 74.8, 99.5, 100.5, 120.7, 127.5, 127.6, 127.8, 128.4, 138.2, 150.3, 166.2, 166.3, 167.3, 170.5, 171.7, 171.8, 194.6; HRMS calc'd for C$_{65}$H$_{103}$ClO$_{17}$ Si (+1Na): 1241.6532; found: 1241.6551; [α]$^{27.0}_d$:−31.67° (c 4.17, CH$_2$Cl$_2$).

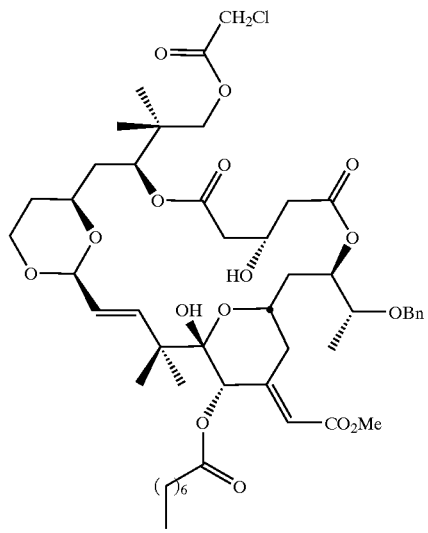

705.1 (Formula 705 where R is OH, R' is OBn, R$^3$ is OH, R$^5$ is =O, R$^8$ is t-Bu-O$_2$MeCl, R$^9$ is H, R$^{20}$ is —O—CO—C$_7$H$_{15}$, R$^{21}$ is =CH—CO$_2$Me and R$^{26}$ is Me)

To 704.1 (38 mg, 0.031 mmol) in THF (9.5 mL) was added freshly dried 4 Angstrom molecular sieve beads (57 beads) and 70% HF/pyridine (2.3 mL), and the resulting solution was stirred for 45 min. in a plastic flask. The reaction was then poured into a saturated solution of sodium bicarbonate (95 mL) and diluted with EtOAc (30 mL). The layers were separated and the aqueous layer was extracted with EtOAc (40 mL×3). The combined organic layers were dried over sodium sulfate and the solvent was removed in vacuo. Silica chromatography (40% to 100% EtOAc/pentane) afforded 705.1 (13.4 mg, 45%) and a putative diol 705.1a without the 3-hydroxy TBS protecting group (9.0 mg, 30%).

To putative diol 705.1a (4.8 mg, 4.95 mmol) in THF (0.5 mL) was added freshly dried 4A molecular sieve beads (3 beads) and 70% HF/pyridine (0.1 mL) and the resulting solution was stirred for 40 min. in a plastic flask. The reaction was then poured into a saturated solution of sodium bicarbonate (5 mL) and diluted with EtOAc (30 mL). The layers were separated and the aqueous layer was extracted with EtOAc (4 mL×4). The combined organics were dried over sodium sulfate and the solvent was removed in vacuo. Chromatography (30% to 100% EtOAc/pentane) afforded 705.1 (a compound of Formula III where R$^3$ is OH, R$^5$ is =O, R$^8$ is t-Bu-chloroacetate, R$^9$ is H, R$^{20}$ is —O—CO—C$_7$H$_{15}$, R$^{20}$ is =CH—CO$_2$Me and R$^{26}$ is Me). (1.1 mg, effectively adding 7% to above yield=52%). 705.1: R$_f$(30% EtOAc/pentane)=0.23; IR (film): 3391.9, 2929.4, 2856.8, 1731.9, 1664.5, 1434.2, 1375.1, 1249.6, 1160.5, 1133.2, 1098.3, 982.1, 735.8 cm$^{-1}$; $^1$H-NMR (500 MHz, CDCl$_3$) δ0.87 (3H, t, J=7.0 Hz), 0.93 (3H, s), 0.96 (3H, s), 1.03 (3H, s), 1.18 (3H, d, J=6.0 Hz), 1.20 (3H, s), 1.22–1.30 (10H, m), 1.51 (1H, br. d, J=12.5 Hz), 1.69–1.81 (3H, m), 2.00–2.08 (4H, m), 2.29–2.34 (3H, m), 2.41 (1H, dd, J=12.5, 4.0 Hz), 2.63 (1H, dd, J=14.3, 2.5 Hz), 2.82 (1H, dd, J=12.5, 4.5 Hz), 3.58 (1H, d, J=11.0 Hz), 3.61–3.64 (1H, m), 3.67–3.74 (2H, m), 3.68 (3H, s), 3.80 (1H, d, J=11.0 Hz), 3.82 (1H, t, J=12.0 Hz), 3.95–3.99 (1H, m), 3.97 (1H, d, J=11.0 Hz), 4.05–4.10 (1H, m), 4.08 (2H, s), 4.34 (1H, s), 4.39–4.44 (1H, m), 4.53 (1H, d, J=12.0 Hz), 4.65 (1H, d, J=12.0 Hz), 5.12 (1H, s), 5.19 (1H, dd, J=12.0, 3.0 Hz), 5.41 (1H, dd, J=16.0, 7.3 Hz), 5.50 (1H, ddd, J=12.3, 4.0, 3.0 Hz), 5.98 (1H, d, J=2.0 Hz), 6.08 (1H, d, J=16.0 Hz), 7.29–7.38 (5H, m); $^{13}$C-NMR (125 MHz, CDCl$_3$) δ14.0, 15.3, 19.4, 20.0, 21.4, 22.5, 23.9, 24.7, 28.8, 29.0, 31.2, 31.6, 32.6, 34.5, 34.6, 37.1, 38.5, 40.8, 42.2, 43.2, 45.0, 51.1, 65.0, 65.8, 66.5, 71.0, 71.1, 71.1, 73.2, 74.0, 75.0, 75.5, 98.7, 101.2, 119.7, 126.9, 127.7, 127.8, 128.4, 138.2, 142.7, 151.4, 166.8, 167.2, 170.1, 170.1, 172.1; HRMS calc'd for C$_{49}$H$_{71}$ClO$_{16}$ (+1Na): 973.4350; found: 973.4328; [α]$^{25.0}_d$:−3.04° (c 1.34, CH$_2$Cl$_2$).

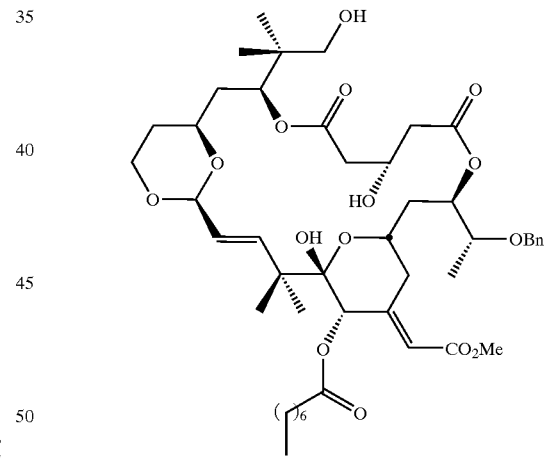

705.2 (Formula 705 where R is OH, R' is OBn, R$^3$ is OH, R$^5$ is =O, R$^8$ is t-Bu-OH, R$^9$ is H, R$^{20}$ is —O—CO—C$_7$H$_{15}$, R$^{21}$ is =CH—CO$_2$Me and R$^{26}$ is Me)

To 705.1 (7.4 mg, 7.785 μmol) in THF (0.66 mL) was added thiourea (66 mg, 0.84 mmol) and the resulting slurry was stirred at room temperature for 3 days. The reaction was then added directly to a silica column and eluted (50% to 58% to 70% EtOAc/pentane) to afford 705.2 (a compound of Formula III where R$^3$ is OH, R$^5$ is =O, R$^8$ is t-Bu-OH, R$^9$ is H, R$^{20}$ is —O—CO—C$_7$H$_{15}$, R$^{21}$ is =CH—CO$_2$Me and R$^{26}$ is Me). (6.3 mg, 92%). 705.2: R$_f$ (50% EtOAc/pentane)=0.18; IR (film): 3423.1, 2926.7, 2856.8, 1726.4, 1659.2, 1376.1, 1253.2, 1159.3, 1098.3, 980.8, 799.1, 729.7 cm⁻¹; ¹H-NMR (300 MHz, CDCl₃) δ0.77 (3H, s), 0.86 (3H, t, J=10.8 Hz), 0.96 (3H, s), 1.03 (3H, s), 1.18 (3H, d, J=8.1 Hz), 1.20 (3H, s), 1.22–1.34 (10H, m), 1.68–1.82 (3H, m), 2.01–2.12 (3H, m), 2.18–2.33 (3H, m), 2.45 (1H, dd, J=12.6, 4.5 Hz), 2.62–2.67 (2H, m), 2.85 (1H, dd, J=12.6, 3.6 Hz), 3.09–3.21 (2H, m), 3.60–3.88 (5H, m), 3.68 (3H, s), 3.93–4.00 (1H, m), 4.09 (1H, dd, J=11.1, 4.5 Hz), 4.35 (1H, s), 4.35–4.60 (1H, m), 4.52 (1H, d, J=12.0 Hz), 4.65 (1H, d, J=12.0 Hz), 5.06 (1H, d, J=9.6 Hz), 5.12 (1H, s), 5.18 (1H, d, J=7.2 Hz), 5.42 (1H, dd, J=15.9, 7.2 Hz), 5.44–5.51 (1H, m), 5.98 (1H, s), 6.08 (1H, d, J=15.9 Hz), 7.35–7.39 (5H, m); ¹³C-NMR (125 MHz, CDCl₃) δ14.1, 15.3, 18.4, 19.4, 22.4, 22.5, 23.9, 24.7, 28.9, 29.0, 29.7, 31.2, 31.6, 32.7, 34.5, 34.7, 36.8, 39.7, 42.3, 43.2, 45.0, 51.1, 65.0, 65.9, 66.5, 69.0, 71.1, 71.2, 74.0, 75.0, 77.2, 98.7, 101.3, 119.7, 126.9, 127.7, 127.9, 128.4, 138.2, 142.8, 151.5, 166.9, 170.1, 171.8, 172.1; HRMS calc'd for C₄₇H₆₉O₁₅ (+1Na): 897.4595; found: 897.4612; [α]$^{25.0}_d$:−9.50° (c 0.47, CH₂Cl₂).

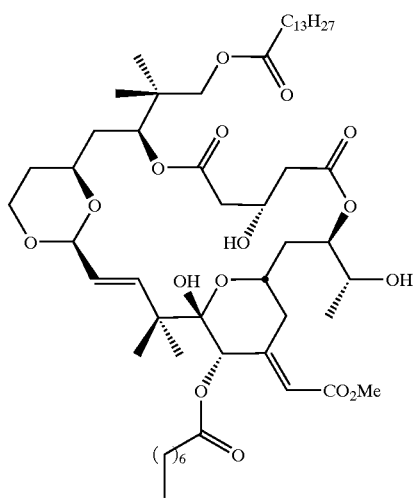

Formula 705.3

To myristic acid (10 mg, 0.044 mmol) in toluene (2.14 mL) at rt under nitrogen is added triethylamine (23.3 μL, 0.175 mmol) followed by 2,4,6-trichlorobenzoylchloride (6.8 μL, 0.044 mmol). The resulting solution was stirred for 45 min. An aliquot of this solution (63 μL, 0.0013 mmol) was added to a solution of 705.2 (1 mg, 0.00114 mmol) and DMAP (0.7 mg, 0.0059 mmol) in toluene (500 μL). The slightly yellow, cloudy solution is stirred at rt for 30 min. and then added directly to a silica column and eluted (30% EtOAC/pentane). The eluted material is then re-chromatographed (30% EtOAC/pentane). The resulting material was then dissolved in EtOAc (500 μL) and Pearlman's catalyst (2 mg) was added. The resulting suspension was evacuated and re-filled with hydrogen (5 times) while the reaction was stirred vigorously. After 30 min., the reaction is added directly to a silica column and eluted (EtOAc). This provided C7 myristate analogue 705.3 (360 μg, 32%—2 steps) (a compound of Formula III where R³ is OH, R⁵ is =O, R⁸ is t-Bu-myristate, R⁹ is H, R²⁰ is —O—CO—C₇H₁₅, R²¹ is =CH—CO₂Me and R²⁶ is Me). R$_f$ (40% EtOAc/pentane)=0.19. IR (film) 3256.8, 2915.8, 2845.2, 1746.4, 1722.9, 1158.4, 1029.0, 864.4, 793.8 cm⁻¹. ¹H-NMR (500 MHz, CDCl₃) δ0.86–0.94 (12H, m), 1.05 (3H, s), 1.14–1.38 (38H, m), 1.59–1.63 (2H, m), 1.63–1.88 (3H, m), 2.03–2.07 (3H, m), 2.31–2.42 (4H, m), 2.47 (1H, dd, J=12.8, 3.8 Hz), 2.72–2.74 (2H, m), 2.86 (1H, dd, J=12.5, 5.0 Hz), 3.70 (3H, s), 3.62–3.75 (3H, m), 3.78–3.87 (3H, m), 3.99–4.04 (1H, m), 4.09–4.14 (1H, m), 4.37–4.50 (2H, m), 5.15 (1H, s), 5.16 (1H, d, J=7.4 Hz), 5.21 (1H, d, J=12.0 Hz), 5.33–5.34 (1H, m), 5.43 (1H, dd, J=15.6, 7.4 Hz), 6.01 (1H, s), 6.07 (1H, d, J=15.6 Hz). ¹³C-NMR (500 MHz, CDCl₃) δ14.1, 19.9, 20.5, 21.1, 22.7, 23.2, 23.9, 24.7, 24.7, 24.9, 26.7, 29.1, 29.3, 29.4, 29.4, 29.7, 30.2, 31.1, 31.6, 31.9, 33.5, 33.7, 34.3, 5 34.5, 35.8, 37.2, 38.4, 42.3, 43.3, 45.0, 51.1, 65.0, 65.9, 66.6, 69.4, 70.0, 73.3, 73.5, 74.0, 75.9, 77.2, 98.7, 101.2, 119.8, 126.9, 128.8, 142.7, 151.3, 166.8, 170.4, 170.9, 172.4. HRMS (FAB) calc'd for C₅₄H₉₀O₁₆Na: 1017.6133, found: 1017.6127. [α]$^{21.1}_D$=−7.14° (c 0.035, CH₂Cl₂).

3D. Formula V—Bryostatin Analogue Containing Diester Linker (903.1)

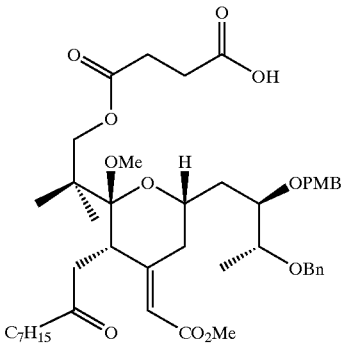

901.1 (Formula 901 where R²⁰ is —O—CO—C₇H₁₅, R²¹ is =CH—CO₂Me

To a solution of silyl ether 111 from Example 1C (1.17 g, 1.44 mmol) and pyridine (2.07 mL, 25.65 mmol) in 12 mL THF in a polypropylene vial was added HF/pyridine complex (0.83 mL, 28.83 mmol) at rt. The solution was stirred for 24 hours and diluted with EtOAc. The organic layer was washed with sat. CuSO₄ and brine, dried over Na₂SO₄ and concentrated in vacuo to afford the corresponding alcohol (not shown) as a pale yellow oil. To the alcohol (24.6 mg, 0.036 mmol) in methylene chloride (0.7 mL) was added DMAP (24.5 mg, 0.201 mmol) followed by succinic anhydride (8.6 mg, 0.086 mmol) at rt. The solution was heated to 42° C. for 3 hours and then slowly cooled to rt. Col. chromatography (40% EtOAc+1% AcOH/hexane) provided crude 901.1 (28.6 mg, 0.0353 mmol).

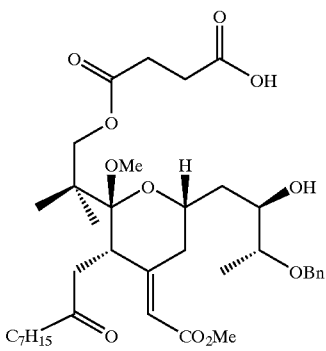

902.1 (Formula 902 where R$^{20}$ is —O—CO—C$_7$H$_{15}$, R$^{21}$ is =CH—CO$_2$Me To crude 901.1 (28.6 mg) in methylene chloride (0.8 mL) and water (9.5 µL) was added DDQ (10.4 mg, 0.046 mmol) at rt. After stirring for 2 hours, the reaction was quenched with a saturated aqueous solution of ammonium chloride and extracted with EtOAc (3×5 mL). The combined organics were then dried over sodium sulfate and the solvent was removed in vacuo. Chromatography (40% EtOAc+1% AcOH/hexane) provided seco acid 902.1 (21.9 mg, 0.032 mmol, 91% in 2 steps).

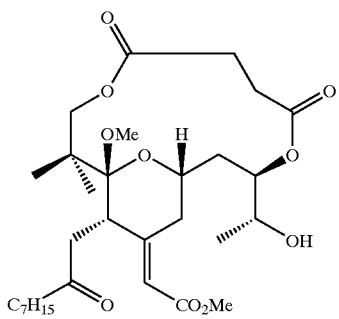

903.1

To 902.1 (5 mg, 7.38 µmol) in acetonitrile (0.4 mL) and water (42 µL) at rt was added 48% aqueous HF dropwise (24 µL, 0.738 mmol). The reaction was stirred for 40 min. and then quenched with a saturated aqueous solution of sodium bicarbonate (5 mL). The layers were separated and then the aqueous layer was extracted with EtOAc (6×5 mL). The combined organics were dried over sodium sulfate and then the solvent was removed in vacuo. The resulting clear oil (not shown) was then used immediately in the next step.

To DMAP (9 mg, 0.074 mmol) and DMAP.HCl (8.2 mg, 0.052 mmol) in methylene chloride (1.4 mL) was added DCC (10.6 mg, 0.052 mmol) at rt. The clear oil from the preceeding step in methylene chloride (2.2 mL) was then added over 3 h. The resulting mixture was stirred at rt for 4 h and then quenched with a saturated aqueous solution of sodium bicarbonate (5 mL). The layers were separated and then the aqueous layer was extracted with EtOAc (3×5 mL). The combined organics were then dried over sodium sulfate and the solvent was removed in vacuo. Silica gel chromatography (30% EtOAc/hexane) provided corresponding crude macrocycle (not shown) as a colorless oil.

The crude macrocycle from the preceeding step was dissolved in ethyl acetate (2.6 mL) and Pd(OH)$_2$/C (2.4 mg, 20% wt. on carbon) was added. The resulting suspension was evacuated and refilled with 1 Atm. hydrogen gas (×5) and was vigorously stirred under a hydrogen atmosphere for 3 hours. The crude mixture was pipetted directly onto a silica gel column and the product was eluted (50% EtOAc/hexane) to afford of bryostatin analogue 903.1 (0.3 mg, 7%—3 steps) (a compound of Formula V where p is 2, R$^{20}$ is —O—CO—C$_7$H$_{15}$, R$^{21}$ is =CH—CO$_2$Me and R$^{26}$ is Me) as a white solid.

Example 4

Bryostatin Analogues Containing Selected C20 Ester Substituent

This example illustrates methods for preparing bryostatin compounds and analogues that contain selected ester substituents at C20.

4A. Acetyl C20 Ester (702.2)

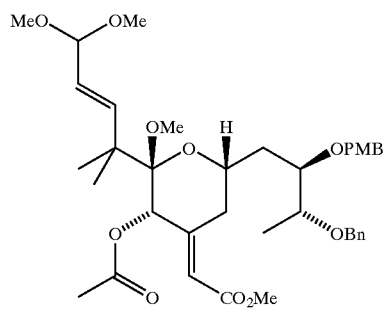

37

To a solution of enal 13, prepared as described for compound 13 in Wender et al. (1998a) (180 mg, 0.03 mmol) in 0.5 mL of MeOH at rt was added pyridinium p-toluenesulfonate (PPTS, 2 mg, catalytic) and trimethylorthoformate (5 drops). The progress of the reaction was monitored by thin layer chromatography (TLC). After 30 min the reaction was quenched with 1.0 mL Et$_3$N. The solvent was removed under reduced pressure to afford the expected crude dimethylacetal product (not shown). This product was immediately dissolved in MeOH (0.5 mL) and K$_2$CO$_3$ (3 mg, catalytic). The progress of the reaction was monitored by TLC. After 30 min the reaction was quenched. The solution was quenched with sat. NaHCO$_3$, diluted with EtOAc (10 mL), washed with H$_2$O, dried over MgSO$_4$ and concentrated under reduced pressure to afford the crude C20 free hydroxyl product (not shown). The crude product was immediately dissolved in methylene chloride (0.5 mL) and acetic anhydride (0.3 mL, excess) and DMAP (5 mg, catalytic) was added at rt. The progress of the reaction was monitored by TLC. After 30 min the reaction was quenched. The solution was quenched with sat. NaHCO$_3$, diluted with EtOAc (10 mL), washed with H$_2$O, dried over MgSO$_4$ and concentrated under reduced pressure. The crude product was purified by column chromatography on silica gel with 20% EtOAc-hexanes as eluant affording 14 mg (82% for four steps) of dimethylacetal 37. R$_f$ (20% ethyl acetate/hexanes)= 0.17; Rf (25% EtOAc/hexanes)=0.44; IR 2927, 2859, 1744, 1719, 1687, 1514, 1249, 1156, 1103, 1079, 1037 cm$^{-1}$; $^1$H NMR (300 MHz, CDCl$_3$) δ0.85 (6H, m) 1.16–1.30 (10H, m), 1.14 (3H, s), 1.18 (3H, s), 1.75 (1H, m), 1.98–2.17 (3H, m), 2.32 (1H, m), 3.27 (3H, s), 3.52 (1H, d, J=16.5 Hz), 3.68 (3H, s), 3.79 (3H, s), 3.87 (1H, m), 3.95 (1H, m), 4.09 (1H, m), 4.47 (2H, ABq, J=11.4 Hz), 5.41 (1H, s), 5.88 (1H, s), 5.91 (1H, dd, J=16.2, 7.7 Hz), 6.83 (2H, d, J=8.7 Hz), 7.16 (2H, d, J=8.7 Hz), 7.27–7.35 (6H, m), 9.44 (11H, d, J=7.7 Hz, C15); $^{13}$C NMR (75 MHz, CDCl$_3$) δ14.1, 21.7, 22.6, 24.0, 24.6, 28.9, 29.0, 31.7, 32.6, 34.5, 36.2, 47.5, 51.3, 51.5, 55.4, 69.2, 71.3, 71.8, 74.4, 76.3, 102.7, 114.1, 118.2, 127.1, 127.7, 127.9, 128.7, 129.5, 130.7, 138.9, 151.6, 159.6, 166.6, 167.3, 172.1, 195.0; [α]$_D^{20}$=−0.7° (c 1.7, CH$_2$Cl$_2$).

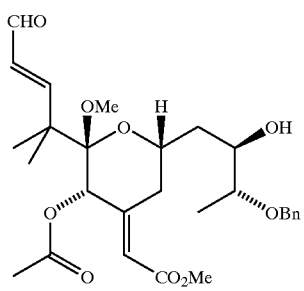

303.1 (Formula 303 where R²⁰ is —O—CO—Me, R²¹ is =CH—CO₂Me)

To a solution of dimethylacetal 37 (14 mg, 0.02 mmol) in 0.6 mL 1% aqueous CH₂Cl₂ was added solid 2,3-dichloro-5,6-dicyano-1,4-benzoquinone (DDQ, 10 mg, 0.03 mmol) at rt. The mixture was stirred for 2 h, pipetted directly onto a column of silica gel, and the product eluted with 35% EtOAc/hexanes to provide intermediate alcohol 303.1 (10 mg, 91%) as a colorless oil: $R_f$ (35% EtOAc/hexanes)=0.22; IR 3528, 2930, 2858, 1745, 1720, 1686, 1458, 1437, 1380 cm⁻¹; ¹H NMR (300 MHz, CDCl₃) δ0.86 (3H, t, J=6.9 Hz), 1.13 (3H, s), 1.17 (3H, s), 1.25 (10 H, m), 1.52 (2H, m), 1.71 (2H, m), 2.12 (2H, m), 2.35 (1H, t, J=14.1 Hz), 2.60 (1H, d, J=3.6 Hz), 3.41 (3H, s, C19 OCH₃), 3.45 (1H, m), 3.68 (3H, s), 3.82 (1H, s), 4.24 (1H, m), 4.55 (2H, ABq, J=11.4 Hz), 5.47 (1H, s), 5.86 (1H, s), 5.91 (1H, dd, J=15.9, 7.5 Hz), 7.29 (1H, d, J=15.9 Hz), 7.34 (5H, s), 9.52 (1H, d, J=7.5 Hz); ¹³C-NMR (75 MHz, CDCl₃) δ13.6, 15.3, 21.6, 22.4, 23.5, 24.7, 28.6, 28.8, 31.5, 32.8, 34.1, 39.5, 47.4, 51.1, 51.2, 68.3, 70.9, 71.0, 71.1, 78.8, 102.4, 117.4, 126.8, 127.9, 128.0, 128.5, 138.1, 151.8, 166.4, 167.3, 171.4, 194.5; $[\alpha]_D^{20}$=−21.0° (c 1.0, CH₂Cl₂).

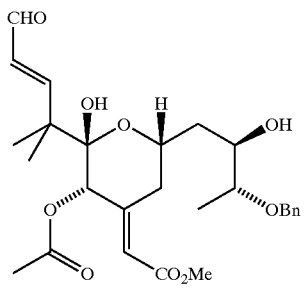

304.1 (Formula 304 where R²⁰ is —O—CO—Me, R²¹ is =CH—CO₂Me)

Alcohol 303.1 (10 mg, 0.02 mmol) was dissolved in 1.1 mL CH₃CN/H₂O (9:1) and treated with 48% aqueous HF (200 μL, 300 mol % excess) at rt. The resulting mixture was stirred for 1 h, quenched with sat. NaHCO₃ and diluted with 10 mL EtOAc. The aqueous layer was separated and extracted with EtOAc (2×). The combined organics were dried over Na₂SO₄ and concentrated in vacuo to afford crude hemiketal enal 304.1 as a colorless oil. The crude product was purified by column chromatography on silica gel with 35% EtOAc-hexanes as eluant affording 8 mg (89%) of hemiketal enal 304.1. $R_f$ (35% EtOAc/hexanes)=0.15; IR 3528, 2930, 2858, 1745, 1720, 1686, 1458, 1437, 1380 cm⁻¹; ¹H NMR (300 MHz, CDCl₃) δ0.86 (3H, t, J=6.9 Hz, octanoate Me), 1.13 (3H, s, C18 Me), 1.17 (3H, s, C18 Me), 1.25 (10 H, m), 1.52 (2H, m), 1.71 (2H, m), 2.12 (2H, m), 2.35 (1H, t, J=14.1 Hz), 2.60 (1H, d, J=3.6 Hz), 3.41 (3H, s, C19 OCH₃), 3.45 (1H, m), 3.68 (3H, s, methyl ester), 3.82 (1H, s), 4.24 (1H, m), 4.44 (1H, d, J=11.1 Hz, CH₂Ph), 4.69 (1H, d, J=11.4 Hz, CH₂Ph), 5.47 (1H, s, C20), 5.86 (1H, s, C34), 5.91 (1H, dd, J=15.9, 7.5 Hz, C16), 7.29 (1H, d, J=15.9 Hz, C17), 7.34 (5H, s, Ph), 9.52 (1H, d, J=7.5 Hz, C15); ¹³C-NMR (75 MHz, CDCl₃) δ13.8, 15.4, 21.7, 22.3, 23.6, 24.3, 28.7, 28.8, 31.4, 32.7, 34.2, 39.5, 47.3, 51.1, 51.2, 68.3, 70.8, 71.0, 71.1, 78.1, 102.3, 117.4, 126.8, 128.0, 128.1, 128.6, 138.1, 151.8, 166.4, 167.1, 171.7, 194.7; $[\alpha]_D^{20}$=−19.0° (c 1.4, CH₂Cl₂).

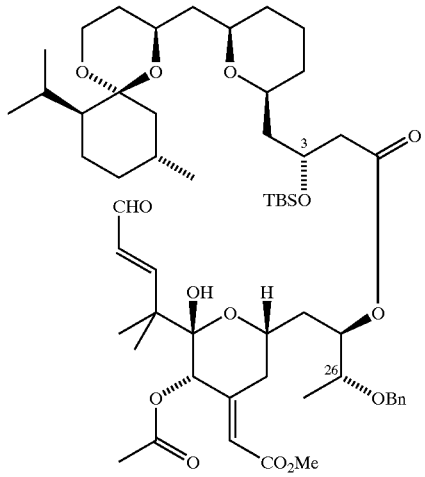

701.1 (Formula 701 where R is OH, R' is OBn, R³ is TBSO, R²⁰ is —O—CO—Me, R²¹ is =CH—CO₂Me, R²⁶ is Me and X is oxygen)

Carboxylic acid 407 (Example 2B, 15 mg, 0.03 mmol) and Et₃N (16.5 μL, 0.12 mmol) were dissolved in 300 μL toluene and treated with 2,4,6-trichlorobenzoylchloride (4.8 μL, 0.03 mmol) dropwise at rt. After 1 h at rt, a toluene solution of freshly prepared 304.1 and 4-dimethylaminopyridine (14 mg, 0.12 mmol) was added gradually and stirring was continued for 40 min. The crude mixture was pipetted directly onto a column of silica gel and the product eluted with 20% EtOAc/hexanes to provide ester 701.1 as a colorless oil (15 mg, 63%). $R_f$ (35% EtOAc/ hexanes) 0.71; IR 3487, 2927, 2856, 1723, 1689, 1455, 1379, 1228, 1156, 1113, 1084, 1032, 981 cm⁻¹; ¹H NMR (300 MHz, C₆D₆) δ0.80 (1H, t, J=12.7 Hz), 0.93 (3H, t, J=7.0 Hz), 0.97 (3H, d, J=6.6 Hz), 1.10–1.36 (24H, m), 1.36–1.85 (21H, m), 1.91–2.13 (6H, m), 2.39 (1H, t, J=12.8 Hz), 2.79 (1H, d, J=13.2 Hz), 2.93 (1H, m), 3.05 (1H, m), 3.29 (3H, s), 3.33 (1H, s), 3.37–3.48 (2H, m), 3.80 (1H, dd, J=11.4, 5.1 Hz), 3.95‑4.05 (2H, m), 4.15 (1H, td, J=10.8, 0.9 Hz), 4.23 (1H, d, J=13.5 Hz), 4.40 (1H, d, J=12.0 Hz), 4.47 (1H, d, J=12.0 Hz), 5.57 (1H, s), 5.64 (1H, dd, J=10.6, 4.6 Hz), 6.05 (1H, dd, J=16.1, 7.6 Hz), 6.39 (1H, s), 7.10–7.35 (5H, m), 7.45 (1H, d, J=16.1 Hz), 9.60 (11H, d, J=7.6 Hz); ¹³C-NMR (75 MHz, C₆D₆) δ14.1, 15.1, 19.3, 20.1, 21.3, 22.3, 22.4, 22.7, 23.8, 24.0, 24.6, 24.6, 29.0, 29.0, 29.3, 31.3, 31.6, 31.8, 34.2, 34.5, 35.2, 35.7, 36.2, 37.6, 43.5, 45.7, 51.6, 59.1, 64.9, 66.7, 71.1, 72.0, 72.9, 74.1, 75.3, 77.1, 100.2, 100.6, 121.2, 127.2, 127.3, 127.9, 128.6, 138.9, 151.2, 164.5, 166.3, 171.5, 175.1, 193.4; $[\alpha]^{20}_D$ -19° (c 1.5, $CH_2Cl_2$).

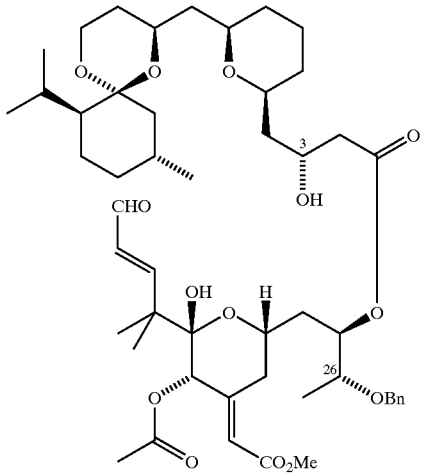

701.2 (Formula 701 where R is OH, R' is OBn, $R^3$ is OH, $R^{20}$ is —O—CO—Me $R^{21}$ is =CH—$CO_2Me$, $R^{26}$ is Me and X is oxygen)

To ester 701.1 (13 mg, 0.02 mmol) in THF (0.5 mL) was added pyridine (360 μL, 0.45 mmol) followed by 70% HF/pyridine (144 μL, 500 mol % excess) and stirred for 20 hours. The reaction was then quenched with a saturated solution of sodium bicarbonate. The biphasic mixture was extracted with ethyl acetate (×4) and the combined organics were dried over sodium sulfate. The solvent was removed in vacuo to provide crude C3 hydroxyester 701.2. The crude mixture was pipetted directly onto a column of silica gel and the product eluted with 35% EtOAc/hexanes to provide ester 701.2 as a colorless oil (9 mg, 82%). $R_f$ (40% EtOAc/hexanes)=0.19; IR 3522, 2927, 2857, 1724, 1664, 1230, 1158, 1136, 1107, 979 cm$^{-1}$; $^1$H NMR (400 MHz, $C_6D_6$) δ0.84 (3H, t, J=5.4 Hz), 0.88–0.96 (5H, m), 1.00 (3H, d, J=4.8 Hz), 1.02–1.55 (27H, m), 1.63–1.81 (2H, m), 1.82–1.94 (2H, m), 2.03 (1H, br t, J=5.2 Hz), 2.19–2.27 (1H, m), 2.34 (1H, dt, J=9, 1.5 Hz), 2.94–3.01 (2H, m), 3.22 (1H, s), 3.58 (1H, br d, J=3.6 Hz), 3.68–3.74 (1H, m), 3.84–3.88 (1H, m), 3.94 (1H, dd, J=8.6, 3.1 Hz), 4.23 (1H, dd, J=10.4, 1.7 Hz), 4.31 (1H, br t, J=8.1 Hz), 5.36–5.41 (1H, m), 5.50 (1H, s), 5.61 (1H, d, J=5.4 Hz), 6.00 (1H, dd, J=12.0, 5.4 Hz), 6.36 (1H, s), 6.53 (1H, d, J=12.0 Hz); $^{13}$C NMR (100 MHz, $C_6D_6$) δ14.2, 19.4, 19.8, 22.4, 22.9, 24.0, 24.5, 25.0, 29.1, 29.2, 30.2, 31.8, 31.9, 32.0, 33.1, 34.6, 34.9, 35.4, 36.5, 43.6, 45.6, 50.7, 66.1, 66.7, 69.6, 73.2, 74.7, 75.8, 76.3, 77.5, 98.7, 102.6, 120.5, 140.1, 151.2, 151.5, 166.5, 171.5, 174.2 $[\alpha]^{20}_D$ -13.50° (c 0.9, $CDCl_3$).

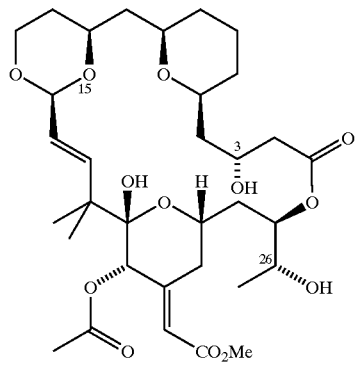

702.2 (Formula 702 where $R^3$ is OH, $R^{20}$ is —O—CO—Me $R^{21}$ is =CH—$CO_2Me$, $R^{26}$ is Me and X is Oxygen)

To a solution of C3 hydroxyester 701.2 (8 mg, 0.01 mmol) in 2.0 mL $CH_2Cl_2$ was added 4 Å molecular sieves and the mixture was aged for 20 min. 45–50 beads of Amberlyst-15 sulfonic acid resin were added and the mixture was stirred at rt for 2 h. The crude mixture was pipetted directly onto a column of silica gel and the product eluted with 35% EtOAc/hexanes to provide the expected macrocyclic product (not shown) as a colorless oil (5 mg, 83%). $R_f$ (35% EtOAc/hexanes)=0.21; IR 3522, 2927, 2857, 1724, 1664, 1230, 1158, 1136, 1107, 979 cm$^{-1}$; $^1$H NMR (400 MHz, $C_6D_6$) δ0.84 (3H, t, J=5.4 Hz), 0.88–0.96 (5H, m), 1.00 (3H, d, J=4.8 Hz), 1.02–1.55 (27H, m), 1.63–1.81 (2H, m), 1.82–1.94 (2H, m), 2.03 (1H, br t, J=5.2 Hz), 2.19–2.27 (1H, m), 2.34 (1H, dt, J=9, 1.5 Hz), 2.94–3.01 (2H, m), 3.22 (1H, s), 3.58 (1H, br d, J=3.6 Hz), 3.68–3.74 (1H, m), 3.84–3.88 (1H, m), 3.94 (1H, dd, J=8.6, 3.1 Hz), 4.23 (1H, dd, J=10.4, 1.7 Hz), 4.31 (1H, br t, J=8.1 Hz), 5.36–5.41 (1H, m), 5.50 (1H, s), 5.61 (1H, d, J=5.4 Hz), 6.00 (1H, dd, J=12.0, 5.4 Hz), 6.36 (1H, s), 6.53 (1H, d, J=12.0 Hz); $^{13}$C NMR (100 MHz, $C_6D_6$) δ14.2, 19.4, 19.8, 22.4, 22.9, 24.0, 24.5, 25.0, 29.1, 29.2, 30.2, 31.8, 31.9, 32.0, 33.1, 34.6, 34.9, 35.4, 36.5, 43.6, 45.6, 50.7, 66.1, 66.7, 69.6, 73.2, 74.7, 75.8, 76.3, 77.5, 98.7, 102.6, 120.5, 140.1, 151.2, 151.5, 166.5, 171.5, 174.2.

The macrocyclic product from the preceeding step was dissolved in 0.5 mL EtOAc and 2.2 mg $Pd(OH)_2$ (20% wt. on carbon) was added. The resulting suspension was vigorously stirred under balloon pressure of hydrogen gas for 35 min. The crude mixture was pipetted directly onto a column of silica gel and the product was eluted with 60% EtOAc/hexanes to afford acetate analogue 702.2 (4 mg, 93%) (a compound of Formula II where $R^3$ is OH, $R^{20}$ is —O—CO—Me, $R^{21}$ is =CH—$CO_2Me$, $R^{26}$ is Me and X is oxygen) as a white semi-solid. $R_f$ (50% EtOAc/hexanes)= 0.16; IR 3522, 2927, 2857, 1724, 1664, 1230 IR (neat)= 3455, 3319, 2929, 2856, 1735, 1380, 1230, 1138, 976 cm$^{-1}$; $^1$H NMR (500 MHz, $CDCl_3$) δ0.37 (3H, br. s), 0.77–0.92 (14H, m), 1.06 (3H, d, J=6.4 Hz), 1.07 (1H, t, J=11.0 Hz), 1.10–1.28 (5H, m), 1.27 (3H, s), 1.50 (3H, s), 1.57–1.78 (4H, m), 2.03 (2H, t, J=7.4 Hz), 2.17 (1H, dd, J=9.9, 0.5 Hz), 2.37 (1H, m), 2.40 (1H, m), 2.85 (1H, t, J=11.2 Hz), 2.96 (1H, t, J=10.8 Hz), 3.15 (3H, s), 3.68–3.75 (3H, m), 3.91 (1H, dd, J=11.2, 4.0 Hz), 4.12 (1H, t, J=9.7 Hz), 4.35 (1H, dd, J=13.9, 2.3 Hz), 4.48 (1H, td, J=11.0, 2.8 Hz), 4.70 (1H, d, J=12.1 Hz), 5.44 (1H, quint., J=4.8 Hz), 5.54 (1H, d, J=7.3 Hz), 5.69 (1H, s), 5.76 (1H, s), 5.85 (1H, dd, J=16.1, 7.5 Hz), 6.40 (1H, d, J=1.8 Hz), 6.50 (1H, d, J=15.9 Hz); $^{13}$C NMR (125 MHz, $CDCl_3$) δ 14.3, 19.6, 12.0, 22.9, 23.2, 24.9, 25.0, 29.2, 29.2, 31.4, 31.5, 31.9, 32.9, 34.7, 36.3, 39.9, 42.6, 43.2, 45.4, 50.5, 65.2, 66.2, 67.0, 70.4, 74.2, 74.7, 75.3, 75.9, 78.5, 99.7, 103.1, 120.5, 142.5, 152.5, 171.6, 172.5; $[\alpha]^{25}_D$=-9.0° (c=0.36, $CDCl_3$).

4B. Heptanoate C20 Ester (702.3)

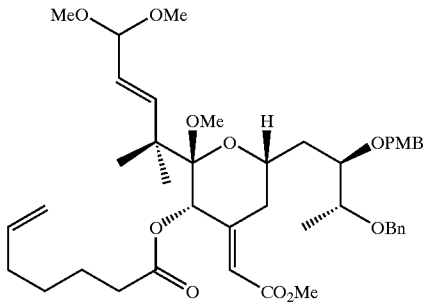

308.1 (Formula 308 where $R^{20a}$ is Heptenoate, and $R^{21}$ is =CH—CO$_2$Me)

To solution of the enal of Formula 305 (in which $R^{20}$ is $C_7H_{15}$), prepared as described for compound 13 in Wender et al. (1998a), (224 mg, 0.04 mmol) in 0.5 mL of MeOH at rt was added PPTS (2 mg, catalytic) and trimethylorthoformate (1 drop). The progress of the reaction was monitored by TLC. After 30 min the reaction was quenched with 1.0 mL Et$_3$N. The solvent was removed under reduced pressure to afford the corresponding crude dimethylacetal product of Formula 306. This product was immediately dissolved in MeOH (2.0 mL) and K$_2$CO$_3$ (3 mg, catalytic). The progress of the reaction was monitored by TLC. After 30 min the reaction was quenched. The solution was quenched with sat. NaHCO$_3$, diluted with EtOAc (10 mL), washed with H$_2$O, dried over MgSO$_4$ and concentrated under reduced pressure to afford the corresponding crude C20 free hydroxyl product of Formula 307.

Heptenoic acid (6 mg, 0.05 mmol) and Et$_3$N (21 μL, 0.16 mmol) were dissolved in 600 μL toluene and treated with 2,4,6-trichlorobenzoylchloride (7.0 μL, 0.05 mmol) dropwise at rt. After 1 h at rt, a toluene solution of the freshly prepared C20 free hydroxyl product of Formula 307 and 4-dimethylaminopyridine (DMAP, 20 mg, 0.17 mmol) was added gradually and stirring was continued for 40 min. After 30 min the reaction was quenched. The solution was quenched with sat. NaHCO$_3$, diluted with EtOAc (10 mL), washed with H$_2$O, dried over MgSO$_4$ and concentrated under reduced pressure. The crude product was purified by column chromatography on silica gel with 20% EtOAc-hexanes as eluant affording 21 mg (84%) of the corresponding dimethylacetal, C20 heptenoate product of Formula 308.1. Rf (20% ethyl acetate/hexanes)=0.22; IR 2927, 2859, 1744, 1719, 1687, 1514, 1249, cm$^{-1}$; $^1$H NMR (300 MHz, CDCl$_3$) δ0.85 (6H, m) 1.16–1.30 (10H, m), 1.14 (3H, s), 1.18 (3H, s), 1.75 (1H, m), 1.98–2.17 (3H, m), 2.32 (1H, m), 3.27 (3H, s), 3.52 (1H, d, J=16.5 Hz), 3.68 (3H, s), 3.79 (3H, s), 3.87 (1H, m), 3.95 (1H, m), 4.09 (1H, m), 4.42 (2H, ABq, J=11.0 Hz), 4.59 (1H, d, J=11.0 Hz), 4.65 (1H, d, J=11.8 Hz), 4.98 (1H, s), 5.02 (1H, d, J=15.2 Hz), 5.41 (1H, s), 5.88 (1H, s), 5.91 (1H, dd, J=16.2, 7.7 Hz), 6.83 (2H, d, J=8.7 Hz), 7.16 (2H, d, J=8.7 Hz), 7.27–7.35 (6H, m), 9.44 (1H, d, J=7.7 Hz); $^{13}$C NMR (75 MHz, CDCl$_3$) δ14.1, 21.7, 22.6, 24.0, 24.6, 28.9, 29.0, 31.7, 32.6, 34.5, 36.2, 47.5, 51.3, 51.5, 55.4, 69.2, 71.3, 71.8, 74.4, 76.3, 102.7, 114.1, 118.2, 127.1, 127.7, 127.9, 128.7, 129.5, 130.7, 138.9, 151.6, 159.6, 166.6, 167.3, 172.1, 195.0.

To a solution of 308.1 (17 mg, 0.02 mmol) in 0.5 mL 1% aqueous CH$_2$Cl$_2$ was added solid 2,3-dichloro-5,6-dicyano-1,4-benzoquinone (DDQ, 8 mg, 0.03 mmol) at rt. The mixture was stirred for 2 h, pipetted directly onto a column of silica gel, and the product eluted with 35% EtOAc/hexanes to provide the corresponding intermediate alcohol (11 mg, 85%) as a colorless oil. R$_f$ (50% EtOAc/hexanes)= 0.55; IR 3528, 2930, 2858, 1745, 1720, 1686 cm$^{-1}$; $^1$H NMR (300 MHz, CDCl$_3$) δ0.86 (3H, t, J=6.9 Hz), 1.13 (3H, s), 1.17 (3H, s), 1.25 (10 H, m), 1.52 (2H, m), 1.71 (2H, m), 2.12 (2H, m), 2.35 (1H, t, J=14.1 Hz), 2.60 (1H, d, J=3.6 Hz), 3.41 (3H, s), 3.45 (1H, m), 3.68 (3H, s), 3.82 (1H, s), 4.24 (1H, m), 4.54 (2H, ABq, J=11.2 Hz), 5.47 (1H, s), 4.98 (1H, s), 5.02 (1H, d, J=15.2 Hz), 5.86 (1H, s), 5.91 (1H, dd, J=15.9, 7.5 Hz), 7.29 (1H, d, J=15.9 Hz), 7.34 (5H, s), 9.52 (1H, d, J=7.5 Hz); $^{13}$C-NMR (75 MHz, CDCl$_3$) δ13.8, 15.4, 21.7, 22.4, 23.6, 24.4, 28.8, 28.8, 31.5, 32.8, 34.4, 39.5, 47.4, 51.1, 51.2, 68.3, 70.8, 71.1, 71.2, 78.3, 102.5, 117.3, 127.0, 127.9, 128.0, 128.5, 138.1, 151.7, 166.5, 167.4, 171.8, 194.6.

The intermediate alcohol (11 mg, 0.02 mmol) was dissolved in 1.0 mL CH$_3$CN/H$_2$O (9:1) and treated with 48% aqueous HF (200 mL, 300 mol % excess) at rt. The resulting mixture was stirred for 1 h, quenched with sat. NaHCO$_3$ and diluted with 10 mL EtOAc. The aqueous layer was separated and extracted with EtOAc (2×). The combined organics were dried over Na$_2$SO$_4$ and concentrated in vacuo to afford the corresponding crude hemiketal enal of Formula 303a as a colorless oil. The crude product was purified by column chromatography on silica gel with 50% EtOAc-hexanes as eluant affording 8 mg (80%) of the C20 heptenoate hemiketal enal. R$_f$ (35% EtOAc/hexanes)=0.05; IR 3528, 2930, 2858, 1745, 1720, 1686, 1458, 1437, 1380 cm$^{-1}$; $^1$H NMR (300 MHz, CDCl$_3$) δ0.86 (3H, t, J=6.9 Hz), 1.13 (3H, s), 1.17 (3H, s), 1.25 (10 H, m), 1.52 (2H, m), 1.71 (2H, m), 2.12 (2H, m), 2.35 (1H, t, J=14.1 Hz), 2.60 (1H, d, J=3.6 Hz), 3.41 (3H, s), 3.45 (1H, m), 3.68 (3H, s), 3.82 (1H, s), 4.24 (1H, m), 4.52 (2H, ABq, J=11.4 Hz), 4.98 (1H, s), 5.02 (1H, d, J=15.2 Hz), 5.47 (1H, s), 5.86 (1H, s), 5.91 (1H, dd, J=15.9, 7.5 Hz), 7.29 (1H, d, J=15.9 Hz), 7.34 (5H, s), 9.52 (1H, d, J=7.5 Hz); $^{13}$C-NMR (75 MHz, CDCl$_3$) δ13.9, 15.4, 21.7, 22.4, 23.6, 24.4, 28.8, 28.8, 31.4, 32.7, 34.2, 39.5, 47.4, 51.1, 51.2, 68.3, 70.9, 71.1, 71.1, 78.5, 102.4, 117.4, 126.8, 128.0, 128.0, 128.6, 138.1, 151.8, 166.4, 167.1, 171.8, 194.7.

Carboxylic acid 407 (21 mg, 0.04 mmol) and Et$_3$N (19 μL, 0.12 mmol) were dissolved in 400 μL toluene and treated with 2,4,6-trichlorobenzoylchloride (6.0 μL, 0.04 mmol) dropwise at rt. After 1 h at rt, a toluene solution of freshly prepared C20 heptenoate hemiketal enal (16 mg, 0.03 mmol) and 4-dimethylaminopyridine (17 mg, 0.13 mmol) was added gradually and stirring was continued for 40 min. The crude mixture was pipetted directly onto a column of silica gel and the product eluted with 20% EtOAc/hexanes to provide the expected ester (Formula 701 where R is OH, R' is OBn, $R^3$ is TBSO, $R^{20}$ is hepteonate, $R^{21}$ is =CH—CO$_2$Me and $R^{26}$ is methyl) as a colorless oil (24 mg, 80%). IR 3487, 2927, 2856, 1723, 1689, 1455, 1379 cm$^{-1}$; $^1$H NMR (300 MHz, CDCl$_3$) 6 0.80 (1H, t, J=12.7 Hz), 0.93 (3H, t, J=7.0 Hz), 0.97 (3H, d, J=6.6 Hz), 1.10–1.36 (24H, m), 1.36–1.85 (21H, m), 1.91–2.13 (6H, m), 2.39 (1H, t, J=12.8 Hz), 2.79 (1H, d, J=13.2 Hz), 2.93 (1H, m), 3.05 (1H, m), 3.29 (3H, s), 3.33 (1H, s), 3.37–3.48 (2H, m), 3.80 (1H, dd, J=11.4, 5.1 Hz), 3.95–4.05 (2H, m), 4.15 (1H, td, J=10.8, 0.9 Hz), 4.23 (1H, d, J=13.5 Hz), 4.50 (2H, ABq, J=12.0 Hz), 4.98 (1H, s), 5.00 (1H, d, J=15.2 Hz), 5.57 (1H, s), 5.64 (1H, dd, J=10.6, 4.6 Hz), 6.05 (1H, dd, J=16.1, 7.6 Hz), 6.39 (1H, s), 7.10–7.35 (5H, m), 7.45 (1H, d, J=16.1 Hz), 9.60 (1H, d, J=7.6 Hz); $^{13}$C-NMR (75 MHz, CDCl$_3$) δ14.1, 15.1, 19.3, 20.1, 21.3, 22.3, 22.4, 22.7, 23.8, 24.0, 24.6, 24.6, 29.0, 29.0, 29.3, 31.3, 31.6, 31.8, 34.2, 34.5, 35.2, 35.7, 36.2, 37.6, 43.5, 45.7, 51.6, 59.1, 64.9, 66.7, 71.1, 72.0, 72.9, 74.1, 75.3, 77.1, 100.2, 100.6, 121.2, 127.2, 127.3, 127.9, 128.6, 138.9, 151.2, 164.5, 166.3, 171.5, 175.1, 193.4; $[\alpha]^{20}{}_D$ −19° (c 1.5, $CH_2Cl_2$).

To the ester prepared in the preceeding step (21 mg, 0.03 mmol) in THF (0.5 mL) was added pyridine (360 μL, 0.45 mmol) followed by 70% HF/pyridine (144 μL, 500 mol % excess) and stirred for 20 hours. The reaction was then quenched with a saturated solution of sodium bicarbonate. The biphasic mixture was extracted with ethyl acetate (×4) and the combined organics were dried over sodium sulfate. The solvent was removed in vacuo to provide the corresponding crude C3 hydroxyester. The crude mixture was pipetted directly onto a column of silica gel and the product eluted with 30% EtOAc/hexanes to provide this corresponding ester (where $R^3$ is OH) as a colorless oil (13 mg, 68%). $R_f$ (30% EtOAc/hexanes)=0.23; IR 3522, 2927, 2857, 1724, 1664, 1230, 1158, 1136, 1107, 979 $cm^{-1}$; $^1H$ NMR (400 MHz, $CDCl_3$) δ0.84 (3H, t, J=5.4 Hz), 0.88–0.96 (5H, m), 1.00 (3H, d, J=4.8 Hz), 1.02–1.55 (27H, m), 1.63–1.81 (2H, m), 1.82–1.94 (2H, m), 2.03 (1H, br t, J=5.2 Hz), 2.19–2.27 (1H, m), 2.34 (1H, dt, J=9, 1.5 Hz), 2.94–3.01 (2H, m), 3.22 (1H, s), 3.58 (1H, br d, J=3.6 Hz), 3.68–3.74 (1H, m), 3.84–3.88 (1H, m), 3.94 (1H, dd, J=8.6, 3.1 Hz), 4.23 (1H, dd, J=10.4, 1.7 Hz), 4.31 (1H, br t, J=8.1 Hz), 4.97 (1H, s), 5.02 (1H, d, J=15.2 Hz), 5.36–5.41 (1H, m), 5.50 (1H, s), 5.61 (1H, d, J=5.4 Hz), 6.00 (1H, dd, J=12.0, 5.4 Hz), 6.36 (1H, s), 6.53 (1H, d, J=12.0 Hz); $^{13}C$ NMR (100 MHz, $CDCl_3$) δ14.2, 19.4, 19.8, 22.4, 22.9, 24.0, 24.5, 25.0, 29.1, 29.2, 30.2, 31.8, 31.9, 32.0, 33.1, 34.6, 34.9, 35.4, 36.5, 43.6, 45.6, 50.7, 66.1, 66.7, 69.6, 73.2, 74.7, 75.8, 76.3, 77.5, 98.7, 102.6, 120.5, 140.1, 151.2, 151.5, 166.5, 171.5, 174.2; $[\alpha]^{20}{}_D$ −13.5° (c 0.9, $CDCl_3$).

To a solution of the C3 hydroxy ester of the preceeding step (12 mg, 0.01 mmol) in 1.0 mL $CH_2Cl_2$ was added 4A molecular sieves and the mixture was allowed to stand for 20 min. 45–50 beads of Amberlyst-15 sulfonic acid resin were added and the mixture was stirred at rt for 2 h. The crude mixture was pipetted directly onto a column of silica gel and the product eluted with 35% EtOAc/hexanes to provide the corresponding heptenoate macrocycle as a colorless oil (7 mg, 70%). $R_f$ (35% EtOAc/hexanes)=0.21; IR 3522, 2927, 2857, 1724, 1664, 1230, 1158, 1136, 1107, 979 $cm^{-1}$; $^1H$ NMR (400 MHz, $CDCl_3$) δ0.84 (3H, t, J=5.4 Hz), 0.88–0.96 (5H, m), 1.00 (3H, d, J=4.8 Hz), 1.02–1.55 (27H, m), 1.63–1.81 (2H, m), 1.82–1.94 (2H, m), 2.03 (1H, br t, J=5.2 Hz), 2.19–2.27 (1H, m), 2.34 (1H, dt, J=9, 1.5 Hz), 2.94–3.01 (2H, m), 3.22 (1H, s), 3.58 (1H, br d, J=3.6 Hz), 3.68–3.74 (1H, m), 3.84–3.88 (1H, m), 3.94 (1H, dd, J=8.6, 3.1 Hz), 4.23 (1H, dd, J=10.4, 1.7 Hz), 4.31 (1H, br t, J=8.1 Hz), 4.99 (1H, s), 5.03 (1H, d, J=15.2 Hz), 5.36–5.41 (1H, m), 5.50 (1H, s), 5.61 (1H, d, J=5.4 Hz), 6.00 (1H, dd, J=12.0, 5.4 Hz), 6.36 (1H, s), 6.53 (1H, d, J=12.0 Hz); $^{13}C$ NMR (100 MHz, $CDCl_3$) δ14.2, 19.4, 19.8, 22.4, 22.9, 24.0, 24.5, 25.0, 29.1, 29.2, 30.2, 31.8, 31.9, 32.0, 33.1, 34.6, 34.9, 35.4, 36.5, 43.6, 45.6, 50.7, 66.1, 66.7, 69.6, 73.2, 74.7, 75.8, 76.3, 77.5, 98.7, 102.6, 120.5, 140.1, 151.2, 151.5, 166.5, 171.5, 174.2.

The crude macrocycle of the preceeding step (2 mg, 0.01 mmol) was dissolved in 0.5 mL EtOAc and 2.2 mg $Pd(OH)_2$ (20% wt. on carbon) was added. The resulting suspension was vigorously stirred under balloon pressure of hydrogen gas for 35 min. The crude mixture was pipetted directly onto a column of silica gel and the product was eluted with 60% EtOAc/hexanes to afford heptanoate analogue (702.3) (Formula II where $R^3$ is OH, $R^{20}$ is —O—CO—$C_6H_{13}$, $R^{21}$ is =CH—$CO_2Me$, $R^{26}$ is methyl and X is oxygen) (1 mg, 63%) as a white semi-solid. $R_f$ (50% EtOAc/hexanes)=0.21; $^1H$ NMR (300 MHz, $CDCl_3$) δ0.37 (3H, br. s), 0.79–0.92 (14H, m), 1.06 (3H, d, J=6.4 Hz), 1.07 (1H, t, J=11.0 Hz), 1.10–1.25 (5H, m), 1.27 (3H, s), 1.50 (3H, s), 1.57–1.78 (4H, m), 2.03 (2H, t, J=7.4 Hz), 2.17 (1H, dd, J=9.9/0.5 Hz), 2.37 (1H, m), 2.40 (1H, m), 2.85 (1H, t, J=11.2 Hz), 2.96 (1H, t, J=10.8 Hz), 3.15 (3H, s), 3.68–3.72 (3H, m), 3.91 (1H, dd, J=11.2, 4.0 Hz), 4.13 (1H, t, J=9.7 Hz), 4.35 (1H, dd, J=13.9, 2.2 Hz), 4.48 (1H, td, J=11.0/2.8 Hz), 4.70 (1H, d, J=12.1 Hz), 5.44 (1H, quint., J=4.8 Hz), 5.54 (1H, d, J=7.3 Hz), 5.69 (1H, s), 5.76 (1H, s), 5.85 (1H, dd, J=16.1, 7.5 Hz), 6.40 (1H, d, J=1.8 Hz), 6.50 (1H, d, J=15.9 Hz); $^{13}C$ NMR (125 MHz, $CDCl_3$) δ14.2, 19.4, 19.8, 22.4, 22.9, 24.0, 24.5, 25.0, 29.1, 29.2, 30.2, 31.8, 31.9, 32.0, 33.1, 34.6, 34.9, 35.4, 36.5, 43.6, 45.6, 50.7, 66.1, 66.7, 69.6, 73.2, 74.7, 75.8, 76.3, 77.5, 98.7, 102.6, 120.5, 140.1, 151.2, 151.5, 166.5, 171.5, 174.2.

4C. Myristate C20 Ester (702.4)

To solution of the enal of Formula 305 (in which $R^{20}$ is $C_7H_{15}$) (180 mg, 0.03 mmol), prepared as described for compound 13 in Wender et al. (1998a), in 0.5 mL of MeOH at rt was added PPTS (2 mg, catalytic) and trimethylorthoformate (5 drops). The progress of the reaction was monitored by TLC. After 30 min the reaction was quenched with 1.0 mL $Et_3N$. The solvent was removed under reduced pressure to afford the corresponding crude dimethylacetal according to Formula 306. The dimethylacetyl was immediately dissolved in MeOH (0.5 mL) and $K_2CO_3$ (3 mg, catalytic). The progress of the reaction was monitored by TLC. After 30 min the reaction was quenched. The solution was quenched with sat. $NaHCO_3$, diluted with EtOAc (10 mL), washed with $H_2O$, dried over $MgSO_4$ and concentrated under reduced pressure to afford crude C20 free hydroxyl product of Formula 307, which was reacted with myristic acid in the same manner as the reaction of heptenoic acid in Example 4B. After 30 min the reaction was quenched. The solution was quenched with sat. $NaHCO_3$, diluted with EtOAc (10 mL), washed with $H_2O$, dried over $MgSO_4$ and concentrated under reduced pressure. The crude product was purified by column chromatography on silica gel with 35% EtOAc-hexanes as eluant affording 14 mg (70% for three steps) of the desired dimethylacetal myristate of Formula 308. $R_f$ (20% ethyl acetate/hexanes)=0.5; $R_f$ (35% EtOAc/hexanes)=0.50; IR 2927, 2859, 1744, 1719, 1687, 1514, 1249, 1156, 1103, 1079, 1037 $cm^{-1}$; $^1H$ NMR (300 MHz, $CDCl_3$) δ0.85 (6H, m) 1.16–1.30 (10H, m), 1.14 (3H, s), 1.18 (3H, s), 1.75 (1H, m), 1.95–2.17 (3H, m), 2.32 (1H, m), 3.37 (3H, s), 3.52 (1H, d, J=16.5 Hz), 3.68 (3H, s), 3.79 (3H, s), 3.87 (1H, m), 3.95 (1H, m), 4.09 (1H, m), 4.55 (2H, ABq, J=11.0 Hz), 5.41 (1H, s), 5.86 (1H, s), 5.91 (1H, dd, J=16.2, 7.6 Hz), 6.83 (2H, d, J=8.7 Hz), 7.16 (2H, d, J=8.7 Hz), 7.30–7.35 (6H, m), 9.43 (1H, d, J=7.6 Hz); $^{13}C$ NMR (75 MHz, $CDCl_3$) δ14.1, 21.7, 22.6, 24.0, 24.6, 28.9, 29.0, 31.7, 32.6, 34.5, 36.2, 47.5, 51.3, 51.5, 55.4, 69.2, 71.3, 71.8, 74.4, 76.3, 102.7, 114.1, 118.2, 127.1, 127.7, 127.9, 128.7, 129.5, 130.7, 138.9, 151.6, 159.6, 166.6, 167.3, 172.1, 195.0.

To a solution of the dimethylacetal myristate (11 mg, 0.01 mmol) in 0.6 mL 1% aqueous $CH_2Cl_2$ was added solid 2,3-dichloro-5,6-dicyano-1,4-benzoquinone (DDQ, 4 mg, 0.02 mmol) at rt. The mixture was stirred for 2 h, pipetted directly onto a column of silica gel, and the product eluted with 35% EtOAc/hexanes to provide the corresponding intermediate alcohol (8 mg, 89%) as a colorless oil: $R_f$ (35% EtOAc/hexanes)=0.22; IR 3528, 2930, 2858, 1745, 1720, 1686, 1458, 1437, 1380 $cm^{-1}$; $^1H$ NMR (300 MHz, $CDCl_3$) δ0.86 (3H, t, J=6.9 Hz), 1.13 (3H, s), 1.17 (3H), 1.25 (10 H, m), 1.52 (2H, m), 1.71 (2H, m), 2.12 (2H, m), 2.35 (1H, t, J=14.1 Hz), 2.60 (1H, d, J=3.6 Hz), 3.41 (3H, s), 3.45 (1H, m), 3.68 (3H, s), 3.82 (1H, s), 4.24 (1H, m), 4.59 (2H, ABq, J=11.4 Hz), 5.47 (1H, s, C20), 5.86 (1H, s), 5.91 (1H, dd, J=15.9, 7.5 Hz), 7.29 (1H, d, J=15.9 Hz), 7.34 (5H, m), 9.52 (1H, d, J=7.5 Hz); $^{13}$C-NMR (75 MHz, CDCl$_3$) δ13.86, 15.44, 21.70, 22.38, 23.61, 24.39, 28.75, 28.81, 31.45, 32.75, 34.22, 39.50, 47.35, 51.13, 51.23, 68.32, 70.89, 71.06, 71.12, 78.51, 102.36, 117.43, 126.83, 127.97, 127.98, 128.57, 138.11, 151.80, 166.42, 167.11, 171.76, 194.73; $[α]_D^{20}$=−21.0° (c 1.0, CH$_2$Cl$_2$).

The intermediate alcohol (7 mg, 0.02 mmol) was dissolved in 1.1 mL CH$_3$CN/H$_2$O (9:1) and treated with 48% aqueous HF (200 μl, 300 mol % excess) at rt. The resulting mixture was stirred for 1 h, quenched with sat. NaHCO$_3$ and diluted with 10 mL EtOAc. The aqueous layer was separated and extracted with EtOAc (2×). The combined organics were dried over Na$_2$SO$_4$ and concentrated in vacuo to afford the crude hemi-ketal enal (44 in Reaction Scheme 11, which provides the compound number references for the remainder of the present example) as a colorless oil. The crude product was purified by column chromatography on silica gel with 35% EtOAc-hexanes as eluant affording 6 mg (86%) of enal 44. R$_f$ (35% EtOAc/hexanes)=0.15; IR 3528, 2930, 2858, 1745, 1720, 1686, 1458, 1437, 1380 cm$^{-1}$; $^1$H NMR (300 MHz, CDCl$_3$) δ0.87 (3H, t, J=6.9 Hz), 1.13 (3H, s), 1.15 (3H, s), 1.28 (10 H, m), 1.52 (2H, m), 1.71 (2H, m), 2.12 (2H, m), 2.35 (1H, t, J=14.1 Hz), 2.60 (1H, d, J=3.6 Hz), 3.41 (3H, s), 3.45 (1H, m), 3.68 (3H, s), 3.82 (1H, s), 4.24 (1H, m), 4.56 (2H, ABq, J=11.0 Hz), 5.47 (1H, s), 5.86 (1H, s), 5.91 (1H, dd, J=15.9, 7.4 Hz), 7.28 (1H, d, J=15.9 Hz), 7.35 (5H, s), 9.52 (1H, d, J=7.4 Hz); $^{13}$C-NMR (75 MHz, CDCl$_3$) δ13.9, 14.1, 19.4, 20.0, 22.7, 23.0, 24.4, 24.6, 29.1, 29.1, 29.4, 29.4, 29.6, 29.7, 31.2, 31.4, 31.9, 32.4, 34.6, 36.0, 40.0, 42.6, 42.9, 45.0, 51.1, 64.5, 66.3, 68.7, 70.4, 73.7, 74.1, 75.8, 76.1, 77.2, 78.7, 94.0, 98.9, 102.4, 119.7, 125.7, 142.8, 151.8, 167.0, 172.1, 172.5, 194.7.

Carboxylic acid 6 (6 mg, 0.01 mmol) and Et$_3$N (6 μL, 0.04 mmol) were dissolved in 300 μL toluene and treated with 2,4,6-trichlorobenzoylchloride (2.0 μL, 0.01 mmol) dropwise at rt. After 1 h at rt, a toluene solution of freshly prepared enal 44 and 4-dimethylaminopyridine (5 mg, 0.04 mmol) was added gradually and stirring was continued for 40 min. The crude mixture was pipetted directly onto a column of silica gel and the product eluted with 20% EtOAc/hexanes to provide ester-enal 46 as a colorless oil (9 mg, 90%). R$_f$ (35% EtOAc/hexanes)=0.71; IR 3487, 2927, 2856, 1723, 1689, 1455, 1379, 1228, 1156, 1113, 1084, 1032, 981 cm$^{-1}$; $^1$H NMR (300 MHz, CDCl$_3$) δ0.80 (1H, t, J=12.7 Hz), 0.93 (3H, t, J=7.0 Hz), 0.98 (3H, d, J=6.6 Hz), 1.10–1.41 (24H, m), 1.42–1.85 (21H, m), 1.92–2.13 (6H, m), 2.39 (1H, t, J=12.7 Hz), 2.81 (1H, d, J=13.2 Hz), 2.93 (1H, m), 3.05 (1H, m), 3.29 (3H, s), 3.33 (1H, s), 3.37–3.48 (2H, m), 3.80 (1H, dd, J=11.4, 5.1 Hz), 3.95–4.05 (2H, m), 4.15 (1H, td, J=10.8, 0.9 Hz), 4.23 (1H, d, J=13.5 Hz), 4.46 (2H, ABq, J=11.0 Hz), 5.57 (1H, s), 5.64 (1H, dd, J=10.6, 4.6 Hz), 6.05 (1H, dd, J=15.9, 7.5 Hz), 6.39 (1H, s), 7.10–7.35 (5H, m), 7.45 (1H, d, J=15.9 Hz), 9.60 (1H, d, J=7.5 Hz); $^{13}$C-NMR (75 MHz, CDCl$_3$) δ9.6, −9.4, 9.2, 10.3, 13.2, 14.1, 15.1, 19.3, 20.1, 21.3, 22.3, 22.4, 22.7, 23.8, 24.0, 24.6, 24.6, 29.0, 29.0, 29.3, 31.3, 31.6, 31.8, 34.2, 34.5, 35.2, 35.7, 36.2, 37.6, 43.5, 45.7, 51.6, 59.1, 64.9, 66.7, 71.1, 72.0, 72.9, 74.1, 75.3, 77.1, 100.2, 100.6, 121.2, 127.2, 127.3, 127.9, 128.6, 138.9, 151.2, 164.5, 166.3, 171.5, 175.1, 193.2; $[α]^{20}_D$-19° (c 1.5, CH$_2$Cl$_2$).

To ester-enal 46 (8.0 mg, 0.001 mmol) in THF (0.5 mL) was added 70% HF/pyridine (0.3 mL, 0.3 mmol) and stirred for 2 hours. The reaction was then quenched with a saturated solution of sodium bicarbonate. The biphasic mixture was extracted with ethyl acetate (×4) and the combined organics were dried over sodium sulfate. The solvent was removed in vacuo to provide crude macrocycle. The crude mixture was chromatographed on silica gel and the product was eluted with 50% EtOAc/hexanes to afford 5.0 mg (83%) of the corresponding macrocycle as an clear oil. R$_f$ (40% EtOAc/hexanes)=0.19; IR 3522, 2927, 2857, 1724, 1664, 1230, 1158, 1136, 1107, 979 cm$^{-1}$; $^1$H NMR (300 MHz, CDCl$_3$) δ0.84 (3H, t, J=5.4 Hz), 0.88–0.96 (5H, m), 1.00 (3H, d, J=4.8 Hz), 1.02–1.55 (27H, m), 1.63–1.81 (2H, m), 1.82–1.94 (2H, m), 2.03 (1H, br t, J=5.2 Hz), 2.19–2.27 (1H, m), 2.34 (1H, dt, J=9, 1.5 Hz), 2.94–3.01 (2H, m), 3.22 (1H, s), 3.58 (1H, br d, J=3.6 Hz), 3.68–3.74 (1H, m), 3.84–3.88 (1H, m), 3.94 (1H, dd, J=8.6, 3.1 Hz), 4.23 (1H, dd, J=10.4, 1.7 Hz), 4.31 (1H, br t, J=8.1 Hz), 4.56 (2H, ABq, J=11.0 Hz), 5.36–5.41 (1H, m), 5.50 (1H, s), 5.61 (1H, d, J=5.4 Hz), 6.00 (1H, dd, J=12.0, 5.4 Hz), 6.36 (1H, s), 6.53 (1H, d, J=12.0 Hz); $^{13}$C NMR (100 MHz, CDCl$_3$) δδ14.1, 19.4, 20.0, 22.7, 23.0, 24.4, 24.6, 29.1, 29.1, 29.4, 29.4, 29.6, 29.7, 31.2, 31.4, 31.9, 32.4, 34.6, 36.0, 40.0, 42.6, 42.9, 45.0, 51.1, 64.5, 66.3, 68.7, 70.4, 73.7, 74.1, 75.8, 76.1, 77.2, 78.7, 94.0, 98.9, 102.4, 119.7, 125.7, 142.8, 151.8, 167.0, 172.1, 172.5.

To 5.0 mg (0.0005 mmol) of crude macrocycle of the preceeding step in ethyl acetate (1.0 mL) was added a catalytic amount of Pearlman's catalyst. The flask was evacuated and refilled with a 1 atm. hydrogen atmosphere (×4), stirred under hydrogen for 30 min, and then pipetted directly onto a silica gel column and eluted with 60% ethyl acetate/hexanes. This process afforded 4.8 mg (99%) of analogue 48 (702.4) (Formula II where R$^3$ is OH, R$^{20}$ is —O—CO—C$_{13}$H$_{27}$, R$^{20}$ is =CH—CO$_2$Me, R$^{26}$ is methyl and X is oxygen) as an amorphous solid. R$_f$ (50% EtOAc/hexanes)=0.16; IR 3522, 2927, 2857, 1724, 1664, 1230 IR (neat)=3455, 3319, 2929, 2856, 1735, 1380, 1230, 1138, 976 cm$^{-1}$; $^1$H NMR (300 MHz, CDCl$_3$) δ0.37 (3H, bs), 0.79–0.92 (14H, m), 1.06 (3H, d, J=6.4 Hz), 1.07 (1H, t, J=11.0 Hz), 1.10–1.25 (5H, m), 1.27 (3H, s), 1.50 (3H, s), 1.57–1.78 (4H, m), 2.03 (2H, t, J=7.4 Hz), 2.17 (1H, dd, J=9.9/0.5 Hz), 2.37 (1H, m), 2.40 (1H, m), 2.85 (1H, t, J=11.2 Hz), 2.96 (1H, t, J=10.8 Hz), 3.15 (3H, s), 3.68–3.72 (3H, m), 3.91 (1H, dd, J=11.2, 4.0 Hz), 4.13 (1H, t, J=9.7 Hz), 4.35 (1H, dd, J=13.9/2.2 Hz), 4.48 (1H, td, J=11.0, 2.8 Hz), 4.70 (1H, d, J=12.1 Hz), 5.44 (1H, quint., J=4.8 Hz), 5.54 (1H, d, J=7.3 Hz), 5.69 (1H, s), 5.76 (1H, s), 5.85 (1H, dd, J=16.1, 7.5 Hz), 6.40 (1H, d, J=1.8 Hz), 6.50 (1H, d, J=15.9 Hz); $^{13}$C NMR (125 MHz, CDCl$_3$) δ14.1, 19.4, 20.0, 22.7, 23.0, 24.4, 24.6, 29.1, 29.1, 29.4, 29.4, 29.6, 29.7, 31.2, 31.4, 31.9, 32.4, 34.6, 36.0, 40.0, 42.6, 42.9, 45.0, 51.1, 64.5, 66.3, 68.7, 70.4, 73.7, 74.1, 75.8, 76.1, 77.2, 78.7, 94.0, 98.9, 102.4, 119.7, 125.7, 142.8, 151.8, 167.0, 172.1, 172.5.

4D. Benzoate C20 Ester (702.5)

Enal 45 was prepared following the procedure for compound 111 in Example 1C except that benzoic acid was substituted for octanoic acid, to form the corresponding protected benzoate product.

Carboxylic acid 6 (6 mg, 0.01 mmol) and Et$_3$N (6 μL, 0.04 mmol) were dissolved in 300 μL toluene and treated with 2,4,6-trichlorobenzoylchloride (2 μL, 0.01 mmol) dropwise at rt. After 1 h at rt, a toluene solution of freshly prepared 45 and 4-dimethylaminopyridine (5 mg, 0.01 mmol) was added gradually and stirring was continued for 40 min. The crude mixture was pipetted directly onto a column of silica gel and the product eluted with 20% EtOAc/hexanes to provide the expected ester product as a colorless oil (8 mg, 89%). R$_f$ (35% EtOAc/hexanes)=0.71; IR 3460, 2927, 2856, 1723 cm$^{-1}$; $^1$H NMR (300 MHz, CDCl$_3$) δ0.08 3H, s), 0.08 (3H, s), 0.81 (12H, m), 0.82–0.96 (3H, m), 1.06–1.32 (15H, m), 1.59–1.81 (4H, m), 2.20 (1H, t, J=9.3 Hz), 3.33–3.44 (2H, m), 3.67–3.84 (1H, m), 4.00–4.15 (4H, m), 4.31–4.39 (1H, m), 4.55 (2H, ABq, J=8.5 Hz), 5.41 (1H, s), 5.75 (1H, dd, J=15.5, 3.4 Hz), 6.01 (1H, s), 6.39 (1H, s), 7.28–7.47 (9H, m), 7.84 (1H, d, J=6.9 Hz), 9.17 (1H, d, J=7.3 Hz); $^{13}$C-NMR (75 MHz, CDCl$_3$) δ–9.6, –9.4, 9.2, 10.3, 13.2, 14.2, 18.5, 22.0, 23.5, 28.4, 28.7, 30.7, 31.5, 33.5, 39.1, 41.5, 41.9, 44.0, 50.1, 63.7, 65.3, 67.8, 69.6, 70.3, 73.8, 74.8, 75.1, 76.2, 77.7, 98.1, 101.3, 118.8, 124.7, 126.7, 127.4, 127.5, 128.9, 132.2, 137.3, 141.8, 150.8, 163.6, 165.9, 170.2.

To the ester of the preceeding step (13 mg, 0.02 mmol) in THF (0.5 mL) was added pyridine (360 μL, 0.45 mmol) followed by 70% HF/pyridine (144 μL, 500 mol % excess) with stirring for 20 hours. The reaction was then quenched with a saturated solution of sodium bicarbonate. The biphasic mixture was extracted with ethyl acetate (×4) and the combined organics were dried over sodium sulfate. The solvent was removed in vacuo to provide the corresponding crude C3 hydroxyester. The crude mixture was pipetted directly onto a column of silica gel and the product eluted with 35% EtOAc/hexanes to provide the purified C3 hydroxyester as a colorless oil (9 mg, 82%). R$_f$ (40% EtOAc/hexanes)=0.19; IR 3522, 2927, 2857, 1724 cm$^{-1}$; $^1$H NMR (300 MHz, CDCl$_3$) 0.81–0.91 (3H, m), 1.08 (3H, s), 1.20–1.59 (9H, m), 1.31 (6H, s), 1.92–2.18 (4H, m), 2.45 (2H, bs), 3.40–3.58 (2H, m), 3.67 (3H, s), 3.69–3.78 (2H, m), 3.88–3.98 (2H, m) 4.03–4.24 (3H, m), 4.45 (1H, d, J=9.2 Hz), 4.65 (2H, ABq, J=8.5 Hz), 5.17 (1H, d, J=9.7 Hz), 5.22 (1H, s), 5.40 (1H, s), 5.44 (1H, dd, J=15.5, 7.3 Hz), 6.06 (1H, s), 6.08 (1H, d, J=15.5 Hz), 7.27–7.59 (9H, m), 8.05 (1H, d, J=6.9 Hz); $^{13}$C NMR (100 MHz, CDCl$_3$) δ14.2, 18.5, 22.0, 23.5, 28.4, 28.7, 30.7, 31.5, 33.5, 39.1, 41.5, 41.9, 44.0, 50.1, 63.7, 65.3, 67.8, 69.6, 70.3, 73.8, 74.8, 75.1, 76.2, 77.7, 98.1, 101.3, 118.8, 124.7, 126.7, 127.4, 127.5, 128.9, 132.2, 137.3, 141.8, 150.8, 163.6, 165.9, 170.2; [α]$^{20}_D$–11.5 (c 0.9, CDCl$_3$).

To 4.0 mg (0.001 mmol) of the crude C3 hydroxyester of the preceeding step in ethyl acetate (1.0 mL) was added a catalytic amount of Pearlman's catalyst. The flask was evacuated and refilled with a 1 atm. hydrogen atmosphere (×4). Stirred under hydrogen for 30 min. and then pipetted directly onto a silica gel column and eluted with 60% ethyl acetate/hexanes. HPLC (hexane: methylene chloride: i-propanol, 16:3:1) Isolated 2.2 mg (63%) of analogue 49 (702.5) (Formula II where R$^3$ is OH, R$^{20}$ is —O—CO—Ph, R$^{21}$ is =CH—CO$_2$Me, R$^{26}$ is methyl and X is oxygen) as an amorphous solid. R$_f$ (50% EtOAc/hexanes)=0.16; IR 3522, 2927, 2857, 1724, 1664, 1230 IR (neat)=3455, 3319, 2929, 2856, 1735, 1380, 1230, 1138, 976 cm$^{-1}$; $^1$H NMR (300 MHz, CDCl$_3$) δ0.81–0.92 (3H, m), 1.08 (3H, s), 1.20–1.59 (9H, m), 1.32 (6H, s), 1.90–2.18 (4H, m), 2.52–2.56 (2H, m), 3.40–3.55 (2H, m), 3.67 (3H, s), 3.73–3.79 (2H, m), 3.82–3.95 (2H, m) 4.024.22 (2H, m), 4.51 (1H, d, J=9.1 Hz), 5.11 (1H, d, J=8.9 Hz), 5.26 (1H, s), 5.40 (1H, s), 5.42 (1H, dd, J=15.5, 3.4 Hz), 6.04 (1H, d, J=15.5 Hz), 6.07 (1H, s), 7.34–7.57 (4H, m), 8.04 (1H, d, J=7.3 Hz); $^{13}$C NMR (125 MHz, CDCl$_3$) δ13.1, 18.4, 18.9, 21.7, 23.5, 28.7, 30.6, 31.4, 35.0, 39.1, 41.6, 50.1, 63.6, 67.7, 69.2, 72.6, 76.1, 77.7, 93.0, 99.2, 113.0, 124.7, 127.2, 127.5, 128.9, 132.2, 146.3, 148.1, 149.9, 150.6, 171.4, 173.2; [α]$^{25}_D$=–7.0° (c=0.36, CDCl$_3$).

Example 5

Protein Kinase C (Isozyme Mix) Assay Protocol

The following procedure was used, based on a modification of a previous procedure described by Tanaka et al. (1986). Filters (Whatman GF-B, 21 mm diam.) are soaked for 1 h in a solution containing deionized water (97 mL), and 10% polyethyleneamine (3 mL). A filtering buffer solution containing TRIS (1M, pH 7.4, 10 mL) and water (490 mL) is prepared and cooled on ice. An assay buffer solution is prepared by the addition of TRIS (1M, pH 7.4, 1 mL), KCl (1M, 2 mL), CaCl$_2$ (0.1M, 30 μL), bovine serum albumin (40 mg), diluted to 20 mL with deionized water and stored on ice. Phosphatidyl serine vesicles are prepared by the addition of phosphatidyl serine (10 mg/mL in chloroform, 0.4 mL) to a glass test tube followed by removal of the chloroform under a stream of nitrogen (5 min). To this viscous liquid is added a portion of the prepared assay buffer (4 mL) and the resulting mixture is then transferred to a plastic tube with washing. This tube is then sonicated (Branson Sonifier 250, power=6, 40% duty cycle) four times for 30 sec. with a 30 sec. rest period between sonications. The resulting solution is stored over ice. PKC is prepared by addition of cooled assay buffer (10 mL) to PKC (25 μL) purified from rat brain by the method of Mochly-Rosen and Koshland (1986) and then stored on ice. Stock solutions of compounds are diluted with absolute ethanol in glass in serial fashion. Each plastic assay incubation tube is made to contain prepared phosphatidyl serine vesicles (60 μL), prepared PKC solution (200 μL) and analogue (0–20 μL) plus EtOH (20–0 μL) for a total volume of 20 μL). Lastly, tritiated phorbol 12,13-dibutyrate (PDBU) (30 nM, 20 μL) is added to each tube. The assay is carried out using 7–10 analogue concentrations, each in triplicate. Non-specific binding is measured in 1–3 tubes by the substitution of phorbol myristate acetate (PMA) (1 mM, 5 μL) and EtOH (15 μL) for the analogue/EtOH combination. The tubes are incubated at 37° C. for 90 min. and then put on ice for 5 min. Each tube is then filtered separately through a pre-soaked filter disc. Each tube is rinsed with cold 20 mM TRIS buffer (500 μL) and the rinseate is added to the filter. The filter is subsequently rinsed with cold 20 mM TRIS buffer (5 mL) dropwise. The filters are then put in separate scintillation vials and Universol© scintillation fluid is added (3 mL). The filters are immediately counted in a scintillation counter (Beckman LS 6000SC). Counts per minute are averaged among three trials at each concentration. The data is then plotted using a least squares fit algorithm with the Macintosh version of Kaleidagraph© (Abelbeck Software) and an IC$_{50}$ (defined as the concentration of analogue required to displace half of the specific PDBU binding to PKC) is calculated. The IC$_{50}$ then allows determination of the K$_i$ for the analogue from the equation: K$_i$=IC$_{50}$/(1+[PDBu]/K$_d$ of PDBu). The K$_d$ of [H$^3$]-PDBu was determined under identical conditions to be 1.55 nM.

Example 6

PKCδ-C1B Assay Protocol

All aspects of the PKCδ-C1B assay are identical to the PKC isozyme mix assay from Example 5 except the following features: In the PKCδ-C1B assay system, assay buffer is made without CaCl$_2$. PKCδ-C1B (200 μg, 34.14 nmol), prepared by the method of Wender et al. (1995) and Irie et al. (1998) is dissolved in deionized water (160 μL) and ZnCl$_2$ (5 mM, 40 μL) is added. The resulting solution is allowed to stand at 4° C. for 10 min. An aliquot (10 μL) of this solution is diluted to 2 mL with deionized water. An aliquot (290 μL) is further diluted to 20 mL with assay buffer and is ready for use. The incubation time is shortened from 90 min. to 30 min. Lastly, during the filtering portion of the assay, the tube is not washed with filtering buffer (0.5 mL).

When tested as described above, the C26 desmethyl analogue 702.1 (Example 3A), had significantly higher activity than the corresponding C26 methyl-containing analogue (Formula 1998a where $R^3$ is OH). Similarly, among several analogues having different C20 ester groups, the presence of longer R20 substituents (48) or an aryl substituent (49) also afforded higher activity. The results are shown below in Table 1 (in all compounds tested, $R^3$ was OH and $R^{21}$ was =CH—$CO_2$Me).

TABLE 1

| Compound | $R^{20}$ | $R^{26}$ | PKCδ-C1B Assay $K_i$ (nM) |
|---|---|---|---|
| Phorbol dibutyrate | | | 1.7 ($K_d$ value) |
| Formula 1998a | —OC(O)$C_7H_{15}$ | $CH_3$ | 5.1 |
| Formula IIa (702.1) | —OC(O)$C_7H_{15}$ | H | 0.30 ± 0.07 |
| Formula 702.2 | —OC(O)$CH_3$ | $CH_3$ | 232 ± 11 |
| Formula 702.3 | —OC(O)$C_6H_{13}$ | $CH_3$ | 35 |
| Formula 702.4 | —OC(O)$C_{13}H_{27}$ | $CH_3$ | 1.3 |
| Formula 702.5 | —OC(O)Phenyl | $CH_3$ | 1.7 |

Example 7

P388 Murine Lymphocytic Leukemia Cell Assay

Cells from a P388 cell line (CellGate, Inc., Sunnyvale, Calif.) are grown in RPMI 1640 cell medium containing fetal calf serum (10%), L-glutamine, penicillin, streptomycin and are split twice weekly. All compounds are first diluted with DMSO. Later serial dilutions are done with a phosphate buffer solution (HYQ DPBS modified phosphate buffered saline). All dilutions are done in glass vials and the final DMSO concentration is always below 0.5% by volume. Final two-fold dilutions are done in a 96 well plate using cell media so that each well contains 50 μL. All compounds are assayed in quadruplicate over 12 concentrations. Cell concentration is measured using a hemacytometer and the final cell concentration is adjusted to $1 \times 10^4$ cells/mL with cell medium. The resulting solution of cells (50 μL) is then added to each well and the plates are incubated for 5 days in a 37° C., 5% $CO_2$, humidified incubator (Sanyo $CO_2$ incubator). MTT solution (3-[4,5-dimethylthiazol-2-yl]-2,5-diphenyltetrazolium bromide, 10 μL) is then added to each well and the plates are re-incubated under identical conditions for 2 h. To each well is then added acidified isopropanol (150 μL of i-PrOH solution containing 0.05 N HCl) and mixed thoroughly. The plates are then scanned at 595 nm and the absorbances are read (Wallac Victor 1420 Multilabel Counter). The resulting data is then analyzed to determine an $ED_{50}$ value using the Prism software package (GraphPad).

When tested as described above, the C26 desmethyl analogue 702.1 (Example 3A), had significantly higher activity than the corresponding C26 methyl-containing analogue. Similarly, among several analogues having different C20 ester groups, the presence of longer R20 substituents (48) or an aryl substituent (49) also afforded higher activity. The results are shown below in Table 2 (in all compounds tested, $R^3$ was OH and $R^1$ was =CH—$CO_2$Me).

TABLE 2

| Compound | $R^{20}$ | $R^{26}$ | P388 Assay $ED_{50}$ (nM) |
|---|---|---|---|
| Formula 1998a | —OC(O)$C_7H_{15}$ | $CH_3$ | 76 |
| Formula IIa (702.1) | —OC(O)$C_7H_{15}$ | H | 17 |
| Formula 702.2 | —OC(O)$CH_3$ | $CH_3$ | 181 |
| Formula 702.3 | —OC(O)$C_6H_{13}$ | $CH_3$ | 38 |
| Formula 702.4 | —OC(O)$C_{13}H_{27}$ | $CH_3$ | 3.6 |
| Formula 702.5 | —OC(O)Phenyl | $CH_3$ | 42 |

Example 8

In Vitro Inhibition of Growth in Human Cancer Cell Lines

Anticancer data were obtained in vitro for C26 desmethyl bryostatin analogue 702.1 (Example 3A) tested against a spectrum of different NCI human cancer cell-lines associated with various cancer conditions. The results are shown in Table 3. Data obtained with Bryostatin-1 are included for comparison. Growth inhibition (GI50) values are expressed as the log of molar concentration at half-maximum inhibition. As can be seen, the C26 desmethyl compound was at least as potent, on average, as bryostatin-1 for all cell groups tested. Moreover, the C26 desmethyl compound was more active than bryostatin-1 by more than 2 orders of magnitude for several cell lines: K-562 and MOLT-4 (leukemia), NCI-H460 (NSC lung), HCC-2998 (colon), TK-10 (renal), and MDA-MB-435 (breast). These results are significant and surprising since the C27 methyl group attached to C26 was previously believed to be necessary for activity.

TABLE 3

| Cell Line: | desmethyl | Bryo-1 | Difference |
|---|---|---|---|
| Leukemia | | | |
| CCRF-CEM | −5.81 | −5.30 | −0.51 |
| HL-60(TB) | −5.84 | −5.70 | −0.14 |
| K-562 | −7.5 | −5.40 | −2.10 |
| MOLT-4 | <−8.0 | −5.50 | −2.50 |
| RPMI-8226 | −5.82 | >−5 | −0.82 |
| SR | −5.1 | >−5 | −0.10 |
| NSC Lung | | | |
| A549/ATCC | −6.62 | −5.20 | −1.42 |
| EKVX | −5.58 | −5.30 | −0.28 |
| HOP-62 | −4.79 | >−5 | |
| HOP-92 | −4.67 | −5.30 | 0.63 |
| NCI-H226 | | >−5 | |
| NCI-H23 | | >−5 | |
| NCI-H322M | −4.38 | −6.00 | 1.62 |
| NCI-H460 | <−8 | −5.60 | −2.40 |
| NCI-H522 | | >−5 | |
| Colon | | | |
| COLO 205 | −7.08 | −5.40 | −1.68 |
| HCC-2998 | −7.54 | −5.30 | −2.24 |
| HCT-116 | −5.32 | −5.30 | −0.02 |
| HCT-15 | −4.76 | >−5 | |
| HT29 | −5.55 | −5.30 | −0.25 |
| KM12 | −5.34 | −5.20 | −0.14 |
| SW-620 | −5.12 | −5.50 | 0.38 |
| CNS | | | |
| SF-268 | −4.97 | −5.10 | 0.13 |
| SF-295 | −6.05 | −5.20 | −0.85 |
| SF-539 | −5.77 | >−5 | −0.77 |
| SNB-19 | −5.2 | >−5 | −0.20 |

TABLE 3-continued

| Cell Line: | desmethyl | Bryo-1 | Difference |
|---|---|---|---|
| SNB-75 | −4.97 | −5.50 | 0.53 |
| U251 | −5.4 | −5.10 | −0.30 |
| Prostate | | | |
| PC-3 | −5.6 | −5.30 | −0.30 |
| DU-145 | −5.02 | >−5 | −0.02 |
| Melanoma | | | |
| LOX IMVI | −5.47 | −5.10 | −0.37 |
| MALME-3M | | −5.20 | |
| MI4 | −5.26 | >−5 | −0.26 |
| SK-MEL-2 | −5.02 | −5.20 | 0.18 |
| SK-MEL-28 | −4.67 | −5.10 | 0.43 |
| SK-MEL-5 | −6.43 | −5.70 | −0.73 |
| UACC-257 | −5.13 | −5.10 | −0.03 |
| UACC-62 | −5.11 | −5.30 | 0.19 |
| Ovarian | | | |
| IGROVI | −4.88 | −5.30 | 0.42 |
| OVCAR-3 | −4.83 | −5.10 | 0.27 |
| OVCAR-4 | −5.15 | −5.50 | 0.35 |
| OVCAR-5 | −5.28 | >−5 | −0.28 |
| OVCAR-8 | −4.77 | −5.10 | 0.33 |
| SK-OV-3 | −4.3 | −5.10 | 0.80 |
| Renal | | | |
| 786-0 | −5.46 | −5.20 | −0.26 |
| A498 | −6.38 | >−5 | −1.38 |
| ACHN | −5.94 | −5.50 | −0.44 |
| CAKI-1 | −5.7 | −5.40 | −0.30 |
| RXF-393 | | −5.30 | |
| SN12C | −5.59 | −5.10 | −0.49 |
| TK-10 | −7.03 | >−5 | −2.03 |
| UO-31 | −4.85 | −5.60 | 0.75 |
| Breast | | | |
| MCF7 | −5.4 | −5.20 | −0.20 |
| NCI/ADR-RES | −4.74 | >−5 | |
| MDA-MB-231/ATCC | −5.69 | −5.20 | −0.49 |
| MDA-MB-435 | −7.66 | −5.10 | −2.56 |
| MDA-N | | −5.10 | |
| BT-549 | −4.71 | −5.10 | 0.39 |
| T-47D | −5.02 | −5.20 | 0.18 |
| HS 578T | −5.18 | −5.2 | 0.02 |

Documents Cited by Reference

Alkatib, A., Exp. Hematol. 21:61–65 (1993).
Aprahamian et al., J. Biomed. Mat. Res. 21:965–977 (1986).
Berkow, R. L. et al., Biochem. Biophys. Res. Commun. 131:1109–1116 (1985).
Blumberg et al., W097/34598 (1997) (corresponding to U.S. Pat. No. 6,060,505).
Boyd, M. R., "Status of the NCI preclinical antitumor drug discovery screen" in Cancer: Principles and Practice of Oncology Updates, DeVita et al., eds, pp. 1–12 (1989).
DeVries, D. J., et al., Biochem. Pharmacol. 37:4069–4073 (1998).
Emmanuel et al., Stain. Tech. 62:401–409 (1987).
Evans, D. A.; et al., Angew. Chem. Int. Ed. 37:2354–2359 (1998).
Evans, D. A.; et al., Angew. J. Am. Chem. Soc. 121:7540–7552 (1999).
Friendenstein et al., Exp. Hematol. 10:217–227 (1982).
Gennaro, A. R., Ed., Remington's Pharmaceutical Sciences, 18th Ed., Mack Publishing Co., Easton, Pa. (1990).
Grever, M. R., et al. Seminars Oncol. 19:622 (1992).
Harada et al. J. Am. Chem. Soc. 115:7665–7674(1993).
Hardman, J. G., et al. (eds), Goodman & Gilmans's The Pharmacological Basis of Therapeutics, Ninth Edition, McGraw-Hill, New York, N.Y., Chapter 51 (1996).
Hornung, R. L., et al., Cancer Res. 52:101–107 (1992).
Irie, K., et al., J. Am. Chem. Soc. 120:9159 (1998).
Kageyama, M., et al., J. Am. Chem. Soc. 112:7407–7408 (1990).
Katzung, B. G. (Editor), Basic & Clinical Pharmacology, Seventh Ed., Appleton & Lange, Stamford, Conn., 1998, Chapter 55.
Kraft, A. S., et al., Proc. Natl. Acad. Sci. USA 83:1334–1338 (1986).
Kraft, A. S., et al., Cancer Chemother. Pharmacol. 37:271–278 (1996).
Lind, D. S., et al., Surgical Oncol.-Oxford 2:273–282 (1993).
Maki, A., et al., Anti-Cancer Drugs 6:392–397 (1995).
Masamune, S., Pure Appl. Chem 60:1587–1596 (1988a).
Masamune, S., Chimica 42:210–211 (1988b).
Mochly-Rosen, D., and Koshland Jr., D. E., J. Biol. Chem. 262:2291–2297 (1986).
Mohammad, R. M., et al., Leukemia Res. 19:667–673 (1995).
Mohammad, R. M., et al., Leukemia 10:130–137 (1996).
Mohammad, R. M., et al., Clin. Cancer Res. 4:1337–1343 (1998).
Monks, A., et al., J. Natl. Cancer Inst., 83:757–766 (1991).
Pettit, G. R., et al., J. Am. Chem. Soc. 104:6846–6848 (1982).
Pettit, G. R. J. Nat. Prod. 59:812–821 (1996), and references cited therein.
Ramsdell, J., et al., J. Biol. Chem. 261:7073–7080 (1986).
Scheid, C., et al., Cancer Immunol. Immunother. 39:223–230 (1994).
Schuchter, L. M., et al., Cancer Res. 51:682–687 (1991).
Spitaler, M., et al., Biochem. Pharmacol. 56:861–869 (1998).
Still, C., et al., J. Org. Chem. 43:2923 (1978).
Szallasi, Z., et al., Cancer Res. 56:2105–2111 (1996), and references cited therein.
Tanaka, Y., et al., J. Biochem. 99:257–261 (1986).
Theisen, P. D., et al. J. Org. Chem. 53:2374–2378 (1998).
Uchida et al., J. Biomed. Mat. Res. 21:1–10 (1987).
Wender, P. A., et al., Proc. Natl. Acad. Sci. U.S.A. 92:239 (1995).
Wender, P. A., et al., J. Am. Chem. Soc. 120:4534–4535 (1998a).
Wender, P. A., et al., Proc. Natl. Acad. Sci. U.S.A. 95:6624–6629 (1998b).
Wender, P. A., et al., Tetrahedron Letters 39:8625–8628 (1998c).
Wilson, J. D., et al. (Editors), Harrison's Principles of Internal Medicine, Twelfth Ed., 1991, Chapters 300–310.

All references cited herein are hereby incorporated by reference. Although the invention has been described with respect to specific embodiments and examples, it will be appreciated that various changes and modifications may be made without departing from the spirit of the invention.

What is claimed is:

1. A compound having the structure represented by Formula I:

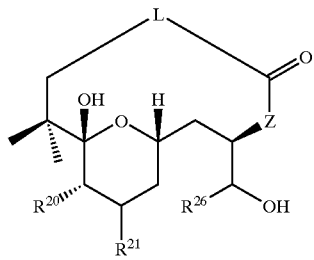

Formula I

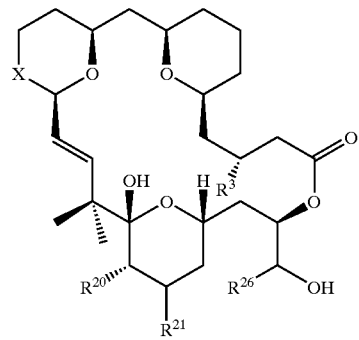

Formula II

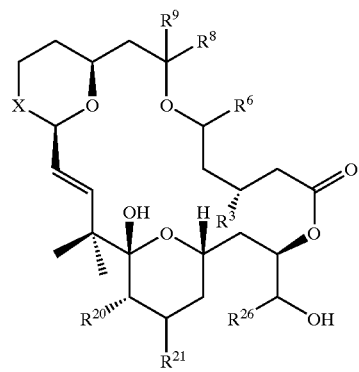

Formula III

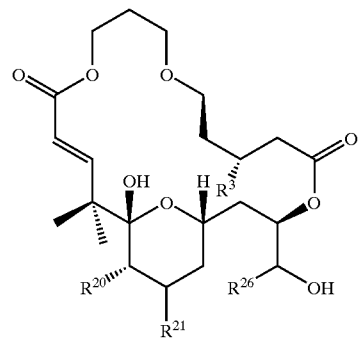

Formula IV

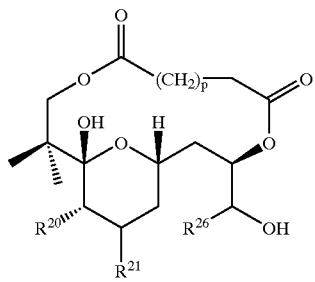

Formula V wherein:
  $R^{20}$ is H, OH, or $O_2CR'$;
  $R^{21}$ is $=CR^aR^b$ or $R^{21}$ represents independent moieties $R^c$ and $R^d$ where:
    $R^a$ and $R^b$ are independently H, $CO_2R'$ or R';
    $R^c$ and $R^d$ are independently H, alkyl, alkenyl or alkynyl containing 1 to 20 carbon atoms, or $(CH_2)_n\ CO_2R'$ where n is 1, 2 or 3;
  $R^{26}$ is H, OH or R';
    each R' being independently selected from the group: alkyl, alkenyl or alkynyl containing 1 to 20 carbon atoms, or aryl, heteroaryl, aralkyl or heteroaralkyl containing 2 to 20 carbon atoms; and
  L consists essentially of a straight or branched linear, cyclic or polycyclic, lipophilic moiety containing a continuous chain of from 6 to 14 chain atoms, which substantially maintains relative distance of the C1 and C17 atoms and the directionality of the C1C2 and C16C17 bonds of naturally-ocurring bryostatin; and
  Z is —O— or —N(H)—;
or a pharmaceutically acceptable salt thereof, excluding the compounds of Formula I where $R^{26}$ is methyl.

2. The compound or salt of claim 1 wherein Z is oxygen.

3. The compound or salt of claim 1 or 2 wherein $R^{26}$ is hydrogen.

4. The compound or salt of claim 1 or 2 wherein $R^{20}$ is $O_2CR'$.

5. The compound or salt of claim 4 wherein $R^{26}$ is hydrogen.

6. The compound or salt of claim 4 wherein the R' of said $R^{20}$ substituent is selected from: alkyl having from about 7 to 20 carbon atoms, alkenyl having from about 7 to 20 carbon atoms, phenyl and naphthyl.

7. The compound or salt of claim 1 or 2 wherein $R^{21}$ is $=C(H)CO_2R'$.

8. The compound or salt of claim 7 wherein $R^{26}$ is hydrogen.

9. The compound or salt of claim 8 wherein the R' of said $R^{21}$ substituent is $C_1$–$C_{10}$ alkyl.

10. The compound or salt of claim 7 wherein $R^{20}$ is $O_2CR'$.

11. A pharmaceutical composition comprising a compound or salt of claim 1 and a pharmaceutically acceptable excipient.

12. A compound having the structure represented by any of Formulae II–V:

wherein:
  $R^3$ is H or OH;
  $R^6$ is H, H or $=O$;
  $R^8$ is selected from the group: H, OH, R', —$(CH_2)_nO(O)CR'$ or $(CH_2)_nCO_2$-haloalkyl, where n is 0, 1, 2, 3, 4 or 5;

$R^9$ is H or OH;

$R^{20}$ is H, OH, or $O_2CR'$;

$R^{21}$ is $=CR^aR^b$ or $R^{21}$ represents independent moieties $R^c$ and $R^d$ where:

$R^a$ and $R^b$ are independently H, $CO_2R'$ or R';

$R^c$ and $R^d$ are independently H, alkyl, alkenyl or alkynyl containing 1 to 20 carbon atoms, or $(CH_2)_qCO_2R'$ where q is 1, 2 or 3;

$R^{26}$ is H, OH or R';

p is 1, 2, 3 or 4; and

X is C, O, S or N—$R^e$ where $R^e$ is COH, $CO_2R'$ or $SO_2R'$;

each R' being independently selected from the group: alkyl, alkenyl or alkynyl containing 1 to 20 carbon atoms, or aryl, heteroaryl, aralkyl or heteroaralkyl containing 2 to 20 carbon atoms, or a pharmaceutically acceptable salt thereof, excluding the compounds of formula 1998a where $R^3$ is H or OH and where $R^{20}$ is —O—C(O)—$CH_3$ or —O—C(O)—$(CH_2)_6$—$CH_3$, and the compounds of formula 1998b where $R^8$ is H or t-Bu:

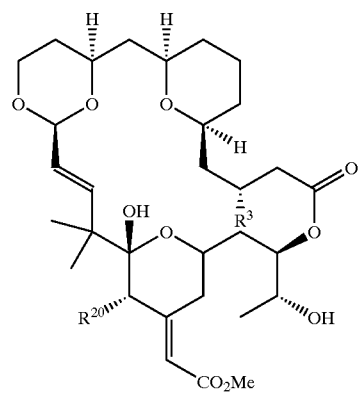

1998a

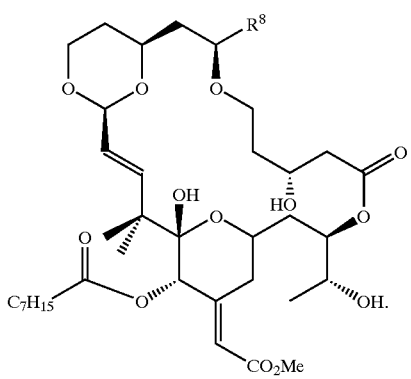

1998b

13. The compound or salt of claim 12 wherein $R^{26}$ is hydrogen.

14. The compound or salt of claim 12 or 13 being selected from Formula II or Formula III where X is oxygen.

15. The compound or salt of claim 12 or 13 wherein $R^{20}$ is $O_2CR'$.

16. The compound or salt of claim 12 or 13 wherein $R^{21}$ is $=C(H)CO_2R'$.

17. The compound or salt of claim 12 or 13 being selected from Formula II–IV where $R^3$ is OH.

18. The compound or salt of claim 14 wherein $R^{20}$ is $O_2CR'$.

19. The compound or salt of claim 18 wherein the R' of said $R^{20}$ substituent is selected from: alkyl having from about 7 to 20 carbon atoms, alkenyl having from about 7 to 20 carbon atoms, phenyl and naphthyl.

20. The compound or salt of claim 18 wherein $R^{21}$ is $=C(H)CO_2R'$.

21. The compound or salt of claim 14 where $R^8$ is —$(CH_2)_nO(O)CR'$.

22. The compound of claim 12 represented by Formula IIa:

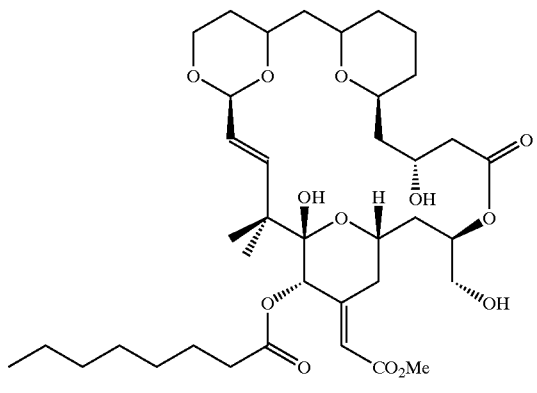

Formula IIa or a pharmaceutically acceptable salt thereof.

23. A pharmaceutical composition comprising a compound or salt of claim 12 or 22 and a pharmaceutically acceptable excipient.

24. A C26 des-methyl bryostatin homologue having the structure represented by any of Formula VI Formula VII or C26 des-methyl Bryostatin 3:

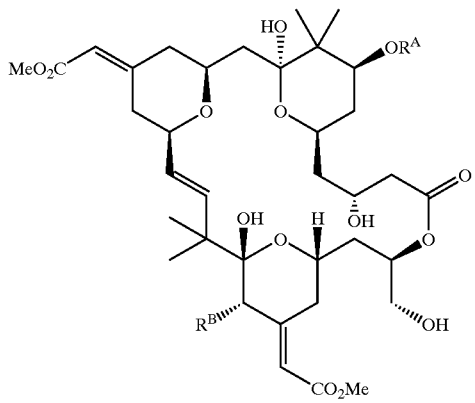

Formula VI where $OR^A$ and $R^B$ correspond to naturally occurring bryostatin substituents, comprising:

| Byrostatin | OR^A | R^B |
|---|---|---|
| 1 | —O$_2$C—CH$_3$ | —O$_2$C—CH=CH—CH=CH—CH$_2$—CH$_2$—CH$_3$ |
| 2 | —OH | —O$_2$C—CH=CH—CH=CH—CH$_2$—CH$_2$—CH$_3$ |
| 4 | —O$_2$C—C(CH$_3$C)$_3$ | —O$_2$C—CH$_2$—CH$_3$ |
| 5 | —O$_2$C—C(CH$_3$C)$_3$ | —O$_2$C—CH$_3$ |
| 6 | —O$_2$C—CH$_2$—CH$_3$ | —O$_2$C—CH$_3$ |
| 7 | —O$_2$C—CH$_3$ | —O$_2$C—CH$_3$ |
| 8 | —O$_2$C—CH$_2$—CH$_3$ | —O$_2$C—CH$_2$—CH$_3$ |
| 9 | —O$_2$C—CH$_3$ | —O$_2$C—CH$_2$—CH$_3$ |
| 10 | —O$_2$C—C(CH$_3$C)$_3$ | —H |
| 11 | —O$_2$C—CH$_3$ | —H |
| 12 | —O$_2$C—CH$_2$—CH$_3$ | —O$_2$C—CH=CH—CH=CH—CH$_2$—CH$_2$—CH$_3$ |
| 13 | —O$_2$C—CH$_2$—CH$_3$ | —H |
| 14 | —O$_2$C—C(CH$_3$C)$_3$ | —OH |
| 15 | —O$_2$C—CH$_3$ | —O$_2$C—CH=CH—CH=CH—CH$_2$—CH$_2$—CH$_3$ |
| 18 | —O$_2$C—C(CH$_3$C)$_3$ | —H; |

Formula VII

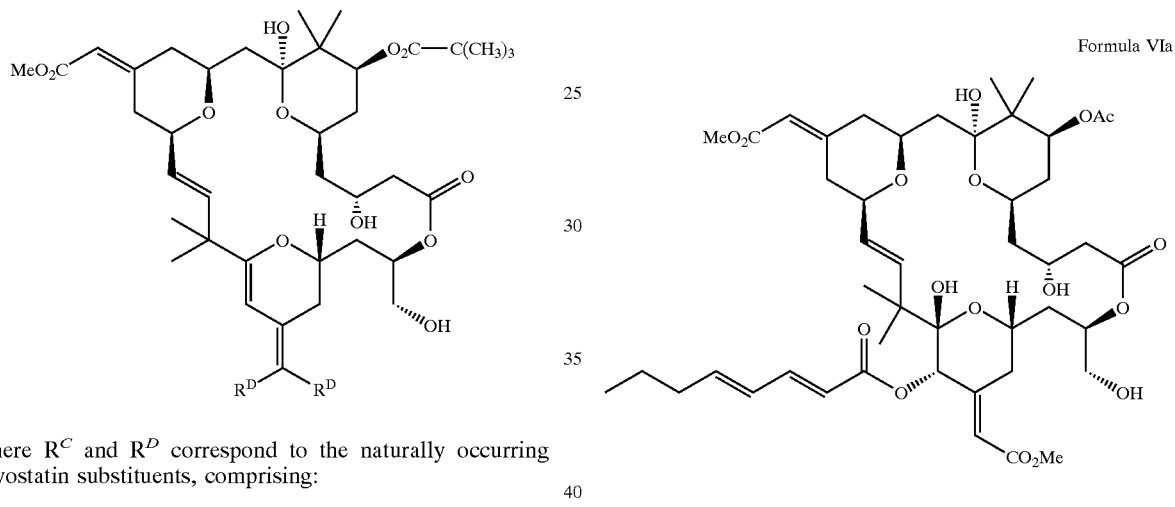

where $R^C$ and $R^D$ correspond to the naturally occurring bryostatin substituents, comprising:

| Byrostatin | R^C | R^D |
|---|---|---|
| 16 | —H | —CO$_2$Me |
| 17 | —CO$_2$Me | —H: | and

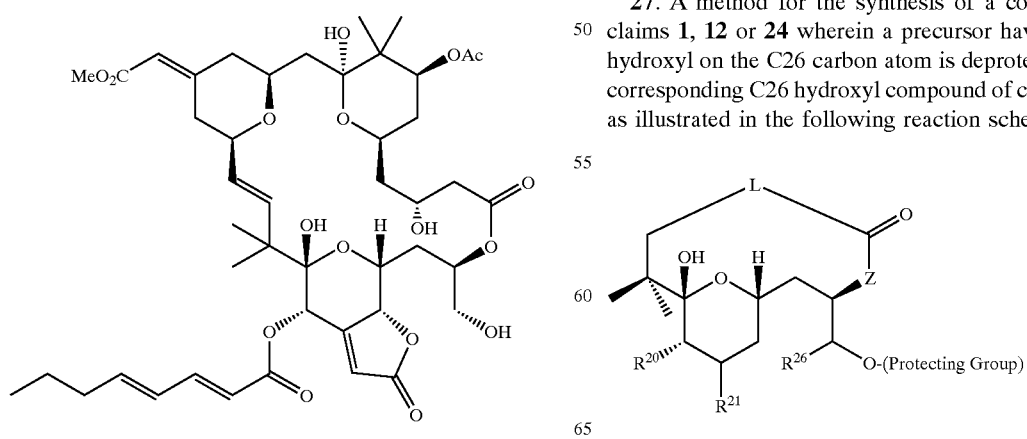

or a pharmaceutically acceptable salt thereof.

25. The C26 des-methyl bryostatin homologue of claim 24 having the structure represented by Formula VIa:

Formula VIa or a pharmaceutically acceptable salt thereof.

26. A method of treatment for a disorder responsive to bryostatin therapy comprising administering to a mammal in need thereof an effective amount of a compound or pharmaceutically acceptable salt of any of claims 1, 12 or 24.

27. A method for the synthesis of a compound any of claims 1, 12 or 24 wherein a precursor having a protected hydroxyl on the C26 carbon atom is deprotected to give the corresponding C26 hydroxyl compound of claim 1, 12 or 24, as illustrated in the following reaction scheme:

-continued

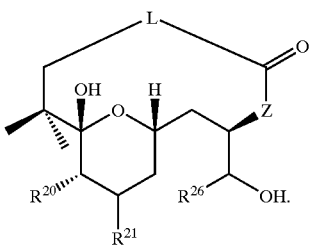

28. The method of treatment of claim 26 further comprising the step of co-administering a second agent having therapeutic activity via an immunosuppressive mechanism distinct from that of bryostatin.

29. A method of treatment for a hyperproliferative cellular disorder or an immune-related disorder comprising administering to a mammal in need thereof an effective amount of a compound or pharmaceutically acceptable salt of any of claims 1, 12 or 24.

30. The method of treatment of claim 29, further comprising the step of co-administering a second agent having therapeutic activity via an immunosuppressive mechanism.

* * * * *